(12) United States Patent
Kong et al.

(10) Patent No.: US 9,345,667 B2
(45) Date of Patent: May 24, 2016

(54) PARTICLES HAVING HYDROPHOBIC MATERIAL THEREIN

(75) Inventors: Linggen Kong, New South Wales (AU); Christophe Jean Alexandre Barbe, New South Wales (AU); Kim Suzanne Finnie, New South Wales (AU)

(73) Assignee: Australian Nuclear Science and Technology Organisation (AU)

( * ) Notice: Subject to any disclaimer, the term of this patent is extended or adjusted under 35 U.S.C. 154(b) by 1616 days.

(21) Appl. No.: 11/917,432

(22) PCT Filed: Jun. 19, 2006

(86) PCT No.: PCT/AU2006/000852
§ 371 (c)(1),
(2), (4) Date: Feb. 28, 2008

(87) PCT Pub. No.: WO2006/133518
PCT Pub. Date: Dec. 21, 2006

(65) Prior Publication Data
US 2009/0246279 A1    Oct. 1, 2009

(30) Foreign Application Priority Data
Jun. 17, 2005    (AU) .................................. 2005903193

(51) Int. Cl.
*A61K 9/10* (2006.01)
*A61K 9/16* (2006.01)
(Continued)

(52) U.S. Cl.
CPC ............... *A61K 9/1611* (2013.01); *C01G 1/02* (2013.01); *C09C 1/3063* (2013.01);
(Continued)

(58) Field of Classification Search
None
See application file for complete search history.

(56) References Cited

U.S. PATENT DOCUMENTS 4,011,096 A    3/1977    Sandell
4,224,179 A    9/1980    Schneider
(Continued)

FOREIGN PATENT DOCUMENTS

EP    0 481 892 A1    4/1992
JP    2001-354820    12/2001
(Continued)

OTHER PUBLICATIONS

Li et al. Synthesis and Characterization of Stable Hollow Ti-Silica Microspheres With a Mesoporous Shell, Chem. Materials, vol. 17, No. 9, (Apr. 2005).*

(Continued)

*Primary Examiner* — Ileana Popa
*Assistant Examiner* — Nicole Babson
(74) *Attorney, Agent, or Firm* — Baker & Hostetler LLP

(57) ABSTRACT

A process for preparing particles having a hydrophobic material therein is disclosed. The process comprises providing a multiple emulsion comprising a first emulsion dispersed in a hydrophobic medium, said first emulsion comprising a hydrophobic phase dispersed in a hydrophilic phase, wherein the hydrophobic phase comprises the hydrophobic material and the hydrophilic phase comprises a precursor which is capable of reacting to form a non-fluid matrix and reacting the precursor in the multiple emulsion to form the matrix in the form of the particles having the hydrophobic material therein wherein the precursor is added prior to formation of the multiple emulsion. Also disclosed are particles having a hydrophobic material therein, which may be releasable, as well as particles having a hydrophobic material therein, which may be releasable, made by the process and methods of using the particles.

14 Claims, 62 Drawing Sheets

(51) Int. Cl.
C01G 1/02 (2006.01)
C09C 1/30 (2006.01)
C09C 3/08 (2006.01)
C09C 3/12 (2006.01)

(52) U.S. Cl.
CPC .............. C09C 1/3072 (2013.01); C09C 3/08 (2013.01); C09C 3/12 (2013.01); C01P 2002/88 (2013.01); C01P 2004/03 (2013.01)

(56) References Cited

U.S. PATENT DOCUMENTS

| | | | |
|---|---|---|---|
| 4,579,779 | A | 4/1986 | Ohno |
| 5,178,871 | A | 1/1993 | Thill |
| 5,500,223 | A | 3/1996 | Behan et al. |
| 5,858,928 | A | 1/1999 | Aubert et al. |
| 5,990,183 | A * | 11/1999 | Kawano et al. ............ 521/64 |
| 6,586,479 | B2 | 7/2003 | Miller et al. |
| 6,627,603 | B1 | 9/2003 | Bibette et al. |
| 2003/0059472 | A1 | 3/2003 | Brynjelsen et al. |
| 2004/0048766 | A1 | 3/2004 | Raths et al. |
| 2004/0180096 | A1 | 9/2004 | Prasad et al. |

FOREIGN PATENT DOCUMENTS

| | | |
|---|---|---|
| WO | WO 99/07463 | 2/1999 |
| WO | WO 00/21504 | 4/2000 |
| WO | WO 01/01960 A1 | 1/2001 |
| WO | WO 01/62232 A1 | 8/2001 |
| WO | WO 03/013481 A1 | 2/2003 |
| WO | WO 03/066209 A1 | 8/2003 |
| WO | WO 2004/005355 A1 | 1/2004 |
| WO | WO 2004/043441 A1 | 5/2004 |
| WO | PCT/EP2004/014755 * | 8/2005 |
| WO | WO 2006/096571 A2 | 9/2006 |

OTHER PUBLICATIONS

Cho et al. Evaluation of Process Parameters in the O/W/O Multiple Emulsion Method for Flavor Encapsulation, Journal of Food Science vol. 68, Nr. 2, 2003.*

Croda Product Sheet. Specialty ingredients for personal care. www.crodalubricants.com/download.aspx?s=133&m=doc&id=133, accessed Nov. 7, 2013.*

Lindberg, R. Sjöblom, J., Sundholm, G. "Preparation of silica particles utilizing the sol-gel and the emulsion-gel processes" Colloids and Surfaces A: Physicochemical and Engineering Aspects, vol. 99, Issue 1, Jun. 10, 1995, pp. 79-88, ISSN 0927-7757.*

Croda Home Care. chemagent.ru/component/flexicontent/ download/849/970/19.accessed Nov. 7, 2013.*

Hongjiang Liu et al., "Fabrication of submicron Cu2O hollow spheres in an O/W/O multiple emulsions", Colloids and Surfaces A: Physicochem. Eng. Aspects 235 (2004) 79-82.

Yanqiu Jiang et al., "Synthesis of stable hollow spheres of Si/Al composite oxide with controlled pore size in the shell wall", Materials Letters 58 (2004) 2401-2405.

Chul Oh et al., "Distribution of Macropores in Silica Particles Prepared by Using Multiple Emulsions", Journal of Colloid and Interface Science 254, 79-86 (2002).

Jae-Hyung Park et al., "Preparation of hollow silica microspheres in W/O emulsions with polymers", Journal of Colloid and Interface Science 266 (2003) 107-114.

Jung Schick Lee et al., "Preparation of porous ceramic pellet by pseudo double-emulsion method from 4-phase foamed slurry", Journal of Materials Science Letters 20, 2001, pp. 205-207.

Jung Schick Lee et al., "Processing of porous ceramic spheres by pseudo-double-emulsion method", Ceramics International 29 (2003) 271-278.

Myung-Han Lee et al., "Preparation of Silica Particles Encapsulating Retinol Using O/W/O Multiple Emulsions", Journal of Colloid and Interface Science 240, 83-89 (2001).

Yi-Jeong Hwang et al., "Controlled release of retinol from silica particles prepared in O/W/O emulsion: The effects of surfactants and polymers", Journal of Controlled Release 106 (2005) 339-349.

A. Benichou et al., "Double emulsions stabilized with hybrids of natural polymers for entrapment and slow release of active matters", Advances in Colloid and Interface Science 108-109 (2004) 29-41.

Chul Oh et al., "O/W/O Multiple Emulsions via One-Step Emulsification Process", Journal of Dispersion Science and Technology, vol. 25, No. 1, pp. 53-62, 2004.

Shlomo Magdassi et al., "On the Factors Affecting the Yield of Preparation and Stability of Multiple Emulsions", J. Dispersion Science and Technology 5(1), 49-59 (1984).

Tsuneyasu Adachi et al., "Preparation of Spherical and Porous Chitosan Particles by Suspension Evaporation with O/W/O Multiple Emulsions", Polymer Journal, vol. 31, No. 4, pp. 319-323 (1999).

Katsunori Yoshida et al., "Stability of Vitamin A in Oil-in-Water-in-Oil-Type Multiple Emulsions", JAOCS, vol. 76, No. 2 (1999), pp. 195-200.

B.R. Midmore et al., "Silica-stabilised multiple emulsions", Progr. Colloid Polym Sci (1999) 112:115-120.

Y. H. Cho et al., "Evaluation of process factors in oil-water-oil multiple emulsion method for flavor encapsulation", http://ift.confex.com/ift/201/techprogram/paper_8530.htm.

Chul Oh et al., "Synthesis of mesoporous silica particles prepared by using multiple emulsion", Studies in Surface Science and Catalysis 146, 2003, pp. 189-192.

Nissim Garti et al., "Double Emulsions for Controlled-release Applications—Progress and Trends", Encyclopedic Handbook of Emulsion Technology, 2001, pp. 377-407.

Sang I. Seok et al, "Microencapsulation of Oil in Organically Modified Silicate Glass by Sol-Gel Process", Mat. Res. Soc. Symp. Proc. vol. 726, 2002, pp. 193-198.

Supplementary European Search Report EP 06 74 1255 dated May 25, 2011.

* cited by examiner a)

b)

(a)

(b)

(c)

(d)

a (bar = 400/70 μm)

b (bar = 400/80 μm)

c (bar = 80/40 μm)

d (bar = 80/30 μm)

e (bar = 50/19 μm)

f (bar = 400/80 μm)

a (bar = 400/70 μm)

b (bar = 400/50 μm)

c (bar = 400/50 μm):

d (bar = 400/90 μm)

e (bar = 400/30 μm)

f (bar = 400/70 μm)

c (bar = 500/70 μm) stir: 20 min.

d (bar = 400/70 μm) stir: 40 min.

bar = 50/70/70/10 μm a (bar = 400/24 μm)

b (bar = 400/70 μm)

c (bar = 400/90 μm)

d (bar = 400/40 μm)

a (bar = 400/60 μm)

b (bar = 400/70 μm)

a (bar = 500/40 μm)

b (bar = 500/60 μm)

c (bare = 500/150 μm)

a (bar = 500/40 μm)

b (bar = 500/60 μm)

c (bar = 500/120 μm)

d (bar = 500/90 μm)

a (bar = 400/80 μm)

b (bar = 400/70 μm)

Bar = 230/120 μm a (bar = 230 μm)  b (bar = 230 μm)

c (bar = 230 μm)  d (bar = 230 μm)

PARTICLES HAVING HYDROPHOBIC MATERIAL THEREIN

TECHNICAL FIELD

The present invention relates to particles which have hydrophobic material therein, and to processes for making them.

BACKGROUND OF THE INVENTION

The present inventors have developed a range of processes for encapsulating materials such as drugs and other biologically active materials, based on forming ceramic particles using sol-gel and related technology. These were developed for controlled release application, although other applications were also envisaged. These have been described in WO 01/62332, and in Australian patent application Nos AU 2005001738, AU 2005001915 and AU 2006000193.

These methods rely on the formation of water-in-oil emulsions, in which the encapsulant is located in the water phase. Consequently they are restricted to hydrophilic encapsulants which will partition preferentially into a dispersed water phase.

For the last decade, the encapsulation and controlled release of hydrophobic species has attracted considerable interest due to the increasing number of industrial applications using hydrophobic/lipophilic active molecules. For example, in the pharmaceutical and agricultural industries, many drugs or biocides possess hydrophobic properties. Nevertheless, the means to encapsulate and controllably release these active molecules remains a challenge for these industries. On the other hand, in food, cosmetics and personal care, encapsulation and controlled release of volatile organic compounds such as flavours and perfumes, or reactive compounds such as bleaches, is becoming a dominant trend for product improvement.

Compared with traditional organic materials, inorganic matrices and more specifically ceramics have many intrinsic advantages. In particular, they are biologically inert, intrinsically hydrophilic, and represent higher mechanical strength and thermal stability. However few inorganic delivery systems have achieved precise controlled release of the encapsulated molecules.

Double emulsions provide a means for encapsulating active materials in a delivery vehicle. These systems consist of two different interfaces that require two sets of different types of surfactants. In the case of O/W/O multiple emulsions, the first set of surfactants is preferably hydrophilic for the internal interface, while the second set of surfactants, for the external interface, is preferably hydrophobic. The composition of the double emulsion is critical since the nature and concentration of the different surfactants, along with the nature and concentration of the oil phase, will affect the stability of the double emulsion. Multiple emulsions (e.g. O/W/O) usually are prepared through a two-step process. In the first step, $O_1/W$ emulsions are prepared by dispersing the internal oil in an aqueous solution in the presence of a high HLB surfactant. The formation of an emulsion of very fine oil droplets in water is achieved by extensive energy input processes such as high shear homogenisation or ultrasonification. In the second step the $O_1/W$ emulsion is added to the external oil phase containing a low HLB surfactant. To disperse the inner phase ($O_1/W$ emulsion) in the external oil phase ($O_2$), a magnetic stirrer is generally used. The most commonly used double emulsions are of W/O/W type, but O/W/O emulsions have been used for specific applications.

Disadvantages of multiple emulsions include their intrinsic instability and the complexity of their structures, and consequently their applications have been substantially restricted despite their potential usefulness. In attempts to overcome their inherent instability, which results from the aggregation and coalescence between droplets in the inner phase, suitable combinations of emulsifiers have been used to improve the emulsion stability and reduce droplet sizes. The emulsifiers are absorbed at the surface of droplets during the formation of emulsions and prevent them from coming close enough to coalesce. Polymeric synthetic emulsifiers as well as natural macromolecules can be also used in combination with monomeric emulsifiers which have been shown to improve stability and controlled release.

By combining the advantages of the intrinsic properties of multiple emulsions with sol-gel chemistry, some hollow or porous inorganic spherical particles have been produced by sequentially introducing a catalyst and a metal alkoxide precursor in the water phase. However, very limited work has been conducted to produce spherical ceramic particles containing oil or hydrophobic species using a O/W/O multiple emulsion. This is due to the strict requirements of thermodynamically stable double emulsions i.e. very narrow domain of stability in the quaternary phase diagram (water-oil-$surf_1$-$surf_2$). Some work ["Preparation of Silica Particles Encapsulating Retinol Using O/W/O Multiple Emulsions", Lee, Myung-Han; Oh, Seong-Geun; Moon, Sei-Ki; Bae, Seong-Youl, Journal of Colloid and Interface Science, 240, 83-89 (2001)] has been undertaken to improve the stability of double emulsion by introducing thickening agents such as block co-polymers but with limited success. Once the metal alkoxide is added into the outer oil phase and subsequently reacted with water, the structure and stability of double emulsion is changed due to the perturbation in the balance of osmotic pressures between the two oil phases. This inherent thermodynamic instability of the double emulsion system, commonly leads to a further disadvantage with such systems: a fast (i.e. "burst") release of encapsulated materials into the outer oil phase.

Furthermore, the complex nature of multiple emulsions renders difficult the assessment of emulsion stability and the detection of rupture and coalescence. The main experimental technique is based on the measurement of the number and size of the multiple emulsion droplets which produces limited information on the emulsion stability because it is very difficult to determine if the internal droplets do coalesce, aggregate, or rupture. Again, introducing a significant amount of silicon precursor into the double emulsion system will increase the difficulty in monitoring the emulsion chemistry. Moreover, our inability to reproduce the preparation described by Lee et al. and the obtaining of nanoparticles instead of the microparticles described in their paper further confirm the significant instability and irreproducibility of such an approach.

There is therefore a need for a robust and versatile process for encapsulating a hydrophobic material into a particle. It would be preferable if such a process provided control over the size of the particle, and optionally also over the release rate of the hydrophobic material from the particle, as well as good encapsulation efficiency of the hydrophobic material.

OBJECT OF THE INVENTION

It is an object of the present invention to overcome or substantially ameliorate at least one of the above disadvantages. It is a further object to at least partially satisfy the above need.

SUMMARY OF THE INVENTION

In one form the present invention provides a process for preparing particles having a hydrophobic material therein, said process comprising:

providing a multiple emulsion comprising a first emulsion dispersed in a hydrophobic medium, said first emulsion comprising a hydrophobic phase dispersed in a hydrophilic phase, wherein the hydrophobic phase comprises the hydrophobic material and the hydrophilic phase comprises a precursor which is capable of reacting to form a non-fluid matrix; and reacting the precursor in the multiple emulsion to form the matrix in the form of the particles having the hydrophobic material therein;

wherein the precursor is added prior to formation of the multiple emulsion.

The step of reacting may comprise:

reacting the precursor in the multiple emulsion to form the matrix in the form of the particles having the hydrophobic material therein wherein the hydrophobic material is releasable from the particles.

The hydrophobic material in the particles may be releasable from the particles over a period of time. The hydrophobic material in the particles may be releasable from the particles in a controlled rate over a period of time.

The step of providing the multiple emulsion may comprise:

providing the first emulsion comprising the hydrophobic phase dispersed in the hydrophilic phase, wherein the hydrophobic phase comprises the hydrophobic material and the hydrophilic phase comprises the precursor; and dispersing the first emulsion in the hydrophobic medium to form the multiple emulsion In a first aspect of the invention there is provided a process for preparing particles having a hydrophobic material therein, said process comprising:

providing a first emulsion comprising a hydrophobic phase dispersed in a hydrophilic phase, wherein the hydrophobic phase comprises the hydrophobic material and the hydrophilic phase comprises a precursor which is capable of reacting to form a non-fluid matrix;

dispersing the first emulsion in a hydrophobic medium to form a multiple emulsion; and reacting the precursor in the multiple emulsion to form the matrix in the form of the particles having the hydrophobic material therein.

The multiple emulsion may be a double emulsion. It may be an oil-in-water-in-oil (O/W/O) multiple (or double) emulsion. The particles may be solid particles, and may be ceramic particles. The non-fluid matrix may be a solid or a gel. It may be filterable. It may be a filterable gel or a filterable solid. The non-fluid matrix may be a ceramic matrix. The internal hydrophobic phase may be a discontinuous phase. It may be encapsulated, compartmentalised, incorporated or enclosed in the matrix. The internal hydrophobic phase may comprise a hydrophobic diluent in addition to the hydrophobic material. The hydrophobic material may be miscible with or soluble in the hydrophobic diluent. The hydrophobic material may be composed of one or more than one kinds of hydrophobic materials. The first emulsion may additionally comprise a first surfactant, and the first surfactant may at least partially stabilise the first emulsion. The first surfactant may be a hydrophilic surfactant. It may be referred to as the "internal surfactant", as it may at least partially stabilise the first emulsion, which is internal to the multiple emulsion (i.e. it is located internally to the droplets or dispersed phase of the multiple emulsion). The hydrophilic phase may be a continuous phase. It may comprise water, and may be an aqueous phase. The precursor may be a precursor to the particles, i.e. to the matrix. If the particles are ceramic particles, the precursor may be a precursor to the ceramic, i.e. a ceramic precursor. It may be a crosslinkable material, or may be a partially crosslinked material or may be a mixture of these. It may be incapable of reacting with the hydrophobic material under the conditions under which it reacts to form the matrix. It may for example comprise a hydrolysable silane, an at least partially hydrolysed silane, a partially crosslinked silane, or a mixture of any two or more thereof.

The hydrophobic material may be for example a fluorescent dye, a radiopharmaceutical, a drug, an enzyme, a catalyst, a hormone, a biocide, a flavour, an aroma substance or some other substance, or it may be a mixture of any two or more of these.

The hydrophobic medium may be the same as or different to the hydrophobic diluent. It may comprise the hydrophobic diluent. The multiple emulsion may comprise a second surfactant, and the second surfactant may at least partially stabilise the multiple emulsion, although it is not necessary for the multiple emulsion to be stable. It may therefore be unnecessary to add an emulsion stabiliser other than a surfactant, and the process may be such that no emulsion stabiliser other than a surfactant is added. It may be unnecessary to add a thickening agent, and the process may be such that no thickening agent is added. No polymeric material may be added. There may be no methylcellulose, or cellulose based thickeners or other thickeners used in the process. There may be no emulsion stabilisers, other than surfactants, used in the process. The second surfactant may be combined with the hydrophobic medium, either before, during or after dispersing the first emulsion in the hydrophobic medium. For example, the step of dispersing may comprise dispersing the first emulsion in the hydrophobic medium having the second surfactant dissolved, suspended or dispersed therein, to form the multiple emulsion. The multiple emulsion may therefore comprise droplets of the first emulsion dispersed in the hydrophobic medium. The second surfactant may be a hydrophobic surfactant. It may be referred to as the "external surfactant" by contrast with the internal (or first) surfactant, as, in the multiple emulsion, it may be located externally relative to the first emulsion.

The first emulsion may be a microemulsion or it may be some other type of emulsion. It may have a mean droplet diameter between about 10 nm and about 50 microns. The multiple emulsion may have a mean droplet diameter between about 0.1 and about 1000 microns. The first emulsion and the multiple emulsion may, independently, have a narrow or a broad size distribution.

The process of forming the first emulsion may comprise the steps of:

combining the internal hydrophobic phase with water and the first surfactant to form a first mixture, and optionally agitating the first mixture;

combining a crosslinkable species with water to form a second mixture comprising the precursor and water, wherein either the crosslinkable species is the precursor or the crosslinkable species reacts in the presence of water, and optionally a catalyst (e.g. hydrolyses) to form the precursor;

combining the first mixture and the second mixture; and optionally, agitating the first and second mixtures to form the first emulsion.

In the first emulsion, the ratio of water to the hydrolysable species may be between about 2:1 and about 10:1, or between about 3:1 and about 6:1, on a molar basis. In the second mixture the ratio of water to the precursor may be between about 1:1 and about 5:1 on a molar, weight or volume basis.

The ratio of the amount of the first mixture and the amount of the second mixture that are combined may be between about 1:1 and 1:5 on a weight or volume basis. Formation of the precursor may take between about 5 minutes and about 48 hours. Following formation of the precursor, by-products, e.g. an alcohol, may be evaporated before combining the first and second mixtures, or may be partially evaporated or may not be evaporated. The optional step of agitating may comprise high shear, and may comprise high shear agitation, high shear mixing, sonication, ultrasonication or some combination of any 2, 3 or 4 of these. This may employ use of a sonicator or a mixer, e.g. a high shear mixer.

The proportion of the first emulsion in the multiple emulsion may be between about 1% and about 30% on a weight or volume basis. The step of dispersing the first emulsion in the hydrophobic medium may comprise the steps of:
providing a third mixture comprising the hydrophobic medium and the second surfactant;
combining the third mixture with the first emulsion; and
optionally, agitating the third mixture and the first emulsion.

The step of reacting the precursor to form the matrix may comprise ageing the multiple emulsion. The ageing may be for sufficient time to form the particles, and may be for example for between about 1 minute and about 50 hours, or between about 1 and about 10 hours, or between 5 and about 50 minutes. The time may depend on the pH of the first emulsion. The ageing may be at any convenient temperature at which the hydrophobic material is stable over the sufficient time, and may be between about 10 and 60° C. During said ageing, the multiple emulsion may or may not be agitated. The process may additionally comprise one or more of the steps of at least partially separating the particles from the hydrophobic medium, washing the particles and drying the particles. After the step of at least partially separating, the particles may be further aged. This may be for a suitable period for further reaction of the precursor. It may for example be between about 1 hour and about 24 hours or more, between about 30 minutes and 24 hours or more, between about 2 hours and about 24 hours or more, between about 3 hours and about 24 hours or more, between about 4 hours and about 24 hours or more, between about 5 hours and about 24 hours or more, or between about 7 hours and about 24 hours or more.

In an embodiment, the process comprises:
providing a first emulsion comprising a hydrophobic phase dispersed in a hydrophilic phase, wherein the hydrophobic phase comprises the hydrophobic material and the hydrophilic phase comprises a ceramic precursor, said first emulsion being at least partially stabilised by a first surfactant;
dispersing the first emulsion in a hydrophobic medium in the presence of a second surfactant to form a multiple emulsion; and
reacting the ceramic precursor in the multiple emulsion to form a ceramic in the form of ceramic particles having the hydrophobic material therein, said particles being dispersed in the hydrophobic medium.

In another embodiment the process comprises:
combining a hydrophobic phase with water and a first surfactant to form a first mixture, wherein the hydrophobic phase comprises the hydrophobic material and optionally also a hydrophobic diluent;
combining a crosslinkable species with water to form a second mixture comprising a precursor and water, wherein either the crosslinkable species is the precursor or the crosslinkable species reacts in the presence of water, and optionally a catalyst, to form the precursor;
combining the first mixture and the second mixture and, optionally, agitating the first and second mixtures, to form a first emulsion;
providing a third mixture comprising a hydrophobic medium and a second surfactant;
combining the third mixture with the first emulsion, and, optionally, agitating the third mixture and the first emulsion to form a multiple emulsion;
reacting the precursor in the multiple emulsion to form a solid matrix in the form of the particles having the hydrophobic material therein, said particles being dispersed in the hydrophobic medium;
at least partially separating the particles from the hydrophobic medium;
washing the particles; and
drying the particles.

The step of reacting may comprise:
reacting the precursor in the multiple emulsion to form a solid matrix in the form of the particles having the hydrophobic material therein, the hydrophobic material being releasable from the particles, said particles being dispersed in the hydrophobic medium;

There is also provided a particle when made by the process of the first aspect of the invention.

In a second aspect of the invention there is provided a particle having a hydrophobic material therein. The particle having hydrophobic material therein may be produced by a sol gel process which may be a process according to the invention. The particles may be xerogel particles. The particles may be gel particles. The particle may comprise a solid matrix having the hydrophobic therein. The hydrophobic material may be releasable from the particle. The hydrophobic material in the particles may be releasable from the particles over a period of time. The hydrophobic material in the particles may be releasable from the particles in a controlled or sustained rate over a period of time. The period of time for the particles per se or the particles made by the process of the invention may be in the range from 5 minutes to 72 hours or more, 10 minutes to 72 hours or more, 15 minutes to 72 hours or more, 20 minutes to 72 hours or more, 25 minutes to 72 hours or more, 30 minutes to 72 hours or more, 60 minutes to 72 hours or more, 90 minutes to 72 hours or more, 120 minutes to 72 hours or more, 5 minutes to 48 hours, 10 minutes to 48 hours, 15 minutes to 48 hours, 20 minutes to 48 hours, 25 minutes to 48 hours, 30 minutes to 48 hours, 60 minutes to 48 hours, 90 minutes to 48 hours, 120 minutes to 48 hours, 5 minutes to 24 hours, 10 minutes to 24 hours, 15 minutes to 24 hours, 20 minutes to 24 hours, 25 minutes to 24 hours, 30 minutes to 24 hours, 60 minutes to 24 hours, 90 minutes to 24 hours, 120 minutes to 24 hours, 5 minutes to 12 hours, 10 minutes to 12 hours, 15 minutes to 12 hours, 20 minutes to 12 hours, 25 minutes to 12 hours, 30 minutes to 12 hours, 60 minutes to 12 hours, 90 minutes to 12 hours, 120 minutes to 12 hours, 5 minutes to 6 hours, 10 minutes to 6 hours, 15 minutes to 6 hours, 20 minutes to 6 hours, 25 minutes to 6 hours, 30 minutes to 6 hours, 60 minutes to 6 hours, 90 minutes to 6 hours, 120 minutes to 6 hours, 5 minutes to 3 hours, 10 minutes to 3 hours, 15 minutes to 3 hours, 20 minutes to 3 hours, 25 minutes to 3 hours, 30 minutes to 3 hours, 60 minutes to 3 hours, 90 minutes to 3 hours, 120 minutes to 3 hours, 5 minutes to 2 hours, 10 minutes to 2 hours, 15 minutes to 2 hours, 20 minutes to 2 hours, 25 minutes to 2 hours, 30 minutes to 2 hours, 60 minutes to 2 hours, 90 minutes to 2 hours, or 5 minutes to 1 hour. The particle may have a plurality of discrete cavities, cells, hollows or compartments. At least a portion of the hydrophobic material may be located in the discrete cavities, cells, hollows or compartments. The hydrophobic material may be encapsulated, compartmentalised, incorporated or enclosed in the particle, or in the matrix. More than one dopant, e.g. hydrophobic material, may be incorporated in the particles of the invention (e.g. 1, 2, 3, 4, 5, 6, 7, 8, 9, 10 or more dopants). The hydrophobic material may be for example a fluorescent dye, a radiopharmaceutical, a drug, an enzyme, a catalyst, a hormone, a biocide, a flavour, an aroma substance or some other substance, or it may be a mixture of any two or more of these. The particle may be made by a process that does not comprise use of a thickening agent. The particle may have no thickening agent or emulsion stabiliser therein or thereon, other than a surfactant. It may have no added polymer. It may have no added organic polymer. It may have no cellulose derivative (e.g. hydroxypropylcellulose) therein or thereon. The particle may be a solid particle, and may be a ceramic particle. The hydrophobic material may be encapsulated or at least temporarily immobilised in the particle. The particle may comprise between about 0.1 and 50% W/W or w/v of the hydrophobic material. The particle may have between about 10 and about $10^{10}$ discrete cavities, cells, hollows or compartments, or between about $10^6$ and $10^{10}$ discrete cavities, cells, hollows or compartments. The cavities, cells, hollows or compartments may be substantially spherical (i.e. spherical or approximately spherical), or some other shape, and may have a mean diameter between about 10 nm and about 50 microns. The particle may be spherical or some other shape, and may have a mean particle diameter between about 0.1 and about 1000 microns. Other molecules may be attached to or coupled to or coated on the particles of the invention. For example a targeting molecule may be attached to or coupled to or coated on the particles of the invention. The particle may comprise silica, a crosslinked silane or siloxane, a hydrolysed silane or siloxane, a silica-like material or a polysilsesquioxane. In particular, the particle may comprise silica. This has some important implications for the application of these particles. As silica they can be incorporated in food and oral/topical pharmaceutical formulation as the organo-silica are not approved by the various regulatory body. Furthermore, the fact that the particles are made of silica also makes them intrinsically hydrophilic. The possibility to encapsulate an hydrophilic compound in an hydrophilic matrix is a major step towards solving the problem of the delivery of poorly soluble drugs through the gut wall. The particle may be spherical. The particle may be capable of releasing the hydrophobic material. The particle may be capable of releasing the hydrophobic material over a period of time, i.e. the hydrophobic material may be releasably encapsulated and/or immobilised and/or incorporated in the particle. It may be a releasable hydrophobic material. The particle may be capable of releasing the hydrophobic material at a controlled rate. The rate may depend on the nature of the material, the nature of the hydrophobic material, the size of the discrete compartments, the size of the particle, the synthesis conditions of particles such as pH, the temperature, the nature of the medium in which the particle is immersed and/or other factors. The particle may be made by the process of the first aspect of the invention.

In a third aspect of the invention there is provided a method for treating a condition in a subject, for example a human, comprising administering to the subject a therapeutically effective quantity of particles according to the present invention, wherein the hydrophobic material of the particles is releasable from said particles and is indicated for the condition. The hydrophobic material may be a drug or some other therapeutic agent, and the drug may be an anti-cancer drug. The condition may be a disease. The condition may be for example cancer, AIDS, arthritis, diabetes, hormonal dysfunction, hypertension, pain or some other condition. The condition may be one for which controlled release of a drug or therapeutic agent is indicated. It may be one for which the drug or a therapeutic agent should be dispensed to the subject at a controlled rate. It may be one for which the drug or therapeutic agent should be dispensed to the subject over an extended period of time.

There is also provided a particle according to the present invention when used for the manufacture of a medicament for the treatment of a condition in a subject, for example a human, wherein the hydrophobic material of the particle is releasable from said particle and is indicated for the condition. There is also provided the use of a particle according to the present invention for the manufacture of a medicament for the treatment of a condition in a subject, for example a human or a non-human animal, wherein the hydrophobic material of the particle is releasable from said particle and is indicated for the condition. The condition may be for example cancer, diabetes, AIDS, hormonal dysfunction, hypertension, pain or some other condition.

There is also provided a process of making a composition comprising mixing the particles of the invention with an acceptable carrier, diluent, excipient and/or adjuvant.

There is further provided the use of particles or compositions according to the invention for the treatment of a condition in a subject, for example a human, wherein the hydrophobic material of the particles is releasable from said particles and is indicated for the condition. The condition may be for example cancer, diabetes, AIDS hormonal dysfunction, hypertension, pain or some other condition. The particles or compositions may be administered orally, topically, parenterally, for example. The administration may be via a single dose or multiple doses. The dosage of the particles administered will vary and will depend on such as the condition, age and size of the patient as well as the nature of the condition and the dopant, the effectiveness of the dopant, and the amount of dopant encapsulated and released by the particles.

In a fourth aspect of the invention there is provided a method for delivering a hydrophobic material, said method comprising exposing a plurality of particles according to the present invention to a medium capable of releasing the hydrophobic material of the particles, said hydrophobic material being releasable from the particles. The particles may be in the form of a composition comprising the particles. For parenteral administration, the particles of the invention of suitable size for the intended use may be prepared in sterile aqueous or oleaginous solution or suspension. Aqueous solutions or suspensions may further include one or more buffering agents and optionally other suitable additives for the intended purpose. Depending on the intended purpose, the dosage form of the composition will comprise from 0.005% to 80% by weight or more of the ceramic particles of the invention. Usually, dosage forms according to the invention will comprise from 0.1% to about 25%, more typically 1 to 16% and even more typically 1% to 10% by weight of the particles of the invention. The exposing may comprise immersing the particles in the medium, and may additionally comprise one or more of stirring, shaking, swirling or otherwise agitating the medium having the particles therein. Alternatively the exposing may comprise passing the medium past and/or through the particles. The medium may be a fluid, and may be a liquid. The medium may be a biological fluid such as blood. It may be an organic fluid, and may be an organic solvent, for example a hydrophobic solvent. The medium may be capable of dissolving or releasing the hydrophobic material. The hydrophobic material may be for example a fluorescent dye, a radiopharmaceutical, a drug, an enzyme, a hormone, a biocide, a flavour, an aroma substance or some other substance, or it may be a mixture of any two or more of these. The medium may be a gas, for example air, and the hydrophobic material may be volatile (for example an aroma material). The exposing may be under conditions suitable for release of the hydrophobic material into the medium. The exposing may be under conditions suitable for release of an effective amount to treat a condition of the hydrophobic material into the medium. The method may also comprise the step of allowing the hydrophobic material to release into the medium.

A further embodiment of the invention provides a method of treating a locus comprising applying particles of the invention or a composition according to the invention to the locus in an amount effective to treat the locus. Another embodiment of the invention provides a method of treating an object comprising administering to the object particles of the invention or a composition according to the invention to the object in an amount effective to treat the object. Yet a further embodiment of the invention provides a method of treating a subject comprising administering to the subject particles of the invention or a composition according to the invention to the subject in an amount effective to treat the subject.

Throughout the specification and claims the terms hydrophobic material, hydrophobe, hydrophobic active and hydrophobic active material may be used interchangeably.

DETAILED DESCRIPTION OF PREFERRED EMBODIMENTS OF THE INVENTION

Figure 1:
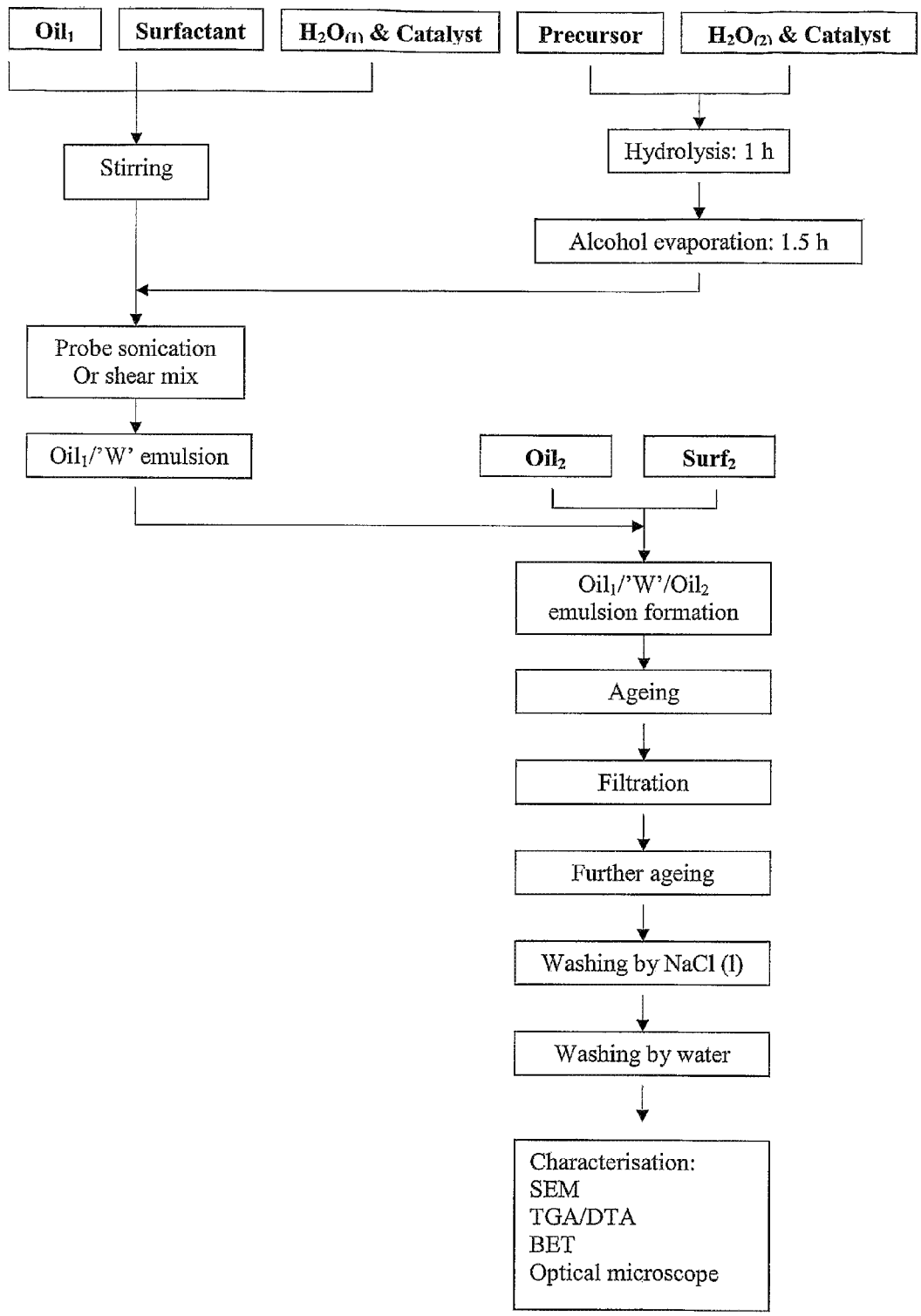
FIG. 1 is a flow chart showing a process for preparing a ceramic particle according to the present invention.

The present specification describes a process for producing ceramic particles using sol-gel technology via a multiple emulsion, e.g. an oil-in-water-in-oil double-emulsion (O/W/O), system. A multiple emulsion comprises an emulsion within an emulsion, i.e. the dispersed phase of the multiple emulsion is itself an emulsion. The dispersed phase of the multiple emulsion may be a simple emulsion (i.e. its continuous and dispersed phases are not themselves emulsions) or it may be a multiple emulsion. A multiple emulsion according to the present emulsion may be a double emulsion, a dual emulsion or a complex emulsion. It may be an O/W/O (oilwater-oil) double emulsion. It will be understood that in an O/W/O emulsion, the two oil phases may be the same, similar or dissimilar.

The results of analysing products of that process are presented herein. These micron or submicron sized particles (commonly in the range 0.1-1000 μm) contain hydrophobic materials, which may then be released in a controlled fashion. The particles may be synthesised by employing a combination of "process-1" described in C. J. Barbé, J. R Bartlett, Controlled Release Ceramic Particles, Compositions Thereof, Processes of Preparation and Methods, WO 01/62232 (2001) (the contents of which are incorporated herein by cross reference) and a double emulsion (O/W/O) approach. The hydrophobic material may be any organic molecule or hydrophobic compound, such as a dye or a drug, in both solid (e.g. retinol, diuron) and liquid form (e.g. limonene, basil oil). The hydrophobic material may be a solid or a liquid, or a mixture of solid and liquid. It may be in solution. Particle size, particle morphology and release rate of the hydrophobic material may be controlled by sol-gel processing parameters and/or double emulsion properties.

According to the present invention there is provided a process for making particles comprising a hydrophobic material therein. The process comprises providing a multiple emulsion, e.g. a double emulsion, comprising a first emulsion dispersed in a hydrophobic medium. The first emulsion comprises a hydrophobic phase dispersed in a hydrophilic phase, wherein the hydrophobic phase comprises the hydrophobic material and the hydrophilic phase comprises a precursor which is capable of reacting to form a non-fluid matrix. The precursor is then reacted in the multiple emulsion to form the matrix in the form of the particles having the hydrophobic material therein. The reaction may be a polymerisation, a condensation, a solidification, a crosslinking or some other reaction, or some combination of these. As the precursor reacts to form the particles, the hydrophobic material in the precursor material becomes at least partially encapsulated in the particles, thus reaction of the precursor forms the particles comprising the hydrophobic material therein. The hydrophobic material in the particles may be releasable from the particles. The hydrophobic material in the particles may be releasable from the particles over a period of time or in a controlled rate over a period of time.

Thus the hydrophobic material is at least partially encapsulated inside the cavities, cells, hollows or compartments. Release of the hydrophobic material from the particles appears to be controlled by the pore size of the matrix that surrounds these cavities, cells, hollows or compartments. It is possible to tailor the pore size distribution of the matrix by controlling the pH in the process of making the particles. Thus the sol-gel chemistry controls the pore size of the matrix. The internal surfactant may also affect the pore structure. The porosity of the matrix may comprise pores below about 100 nm, 90 nm, 80 nm, 70 nm, 60 nm, 50 nm, 40 nm, 30 nm, 20 nm, or below about 10, 5 or 2 nm, or between about 1 and about 20 nm, or between about 1 and 10, 1 and 5, 1 and 2, 5 and 20, 10 and 20 or 2 and 10 nm, and may comprise pores about 1, 2, 3, 4, 5, 6, 7, 8, 9, 10, 11, 12, 13, 14, 15, 16, 17, 18, 19 or 20 nm. These pores (micropores, mesopores or macropores) may control the release rate of the hydrophobic material. The porosity of the matrix is detected by nitrogen adsorption and the vacuoles are observed by SEM. They correspond to micro- (<2 nm) and meso-porosity (2 nm<p<50 nm) and macroporosity (>50 nm), respectively. By reducing the pH during synthesis of the particles, the pore volume and surface area are reduced. This may reduce the pore size or porosity of the matrix. It may reduce the release rate of the hydrophobic material. The hydrophobic material may be located at least in part in the pores of the matrix.

In contrast to earlier approaches, in an example of the present process illustrated in FIG. 1, a pre-hydrolysed precursor is mixed with an internal oil phase in the presence of hydrophilic surfactant. This hydrophilic phase (pre-hydrolysed precursor and water) with oil droplets distributed inside is poured into the mixture of outer oil phase and hydrophobic surfactant. This procedure is similar to "process-1" of WO 01/62232, with a key difference being that, in the present process, the sol-gel solution contains homogeneously distributed internal oil droplets. After mixing the internal $Oil_1$/'W' phase and outer $Oil_2$ phase, the hydrophilic droplets are formed. During this process, it is thought that the hydrolysed precursors condense to build spherical particles, entrapping the internal oil phase inside. This kinetic process may take place in a few to tens of minutes rather than hours (or even days) which are needed for traditional alkoxide reactions.

The present invention therefore provides a process for preparing a particle, for example a ceramic particle, having a hydrophobic material therein. The process comprises initially providing a first emulsion comprising a hydrophobic phase dispersed in a hydrophilic phase, wherein the hydrophobic phase comprises the hydrophobic material and the hydrophilic phase comprises a precursor which is capable of reacting to form a matrix. The first emulsion is then dispersed in a hydrophobic medium to form a multiple emulsion, and the precursor is reacted to form the matrix, thereby forming particles having the hydrophobic material therein, said particles being dispersed in the hydrophobic medium. The hydrophobic material in the particles may be releasable from the particles. The hydrophobic material in the particles may be releasable from the particles in a controlled rate over a period of time.

The formation of the solid particles and the formation of a double emulsion may occur concurrently, i.e. as the first emulsion is dispersing in the hydrophobic medium, the precursor may start to react to form the matrix. Thus formation of the matrix may commence as the first emulsion is combined with (i.e. dispersed in) the hydrophobic medium (strictly speaking, the formation of the matrix commences as soon as the water is added to the alkoxide. Therefore when the first emulsion is mixed with the external oil and the second surfactant (i.e. the hydrophobic medium) what happens is an acceleration of the condensation process, which leads to rapid gelation). The reaction of the precursor to form the matrix may take place in the double emulsion over a period of a few minutes to several tens of minutes or more. The longer the time over which the particles remain in the hydrophobic medium, the more likely the hydrophobic material is to diffuse out of the particles into the hydrophobic medium. Hence, once the particles are formed, they may be separated from the hydrophobic medium, e.g. by filtration, thereby inhibiting loss of hydrophobic material from the particles. Further reaction of the precursor may continue after said separation. The further reaction may continue for up to about 2, 4, 6, 12, 24, 36 or 48 hours or more, depending on temperature, reagents etc.

In a representative process according to the present invention, addition of water to an alkoxysilane commences the polymerisation process by hydrolysis and condensation. Addition of the solution of pre-hydrolysed alkoxysilane (the second mixture) to the first mixture (having the hydrophobic material and water) accelerates the rate of hydrolysis and condensation as the amount of water increases. Compartmentalisation of the first emulsion (made by combining the first and second mixtures) in the multiple emulsion further accelerates gelation of the precursor i.e. the formation of the particles. The rate of gelation is dependent on the "container" size (i.e. the size of the droplets of the first emulsion in the multiple emulsion) since it is defined by the formation of a siloxane cluster spanning the dimension of the "container". In other word the smaller the "container" the shorter the gel time (for identical chemistry). Thus the present process may proceed rapidly when the oil/water emulsion is added to the hydrolysed alkoxysilane and then added to the hydrophobic medium. If the first emulsion gels prior to being introduced in the multiple emulsion then particles may not form. If the first emulsion does not gel fast enough then the encapsulation efficiency may decrease because the chance of the internal oil droplet coming in contact with the outer hydrophobic medium increases. Thus immediately following dispersion of the first emulsion in the hydrophobic medium, the droplets of the first emulsion may be incompletely reacted, and thus may be soft. Over a suitable period of time, commonly around 10-20 minutes (although it may be a different time, depending on the chemistry and on the conditions) reaction may proceed to form the matrix.

The hydrophobic phase may comprise or consist of the hydrophobic material. It may comprise or consist of a solution or mixture comprising the hydrophobic material and a hydrophobic diluent (e.g. a hydrophobic solvent). The hydrophobic material may be for example a fluorescent dye, a radiopharmaceutical, a drug, an enzyme, a catalyst, a hormone, a biocide, a flavour, an aroma substance or some other substance, or it may be a mixture of any two or more of these. It may be incapable of reacting with the precursor under conditions under which the precursor reacts to form the matrix. It may comprise a hydrophobic solvent and a hydrophobic substance dissolved therein. The hydrophobic material may be volatile or non-volatile. The hydrophobic diluent, if present, may be a solvent for the hydrophobic material. It may be a hydrophobic liquid, and may be for example a liquid hydrocarbon (e.g. pentane, hexane, heptane, octane, decane, cyclohexane, benzene, toluene, xylene), a chlorinated solvent (e.g. chlorobenzene, dichlorobenzene, chloroform, dichloromethane, carbon tetrachloride, ethylene dichloride, dichloroethane, methyl chloroform), and ester (e.g. ethyl acetate), an ether (e.g. diethyl ether) or some other hydrophobic liquid. The proportion of the hydrophobic material in the hydrophobic phase may be between about 0.1 and 100% by weight or by volume, and may be between about 1 and 100, 10 and 100, 50 and 100, 80 and 100, 90 and 100, 0.1 and 50, 0.1 and 20, 0.1 and 10, 0.1 and 1, 1 and 50, 1 and 10, 10 and 50 or 10 and 20, and may be about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50, 60, 70, 80, 90, 95, 96, 97, 98, 99 or 100%. The hydrophobic phase may be pure or it may be diluted, for example with the diluent.

The hydrophilic phase may be an aqueous phase. It may be prepared by combining a crosslinkable species with water, thereby forming the precursor. The crosslinkable species may be a hydrolysable silane. The hydrolysable silane may have 2, 3 or 4 hydrolysable groups per molecule. The crosslinkable silane may be a mixture of silanes, in which the mean number of hydrolysable groups per molecule is between 2 and 4 (or between about 2 and about 3, about 3 and about 4, about 2.5 and about 3.5 or about 2.5 and about 4, and may be about 2, 2.5, 3, 3.5 or 4). The mixture of silanes may comprise individual silanes having 1, 2, 3 or 4 hydrolysable groups per molecule, provided that at least one of the silanes in the mixture has at least 3 hydrolysable groups per molecule. The hydrolysable groups may be alkoxy groups (e.g. methoxy, ethoxy, propoxy, isopropoxy) or may be aryloxy groups (e.g. phenoxy), or may be oximo groups (e.g. 2-butanoneoximo), enoloxy groups (e.g. propenyloxy) or some other hydrolysable groups. It may be for example tetramethoxysilane (TMOS), tetraethoxysilane (TEOS), tetrapropoxysilane (TPOS) or a functional trimethoxy, triethoxy or tripropoxysilane, for example aminopropylsilane, aminoethylaminopropylsilane or some other functional silane, for example methyltrimethoxysilane, ethyltrimethoxysilane, methyltriethoxysilane or ethyltriethoxysilane In a particular embodiment, a mixture of a alkoxide (e.g. a silane with alkoxide groups) and ORMOSIL e.g. functional tri-alkoxy silane is used. Alternatively, the crosslinkable species may be a hydrolysable titanate or a hydrolysable zirconate or a hydrolysable aluminate, having more than 2 hydrolysable groups per molecule (e.g. a zirconium tetraalkoxide or a titanium tetraalkoxide or an aluminium trialkoxide) or some other crosslinkable species, or it may be a mixture of any two or more of the above. The crosslinkable species may be the precursor, or the crosslinkable species may react in the presence of water to form the precursor. For example the crosslinkable species may at least partially hydrolyse, and may also partially crosslink, to form the precursor. Thus the precursor may comprise partial hydrolysates, complete hydrolysates or partial condensates (e.g. dimers, trimers, tetramers etc.) of the crosslinkable species, or may comprise a mixture of these. The ratio of water to the crosslinkable species in the second mixture used in forming the hydrophilic phase may be between about 1:1 and about 5:1, or between about 1:1 and 4:1, 1:1 and 3:1, 2:1 and 5:1, 2:1 and 4:1, 3:1 and 5:1 or 1.5:1 and 2.5:1, and may be about 1:1, 1.5:1, 2:1, 2.5:1, 3:1, 3.5:1, 4:1, 4.5:1 or 5:1, or may be some other ratio. The first mixture (comprising first surfactant, hydrophobic phase and water) may be combined with the second mixture in a ratio of between about 1:1 and about 1:5 on a weight or volume basis (or between about 1:2 and 1:5, 1:3 and 1:5, 1:1 and 1:3, 1:1 and 1:4 or 1:2 and 1:4 and may be about 1:1, 1:1.5, 1:2, 1:2.5, 1:3, 1:3.5, 1:4, 1:4.5 or 1:5, or some other ratio) in the production of the first emulsion, which may have a ratio of water to the hydrolysable species may be between about 2:1 and 10:1 on a molar basis (or between about 2:1 and 5:1, 2:1 and 4:1, 3:1 and 10:1, 3:1 and 6:1, 3:1 and 5:1, 5:1 and 10:1, 2:1 and 5:1, or about 2:1, 3:1, 4:1, 5:1, 6:1, 7:1 8:1, 9:1 or 10:1 or some other ratio. A catalyst, e.g. $H^+$ may be required to catalyse formation of the precursor. This may be supplied by any convenient acid, such as sulfuric, nitric or hydrochloric acid. The pH required for formation of the precursor may be between about 1 and 5, or between about 1 and 4, 1 and 3, 2 and 5, 2 and 4 or 3 and 5, and may be about 1, 2, 3, 4 or 5. Even stronger acid may be used, for example the acid may be between about 0.01 and about 2M, or between about 0.01 and 1, 0.01 and 0.5, 0.01 and 0.1, 0.1 and 2, 0.5 and 2, 1 and 2, and may be about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5 or 2M or may be more than about 2M.

The time required for the formation of the precursor may be between about 1 minute and about 48 hours, or between about 5 minutes and 24 hours, 5 minutes and 12 hours, 5 minutes and 6 hours, 5 minutes and 1 hour, 5 and 30 minutes, 5 and 15 minutes, 1 and 48 hours, 12 and 48 hours, 24 and 48 hours, 36 and 48 hours, 1 and 36 hours, 6 and 30 hours, 12 and 30 hours, 18 and 30 hours, 20 and 28 hours, 22 and 26 hours, 1 and 12 hours, 1 and 6 hours, 30 minutes and 1 hour, 30 minutes and 5 hours, 1 and 5 hours, 2 and 5 hours, 3 and 5 hours, 1 and 4 hours, 1 and 3 hours, 1 and 2 hours or 30 minutes and 2 hours and may be about 5, 10, 15, 20, 25, 30, 35, 40, 45, 50 or 50 minutes, or about 1, 2, 3, 4, 5, 6, 9, 12, 15, 18, 21, 24, 30, 36, 42 or 48 hours, and may be about 10, 20, 30, 40 or 50 minutes, or about 1, 1.5, 2, 2.5, 3, 3.5, 4, 4.5 or 5 hours or more than 5 hours. The temperature for said formation may be between about 0 and about 80° C., or between about 0 and 60, 0 and 40, 0 and 20, 0 and 10, 20 and 80, 40 and 80, 60 and 80, 70 and 80, 10 and 50, 10 and 40, 10 and 30, 10 and 20, 20 and 50, 30 and 50 or 20 and 40° C., and may be about 0, 5, 10, 15, 20, 25, 30, 35, 40, 45, 50, 55, 60, 65, 70, 75 or 80° C., or may be more than 80° C. For example at pH 3, the time required may be about 24 hours.

The ratio of the hydrophobic phase to the hydrophilic phase in the first emulsion may be between about 1:1 and about 1:100 on a weight or volume basis, or between about 1:1 and 1:50, 1:1 and 1:10, 1:1 and 1:5, 1:1 and 1:3, 1:10 and 1:100, 1:50 and 1:100, 1:5 and 1:50, 1:10 and 1:50 or 1:10 and 1:20, and may be about 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:60, 1:70, 1:80, 1:90 or 1:100, or may be some other ratio.

The process of forming the first emulsion may comprise combining the hydrophobic phase with water and a first surfactant to form a first mixture. This first mixture is then combined with a second mixture which comprises the precursor and water. The first and second mixtures may then be agitated to form the first emulsion. The agitation may comprise high shear, and may be by high shear mixing, sonication or some other suitable method. In the present invention, various steps of agitation are or may be used. The method employed for these steps is not critical and any commonly used agitation equipment, such as a blade or paddle mixer, mechanical stirrer, magnetic stirrer etc. is suitable. For high shear agitation, a sonicator may also be used.

The agitation may be for between about 1 minute and 1 hour, or between about 1 and 30 minutes, 1 and 20 minutes, 1 and 10 minutes, 5 minutes and 1 hour, 10 minutes and 1 hour, 30 minutes and 1 hour, 10 and 30 minutes or 5 and 20 minutes, and may be for about 1, 2, 3, 4, 5, 6, 7, 8, 9 10, 15, 20, 25, 30, 40 or 50 minutes, or for 1 or more hours. The first mixture may be an emulsion, and may be a microemulsion. It, and independently the first emulsion, may have a mean droplet diameter between about 10 nm and about 50 microns, or between about 10 mm and 10 microns, 10 and 50 microns, 1 and 50 microns, 20 and 50 microns, 10 and 20 microns, 10 nm and 1 micron, or between about 10 and 500, 10 and 200, 10 and 100 or 10 and 50 microns, or between about 50 nm and 10 microns, 100 nm and 10 microns, 500 nm and 10 microns, 1 and 10 microns, 1 and 5 microns, 5 and 10 microns, 50 nm and 5 microns or 100 nm and 1 micron, and may have a mean droplet diameter about 10, 20, 30, 40, 50, 60, 70, 80, 90, 100, 150, 200, 250, 300, 350, 400, 450, 500, 600, 700, 800 or 900 nm, or may have a mean droplet diameter about 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45 or 50 microns, or may have a mean droplet diameter more than about 50 microns. The droplet diameter of the first mixture and the first emulsion may be the same or different. The ratio of the hydrophobic phase to the water in the first mixture may be between about 1:1 and 1:50 on a weight or volume basis, or may be between about 1:1 and 1:20, 1:1 and 1:10, 1:1 and 1:5, 1:5 and 1:50, 1:10 and 1:50, 1:20 and 1:50, 1:5 and 1:20 or 1:10 and 1:20, and may be about 1:1, 1:2, 1:3, 1:4, 1:5, 1:10, 1:15, 1:20, 1:30, 1:40 or 1:50 on a weight or volume basis, or may be some other ratio. The ratio of the hydrophobic phase to the first surfactant may be between about 100:1 and about 1:100 on a weight or volume basis, or between about 100:1 and 1:1, 50:1 and 1:1, 20:1 and 1:1, 10:1 and 1:1, 5:1 and 1:1, 2:1 and 1:1, 50:1 and 1:50, 20:1 and 1:20, 10:1 and 1:10, 5:1 and 1:5, 2:1 and 1:2, 1:2 and 100:1, 1:10 and 1:100, 1:50 and 1:100, 1:2 and 1:50, 1:2 and 1:10, 1:2 and 1:5, 1:5 and 1:50, 1:10 and 1:50, 1:20 and 1:50 or 1:5 and 1:20, and may be about 100:1, 50:1, 20:1, 10:1, 5:1, 2:1, 1:1, 1:2, 1:3, 1:4, 1:5, 1:6, 1:7, 1:8, 1:9, 1:10, 1:15, 1:20, 1:30, 1:40, 1:50, 1:60, 1:70, 1:80, 1:90 or 1:100 on a weight or volume basis, or may be some other ratio. The first surfactant may be a suitable surfactant for forming an oil in water (O/W) emulsion. It may be a high HLB (hydrophilic/lipophilic balance) surfactant, i.e. it may be a hydrophilic surfactant. The HLB of the first surfactant may be between about 8 and 20, or between about 15 and 20, 10 and 15, 13 and 17 or 15 and 18, and may be about 8, 9, 10, 11, 12, 13, 14, 15, 16, 17, 18, 19 or 20, or may be greater than 20. It may be a polysorbate surfactant, and may be for example a Tween (polyoxyethylene derivative of sorbitan ester) Tween 20, Tween 21, Tween 61, Tween 80 or Tween 81 or it may be a PEO/PPO copolymer e.g. Pluronic P123. Other surfactants that may be used include Brij (polyoxyethylene fatty ether), e.g. Brij30, an NP (nonylphenoxypolyethoxyethanol) e.g NP-4, NP-5, NP-6, NP-9, Triton (octylphenoxypolyethoxyethanol), e.g. Triton X-100, Triton X-114, Myrj e.g. Myrj 45. It may be an ionic surfactant e.g. Aerosol OT (docusate sodium salt: bis(2-ethylhexyl) sulfosuccinate sodium salt). The first surfactant may comprise a mixture of different surfactants, and may also comprise a cosurfactant.

The first emulsion may have a catalyst for hydrolysis and/or condensation of the crosslinkable species or of the precursor. The catalyst may be acid or some other catalyst. This may be achieved by incorporating the catalyst into either the first mixture or the second mixture or both. The pH of the first mixture, or of the second mixture, or of the hydrophilic phase of the first emulsion, may, independently, be between about 1 and 10, or between about 2 and 8, 2 and 7, 2 and 6, 2 and 4, 5 and 10, 7 and 10, 8 and 10, 3 and 7, 3 and 6, 3 and 5 or 7 and 9, and may be about 1, 2, 3, 4, 5, 6, 7, 8, 9 or 10, or may be outside the range of about 1 to 10. Even stronger acid may be used, for example the acid may be between about 0.01 and about 2M, or between about 0.01 and 1, 0.01 and 0.5, 0.01 and 0.1, 0.1 and 2, 0.5 and 2, 1 and 2, and may be about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5 or 2M or may be more than about 2M. Alternatively the pH may be between about 7.5 and about 13.5. The pH may be between about 7.5 and 12, 7.5 and 9, 8 and 13.5, 10 and 13.5, 8 and 13, 8 and 12, 8 and 10 or 10 and 12, and may be about 7.5, 8, 8.5, 9, 9.5, 10, 10.5, 11, 11.5, 12, 12.5, 13 or 13.5. The pH may be adjusted to the desired value using an acid, for example hydrochloric, sulfuric, phosphoric, nitric, or some other acid, or using a base, for example sodium hydroxide, potassium hydroxide or ammonia. Alternatively the pH may be adjusted using a buffer, for example a phosphate buffer.

The multiple emulsion is formed by dispersing the first emulsion in a hydrophobic medium. The dispersion may comprise low shear mixing, for example using low shear mixer. The dispersing may be at sufficiently low shear that the first emulsion is not disrupted, i.e. the hydrophobic phase remains dispersed within the hydrophilic phase of the first emulsion. The hydrophobic medium may have the second surfactant dissolved, suspended or dispersed therein. The proportion of the first emulsion in the multiple emulsion may be between about 1 and about 30% by weight or by volume, or between about 1 and 15, 1 and 10, 1 and 5, 10 and 30, 15 and 30, 20 and 30, 25 and 30, 5 and 15, 10 and 15, 2 and 5, 5 and 10 or 7 and 10%, and may be about 1, 1.5, 2, 3, 4, 5, 6, 7, 8, 9, 10, 11, 12, 13, 14, 15, 20, 25 or 30% by weight or by volume. The proportion of the second surfactant in the hydrophobic medium may be between about 1 and about 40% by weight or by volume, and may be between about 1 and 30, 1 and 20, 1 and 10, 1 and 8, 1 and 6, 1 and 4, 3 and 10, 5 and 10, 8 and 10, 2 and 8 or 4 and 6%, and may be about 1, 2, 3, 4, 5, 6, 7, 8, 9, 10, 15, 20, 25, 30, 35 or 40% by weight or by volume. The second surfactant may be a low HLB surfactant, i.e. it may be a hydrophobic surfactant. The HLB of the second surfactant may be between about 1 and 10, or between about 1 and 8, 1 and 5, 2 and 5 or 3 and 7, and may be about 1, 2, 3, 4, 5, 6, 7, 8, 9 or 10. The second surfactant may be a sorbitan ester, for example span 80 (sorbitan monooleate, HLB 4.3), glycerol monooleate (HLB 2.8-3.0), glycerol monostearate (HLB 3.2), PEO/PPO copolymers, sorbitan trioleate (Span 85, HLB 1.8), sorbitan tristearate (Span 65, HLB 2.1) or sorbitan sesquioleate (HLB 4), or sorbitan monolaurate (Span 20, HLB 8.6), or sorbitan monopalmitate (Span 40, HLB 6.7), or sorbitan monostearate (Span 60, HLB 4.7). The second surfactant may comprise a mixture of surfactants, and may also comprise a cosurfactant. A neutral polymer may also be used to increase the viscosity of the hydrophobic medium. The hydrophobic medium may be any suitable hydrophobic liquid. It may be the same as or different to the hydrophobic diluent. It may be for example a liquid hydrocarbon (e.g. pentane, hexane, heptane, octane, decane, cyclohexane, benzene, toluene, xylene), a chlorinated solvent (e.g. chlorobenzene, dichlorobenzene, chloroform, dichloromethane, carbon tetrachloride, ethylene dichloride, dichloroethane, methyl chloroform), and ester (e.g. ethyl acetate), an ether (e.g. diethyl ether) or some other hydrophobic liquid. The droplets of first emulsion in the multiple emulsion may have a mean diameter between about 0.1 and 1000 microns, or between about 0.1 and 0.5, 0.1 and 10, 0.1 and 100, 0.1 and 500, 0.1 and 800, 500 and 1000, 500 and 800, 1 and 1000, 10 and 1000, 100 and 1000, 10 and 800, 100 and 800, 0.5 and 100, 0.5 and 50, 0.5 and 10, 0.5 and 5, 1 and 250, 10 and 250, 100 and 250, 10 and 100, 10 and 50, 250 and 500, 100 and 500 or 50 and 500 microns, and may have a mean diameter of about 0.1, 0.2, 0.3, 0.4, 0.5, 1, 2, 3, 4, 5, 6, 7, 8, 9, 01, 15, 20, 25, 30, 35, 40, 45, 50, 60, 70, 80, 90, 100, 125, 150, 175, 200, 225, 250, 300, 350, 400, 450, 500, 550, 600, 650, 700, 750, 800, 850, 900, 950 or 1000 microns, or may be larger than about 1000 microns.

The process of the present invention may comprise several steps which comprise dispersing and/or agitating. Each of said steps may, independently, comprise mild or vigorous agitation. They may, independently, comprise stirring, swirling, shaking, sonicating, ultrasonicating or some other manner of agitating, or may comprise a combination of these. As noted earlier, formation of the multiple emulsion should be at sufficiently low shear that the first emulsion is not disrupted.

Following formation of the multiple emulsion, the precursor is allowed to react to form the particles having the hydrophobic material therein, said particles being dispersed in the hydrophobic medium. The step of reacting may comprise ageing the multiple emulsion. The ageing may be for sufficient time to form the particles, and may be for example for between about 1 minute and 50 hours. It may be for between 5 and 10 minutes, 10 minutes and 5 hours, 10 minutes and 1 hour, 10 and 50 minutes, 10 and 40 minutes, 10 and 30 minutes, 10 and 20 minutes, 15 and 30 minutes, 30 minutes and 10 hours, 1 and 10 hours, 5 and 10 hours, 30 minutes and 5 hours or 30 minutes and 1 hour, and may be for about 5, 10, 15, 20, 25, 30, 35, 40, 45, 50 or 55 minutes, or for about 1, 1.5, 2, 2.5, 3, 3.5, 4, 4.5, 5, 6, 7, 8, 9, 10, 12, 15, 18, 24, 27, 30, 33, 36, 42, 48 or 50 hours, or may be for more than 50 hours. The sufficient time may depend on the pH of the first emulsion. For example ageing for about 1 hour may be sufficient at pH 2 whereas ageing for about 24 hours may be required at pH 3. As noted earlier, the reaction of the precursor to form the matrix may continue after the particles have been separated from the hydrophobic phase. The sufficient time may depend on the temperature of ageing, the nature and quantity of the catalyst and on the nature of the precursor. The ageing may be at any convenient temperature at which the hydrophobic material is stable over the sufficient time, and may be between about 10 and 60° C. It may be at between about 10 and 50, 10 and 40, 10 and 30, 10 and 20, 20 and 60, 40 and 60, 10 and 30 or 15 and 30° C., and may be at about 10, 15, 20, 25, 30, 35, 40, 45, 50, 55 or 60° C., or at some other temperature. During said ageing, the multiple emulsion may or may not be agitated. The hydrophobic material in the particles may be releasable from the particles.

The step of reacting the precursor may depend on the nature of the precursor. As noted above, for precursors that solidify by a hydrolysis/condensation mechanism (e.g. silane derived precursors), this may comprise ageing, and optionally heating. However for different precursors the step of allowing the precursor to solidify may comprise any or all of providing a solidification reagent to the precursor, exposing the multiple emulsion to radiation (e.g. UV radiation, gamma radiation) or some other process for causing reacting the precursor to form the matrix.

The process may additionally comprise one or more of the steps of at least partially separating the particles from the hydrophobic medium, ageing the particles, washing the particles, and drying the particles. After the particles have been formed, they may be hardened. This may be performed before or after separating the particles from the hydrophobic medium. It may take between about 1 and about 10 hours, or between 1 and 5, 1 and 2, 2 and 5, 2 and 10, 1 and 3, 1.5 and 2.5 or 5 and 10 hours, and may take about 1, 1.5, 2, 2.5, 3, 3.5, 4, 4.5, 5, 5.5, 6, 6.5, 7, 7.5, 8, 8.5, 9, 9.5 or 10 hours or more than 10 hours. Alternatively it may take less than 1 hour, depending on the conditions and the chemistry. It may take, for example between about 10 minutes and about 1 hour, or between 10 and 50 minutes, or about 10 and 40, 10 and 30, 10 and 20, 20 and 50, 20 and 30 or 15 and 25 minutes, and may take about 10, 15, 20, 25, 30, 35, 40, 45, 50 or 55 minutes. It may comprise maintaining the particles at a temperature sufficient to harden the particles. The temperature may be sufficiently low as to not cause degradation, volatilisation or deterioration of the hydrophobic material. The temperature may be between about 0 and about 100° C., or between about 0 and 80, 0 and 60, 0 and 40, 0 and 20, 0 and 10, 20 and 100, 40 and 100, 60 and 100, 80 and 100, 60 and 100, 80 and 100, 20 and 80, 40 and 80 or 40 and 60° C., and may be about 0, 5, 10, 15, 20, 25, 30, 35, 40, 45, 50, 55, 60, 65, 70, 75, 80, 85, 90, 95 or 100° C. The temperature and time may be sufficient that the particles do not shatter, rupture, break or crush during washing and drying. The step of separating may comprise settling, decanting, filtering, centrifuging, distilling or some other method. After the step of at least partially separating, the particles may be further aged. This may be for a suitable period for further reaction of the precursor. It may be for example be between about 1 hour and about 24 hours or more, or for between about 1 and 12, 1 and 6, 6 and 24, 12 and 24 or 18 and 24 hours. The temperature of further aging may be between about 0 and about 100° C., or between about 0 and 80, 0 and 60, 0 and 40, 0 and 20, 0 and 10, 20 and 100, 40 and 100, 60 and 100, 80 and 100, 20 and 80, 40 and 80 or 40 and 60° C., and may be about 0, 5, 10, 15, 20, 25, 30, 35, 40, 45, 50, 55, 60, 65, 70, 75, 80, 85, 90, 95 or 100° C. The temperature may be sufficiently low as to not cause degradation, volatilisation or deterioration of the hydrophobic material. The step of washing may be with a solvent. The solvent may be hydrophilic or hydrophobic. It may be for example water, an aqueous solution (e.g. salt solution, such as sodium chloride solution), methanol, ethanol, propanol, isopropanol, hexane, chloroform, cyclohexane, and may be any of the solvents described earlier for use as a hydrophobic medium, or it may be a mixture of any two or more of these solvents. One has to be cautious not to use a solvent that will leach the hydrophobic active out of the particles and thus decrease the encapsulation efficiency. In particular, the solvent is one which does not leach or does not substantially leach the hydrophobic active out of the particles. The expression "does not substantially leach the hydrophobic active out of the particles" includes where less than 30 wt %, 25 wt %, 20 wt %, 15 wt %, 10 wt %, 5 wt %, 4 wt %, 3 wt %, 2 wt %, 1 wt %, 0.5 wt %, 0.25 wt % or 0.1 wt % of the hydrophobic active is leached out of the particles (wt % being a weight percentage of the total weight of the hydrophobic active in the particles). The expression "does not substantially leach the hydrophobic active out of the particles" includes where between 30 wt % and 0.001 wt %, 25 wt % and 0.01 wt %, 20 wt % and 0.01 wt %, 15 wt % and 0.01 wt %, 10 wt % and 0.01 wt %, 5 wt % and 0.01 wt %, 4 wt % and 0.01 wt %, 3 wt % and 0.01 wt %, 2 wt % and 0.01 wt %, 1 wt % and 0.01 wt %, 0.5 wt % and 0.01 wt %, 0.25 wt % and 0.01 wt % or 0.1 wt % and 0.01 wt % of the hydrophobic active is leached out of the particles (wt % being a weight percentage of the total weight of the hydrophobic active in the particles). The step of washing may comprise combining the particles with the solvent, optionally agitating the particles and solvent, and then removing the solvent. The step of washing may comprise passing the solvent through the particles. The passing may be conducted under gravity, or under vacuum. It may for example be conducted using a Büchner funnel or a sintered glass filter funnel. The step of washing may if appropriate also comprise separating the particles from the solvent. This may be performed as described above for separating the particles from the hydrophobic medium. The step of washing may be repeated between about 1 and 10 times, and each step of washing may use the same solvent or a different solvent to any other step of washing.

The step of drying may comprise heating the particles. The heating may be to a temperature below the temperature at which the hydrophobic material decomposes or deteriorates, or substantially volatilises (this may be an issue if the hydrophobic material is volatile) and may be for example between about 30 and 80° C., or between about 30 and 60, 30 and 40, 40 and 80, 60 and 80 or 40 and 60° C., and may be about 30, 35, 40, 45, 50, 55, 60, 65, 70, 75 or 80° C. Alternatively or additionally the step of drying may comprise freeze-drying, for example as described in WO01/62332 (Barbé and Bartlett, "Controlled Release Ceramic Particles, Compositions thereof, Processes of Preparation and Methods of Use"). The step of drying may additionally or alternatively comprise passing a stream of gas over and/or through the particles. The gas may be a gas that is inert to the particles and to the hydrophobic material, and may be for example air, nitrogen, argon, helium, carbon dioxide or a mixture of these, and may be dried. The step of drying may additionally or alternatively comprise applying a partial vacuum to the particles. The partial vacuum may have an absolute pressure of for example between about 0.01 and 0.5 atmospheres, or between about 0.01 and 0.1, 0.01 and 0.05, 0.1 and 0.5, 0.25 and 0.5, 0.05 and 0.1 or 0.1 and 0.25 atmospheres, and may have an absolute pressure of about 0.01, 0.05, 0.1, 0.2, 0.3, 0.4 or 0.5 atmospheres. The drying may comprise vacuum drying or freeze drying. The vacuum drying may be at any suitable vacuum that does not substantially remove the hydrophobic material. It may be for example between about 0.01 and 0.5 atm (absolute pressure), or between about 0.01 and 0.1, 0.01 and 0.05, 0.1 and 0.5, 0.1 and 0:3 atm, and may be about 0.01, 0.05, 0.1, 0.2, 0.3, 0.4 or 0.5 atm.

The encapsulation efficiency of the process (i.e. the proportion of hydrophobic material used in the process that is incorporated into the particles) may depend on the conditions used in the process and the means for measuring the efficiency. The encapsulation efficiency may be measured by a direct method, i.e. by extracting the hydrophobic material and quantifying it by for example HPLC or UV spectroscopy, or by an indirect method by measuring the amount of hydrophobic material that is not incorporated (e.g. by UV spectroscopy) and determining the encapsulation efficiency from the amount not incorporated and the amount used in the process. The process may provide an encapsulation efficiency of between about 5 and 75%, or between about 5 and 50, 5 and 25, 5 and 10, 10 and 75, 25 and 75, 50 and 75, 10 and 50, 30 and 50 or 20 and 40%, and may provide an encapsulation efficiency of about 5, 10, 15, 20, 25, 30, 35, 40, 45, 50, 55, 60, 65, 70 or 75%. The encapsulation efficiency may depend on the nature of the hydrophobic material, for example the size of the molecules of the hydrophobic material and the hydrophobicity of the hydrophobic material. For example under identical conditions, limonene (MW136) was incorporated with a lower efficiency than Solvent Blue-35 dye (SB-35: MW350). It may also depend on the nature of the precursor or the mixed precursor. It may depend on the nature of the catalyst and the synthesis parameters, etc.

The features described throughout the specification or claims for the process of the invention may be present in any workable combination of process steps.

The particles of the present invention have a hydrophobic material immobilised therein. The hydrophobic material in the particles may be releasable from the particles. The hydrophobic material in the particles may be releasable from the particles in a controlled rate over a period of time. An earlier method for making ceramic particles by use of O/W/O double emulsions required that the double emulsions be stable. This method generated a double emulsion having a hydrophobic material therein. In a separate step, a hydrolysable silane was added to the double emulsion. The silane was thought to penetrate to the aqueous emulsion droplets, where it could hydrolyse to form a ceramic material. It is known that double emulsions are difficult to make and are in many cases of limited stability. Addition of species such as the silane may in some cases induce instability in the emulsion. To combat any instability, earlier workers have incorporated thickening agents in the double emulsion. This has the potential to complicate the synthesis of the particles, and/or to incorporate the thickening agent into the particles. If it is incorporated, the thickening agent may be released at a later date, which may be undesirable, particularly in applications where the particles are used to deliver the hydrophobic material to a human patient. The present process avoids the use of thickening agents by employing a process that requires only short term stability of the double emulsion. Accordingly, the particles of the present invention may be made by a process that does not comprise use of a thickening agent. The particle may accordingly have no thickening agent therein or thereon. Accordingly, when formed, the double emulsion of the present invention may be stable, metastable, unstable or partially stable. It may be sufficiently stable that the precursor has time to react to form a non-fluid matrix during the period of stability of the double emulsion. Thus the period of stability of the double emulsion may be greater than the reaction time of the precursor to form the non-fluid matrix. The stability of the double emulsion may be enhanced by agitation. The agitation may comprise stirring, shaking or other agitation. It may be mild agitation. It may be sufficiently mild agitation that the double emulsion is stable for sufficient time for the precursor to react to form the particles having the hydrophobic material therein.

The hydrophobic material may be immobilised in the particle in a plurality of discrete compartments. The hydrophobic material in the particles may be releasable from the particles. The particle may have between about 10 and about $10^{10}$ discrete compartments, or between about $10^6$ and about $10^{10}$ discrete compartments or it may have more than $10^{10}$ discrete compartments. The particle may have between about 100 and $10^{10}$, $10^4$ and $10^{10}$, $10^6$ and $10^{10}$, $10^8$ and $10^{10}$, 100 and $10^9$, 100 and $10^8$, 100 and $10^7$, $10^4$ and $10^9$, $10^6$ and $10^9$, $10^4$ and $10^8$, $10^6$ and $10^8$, $10^6$ and $10^8$ or $10^7$ and $10^9$, and may have about 100, 1000, $10^4$, $5*10^4$, $10^5$, $5*10^5$, $10^6$, $5*10^6$, $10^7$, $5*10^7$, $10^8$, $5*10^8$, $10^9$, $5*10^9$ or $10^{10}$ discrete compartments. The compartments may be spherical, or they may be cylindrical, prismatic, polyhedral (with between about 4 and 20 sides), ellipsoid, ovoid, bullet-shaped or some other shape. The shape may be regular or irregular. The discrete compartments may have a mean diameter between about 10 nm and about 50 microns, or between about 10 nm and 10 microns, 10 and 50 microns, 1 and 50 microns, 20 and 50 microns, 10 and 20 microns, 10 nm and 1 micron, or between about 10 and 500 nm, 10 and 200, 10 and 100 or 10 and 50 nm, or between about 50 nm and 10 microns, 100 nm and 10 microns, 500 nm and 10 microns, 1 and 10 microns, 1 and 5 microns, 5 and 10 microns, 50 nm and 5 microns or 100 nm and 1 micron, and may have a mean diameter about 10, 20, 30, 40, 50, 60, 70, 80, 90, 100, 150, 200, 250, 300, 350, 400, 450, 500, 600, 700, 800 or 900 nm, or may have a mean diameter about 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45 or 50 microns, or may have a mean diameter more than 50 microns. The discrete compartments may have a monodispersed diameter or a polydispersed diameter, and may have narrow or broad distribution. The particles may have a mean particle diameter between about 0.1 and about 1000 microns, or between about 0.1 and 0.5, 0.1 and 10, 0.1 and 100, 0.1 and 500, 0.1 and 800, 0.5 and 100, 0.5 and 50, 0.5 and 10, 0.5 and 5, 1 and 250, 10 and 250, 100 and 250, 10 and 100, 10 and 50, 250 and 500, 100 and 500, 100 and 800, 100 and 1000, 500 and 1000, 500 and 800 or 50 and 500 microns, and may have a mean particle diameter of about 0.1, 0.2, 0.3, 0.4, 0.5, 1, 2, 3, 4, 5, 6, 7, 8, 9, 01, 15, 20, 25, 30, 35, 40, 45, 50, 60, 70, 80, 90, 100, 125, 150, 175, 200, 225, 250, 300, 350, 400, 450, 500, 600, 700, 800, 900 or 1000 microns, or may be larger than about 1000 microns. The particle size distribution may be monodispersed diameter or polydispersed, and may have narrow or broad distribution.

The particle may comprise a crosslinked silane, silica, crosslinked zirconium species, zirconia, crosslinked titanium species, titania, crosslinked aluminium species, alumina, or a hybrid species formed from co-crosslinking at least two species selected from a crosslinkable silane, a crosslinkable titanium species, a crosslinkable zirconium species and a crosslinkable aluminium species. It may comprise a hybrid ceramic comprising at least two of silicon, zirconium, titanium and aluminium, for example an aluminosilicate, a zircoiosilicate or a titanosilicate. The particle may be spherical or it may be cylindrical, prismatic, polyhedral (with between about 4 and 20 sides), ellipsoid, ovoid, bullet-shaped or some other shape. The shape may be regular or irregular. The hydrophobic material in the particles may be releasable from the particles.

The loading of the hydrophobic material in the particle may be between about 0.1 and about 50% by weight or by volume, or between about 0.1 and 30, 0.1 and 20, 0.1 and 10, 0.1 and 5, 0.1 and 1, 0.1 and 0.5, 1 and 50, 5 and 50, 10 and 50, 20 and 50, 0.5 and 20, 0.5 and 5, 0.5 and 1, 1 and 10 or 1 and 5, and may be about 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45 or 50% by weight or by volume. The particle may be capable of releasing the hydrophobic material, and may be capable of releasing the hydrophobic material over a period of time. It may be capable of releasing the hydrophobic material with a half-release time of between about 10 minutes and about 12 months, or between about 10 minutes and 6 months, 10 minutes and 3 months, 10 minutes and 1 month, 10 minutes and 20 days, 10 minutes and 10 days, 10 minutes and 1 day, 10 minutes and 12 hours, 10 minutes and 6 hours, 10 minutes and 1 hour, 10 and 30 minutes, 1 hour and 20 days, 12 hours and 20 days, 1 and 20 days, 5 and 20 days, 10 and 20 days, 1 hour and 2 days, 1 hour and 1 day, 1 and 12 hours, 1 and 6 hours, 6 hours and 1 day, 12 hours and 1 day, 30 minutes and 1 hour or 1 and 10 days, or days and 12 months, 1 and 12 months, 6 and 12 months, 1 and 6 months, 1 and 3 months, 1 day and 1 month or 10 days and 1 month, and may be capable of releasing the hydrophobic material with a half-release time of about 10, 20, 30, 40 or 50 minutes, 1, 2, 3, 4, 5, 6, 9, 12, 15 or 18 hours, or about 1, 1.5, 2, 2.5, 3, 3.5, 4, 4.5, 5, 6, 7, 8, 9, 10, 11, 12, 13, 14, 1, 5 16, 17, 18, 19, 20, 25 or 30 days, or about 1, 2, 3, 4, 5 or 6 months or more than about 6 months. The particle may be capable of releasing the hydrophobic material at a controlled rate. The rate may depend on the internal structure of the silica matrix, which may depend on the sol-gel chemistry parameters and on the oil/water emulsion parameters (nature and concentration of the surfactant, oil/water/surfactant molar ratio). The rate may depend on the size of the particle, the synthesis conditions of the particles such as pH, the temperature, the nature of the medium in which the particle is immersed and/or other factors. The encapsulation efficiency and loading may depend on the size of the internal compartments. The features described throughout the specification or claims for the particles of the invention may be present in the particles in any workable combination of features.

The particles of the present invention may be used for treating a condition in a subject by administering to the subject a therapeutically effective quantity of the particles, wherein the hydrophobic material of the particles is releasable from said particles and is indicated for the condition. The subject may be a vertebrate, and the vertebrate may be a mammal, a marsupial or a reptile. The mammal may be a primate or non-human primate or other non-human mammal. The mammal may be selected from the group consisting of human, non-human primate, equine, murine, bovine, leporine, ovine, caprine, feline and canine. The mammal may be selected from a human, horse, cattle, cow, bull, ox, buffalo, sheep, dog, cat, goat, llama, rabbit, ape, monkey and a camel, for example. The hydrophobic material may be a drug, and the drug may be an anti-cancer drug. The condition may be a disease. The condition may be for example cancer, diabetes, hormonal disjunction, hypertension, pain or some other condition. The particles may be administered by injection (intravenously or intramuscularly), orally, by inhalation, topically or by any other suitable means.

The particles of the present invention may be used for delivering a hydrophobic material. This may comprise exposing the particles according to the present invention to a medium capable of releasing the hydrophobic material encapsulated or immobilised therein. The hydrophobic material should be releasably encapsulated or immobilised. The exposing may comprise immersing the particles in the medium, and may additionally comprise one or more of stirring, shaking, swirling or otherwise agitating the medium having the particles therein. The medium should be capable of releasing or extracting the hydrophobic material from the particles, and may be capable of dissolving the hydrophobic material. The releasing or extracting may be over an extended period of time, as described earlier.

Alternatively the exposing may comprise passing the medium past and/or through the particles. The medium may be a fluid, and may be a liquid. The medium may be a biological fluid such as blood. It may be an organic fluid, and may be an organic solvent, for example a hydrophobic solvent. It may be for example water, methanol, ethanol, propanol, isopropanol, a liquid hydrocarbon (e.g. pentane, hexane, heptane, octane, decane, cyclohexane, benzene, toluene, xylene), a chlorinated solvent (e.g. chlorobenzene, dichlorobenzene, chloroform, dichloromethane, carbon tetrachloride, ethylene dichloride, dichloroethane, methyl chloroform), an ester (e.g. ethyl acetate), an ether (e.g. diethyl ether) or some other hydrophobic liquid. The medium may be capable of dissolving or releasing the hydrophobic material. The hydrophobic material may be for example a fluorescent dye, a radiopharmaceutical, a drug, an enzyme, a hormone, a biocide, a flavour, an aroma substance or some other substance, or it may be a mixture of any two or more of these. The medium may be a gas, for example air, nitrogen, oxygen, helium, argon, carbon dioxide, or a mixture of gases, and the hydrophobic material may be volatile (for example an aroma material). The exposing may be under conditions suitable for release of the hydrophobic material into the medium, for example conditions of temperature, pressure, ratio of particles to the medium etc.

The features described throughout the specification or claims for the method of the invention may be present in any workable combination of method steps.

The particles may be in the form of a composition together with an acceptable carrier, diluent, excipient and/or adjuvant. Where the hydrophobic material is a pharmaceutical substance the carrier may be a pharmaceutically acceptable carrier and the particles may be pharmaceutically acceptable, where the hydrophobic material is a veterinary substance the carrier may be a veterinarilly acceptable carrier and the particles may be veterinarilly acceptable, where the hydrophobic material is a biocidal substance the carrier may be a biocidally acceptable carrier and the particles may be biocidally acceptable, where the hydrophobic material is a pesticidal substance the carrier may be a pesticidally acceptable carrier and the particles may be pesticidally acceptable, where the hydrophobic material is a cosmetic substance the carrier may be a cosmetically acceptable carrier and the particles may be cosmetically acceptable, where the hydrophobic material is a herbicide substance the carrier may be a herbicidally acceptable carrier and the particles may be herbicidally acceptable, where the hydrophobic material is a agaricide substance the carrier may be a agaricidally acceptable carrier and the particles may be agaridally acceptable, and where the hydrophobic material is a fungicidal substance the carrier may be a fungicidally acceptable carrier and the particles may be fungicidally acceptable.

The invention will now be described by way of the following non-limiting examples.

EXAMPLES

Materials

All surfactants and polymers (Table 1) were purchased from Sigma-Aldrich and used without further purification. Silicon precursors such as tetramethoxysilane (TMOS), tetraethoxysilane (TEOS), methyltrimethoxysilane (MTMS), phenyltrimethoxysilane (PTMS), vinyltrimethoxysilane (VTMS), and aminopropyltrimethoxysilane (APTMS) were from Sigma-Aldrich and used directly. Cyclohexane and dodecane were ACS spectro photometric grade (99+%) (Sigma). Kerosene (low odour) was from Aldrich with b.p. 175-325° C. and density 0.800 g/cm$^3$. The purity of Solvent Blue-35 was 98% (Aldrich). Limonene was a gift from Quest International. Retinol (95+%) was purchased from Fluka and used directly. All other chemical reagents used were A.R. grade. High purity Milli-Q water (Millipore) was used for all solutions; its resistivity was above 18.2 MΩ cm.

Synthetic Process ("Typical Synthesis Conditions")

The synthesis flow chart is shown in FIG. 1, which displays the experimental procedure for the synthesis of silica microspheres containing hydrophobic molecules, by employing both sol-gel and $O_1/W/O_2$ multiple (or double) emulsion techniques.

1. A silicon precursor such as TMOS is mixed with water in presence of a catalyst (such as H$^+$) and stirred for 1.5 hours inside a sealed vial. The vial is then opened and the mixture is then further stirred for about 1.5 hours to evaporate excess alcohol produced by hydrolysis of the precursor.

2. The internal oil phase (e.g. limonene) is mixed with a hydrophilic surfactant (e.g. Tween 21) and water phase containing the same catalyst as in step 1. The mixture is then stirred magnetically for about 10 minutes to produce the $O_1/W$ emulsion.

3. The pre-hydrolysed sol-gel solution and $O_1/W$ emulsion is then mixed, and the mixture is sonicated by a probe sonicator to generate $O_1/'W'$ emulsion (here 'W' represents a hydrophilic domain).

4. In the meantime, a surfactant solution is formed by mixing the outer oil phase (e.g. cyclohexane) and a hydrophobic surfactant (e.g. Span 80).

5. The $O_1/'W'$ phase (prepared in step 3) is then poured into the above surfactant solution while stirring gently. After the $O_1/'W'$ phase is poured into the outer oil/surfactant phase, a pseudo $O_1/'W'/O_2$ multiple (or double) emulsion is produced, where the 'W' consists of pre-hydrolysed silicon precursor. While the system stirs, the silicon precursor condenses inside the hydrophilic droplets to produce micron-size silica spheres.

6. After stirring in the range of about 5—about 30 minutes, the suspension is filtered using filter paper (Whatman, England). Following ageing of the dry silica spheres for more than 2 hours, the particles are washed three times by 1 mol/L NaCl solution (total volume 500 mL), and then further washed by pure water three times (total volume 500 mL). The product is then dried at room temperature under nitrogen.

A hydrophobic dye (solvent blue-35) was generally dissolved into the internal oil phase (e.g. limonene) as a marker to visually indicate the encapsulation of oil inside the silica matrix. Although the dye was used predominantly as a visual marker for both encapsulation and release; it can be considered as an active in its own right and thus has also been used to demonstrate the performance of the silica particles for controlled encapsulation and release of hydrophobes.

The amount of each component for a typical synthesis is:

Internal oil: limonene (MW 136.23, density 0.8402 g/cm$^3$) 4.404 mmol (0.714 mL) with 1.428 mg solvent blue-35 (SB-35) dissolved in it.

Hydrophilic surfactant: polyoxyethylene(4) sorbitan monolaurate (Tween 21: MW 522, HLB 13.3) 1.1494 mmol (0.600 g).

Water$_{(1)}$ phase: pH=2 HNO$_3$ solution 2.140 g (water: 118.889 mmol).

Silicon precursor: TMOS (MW: 152.22, 98+%, density 1.032 g/cm$^3$) 58.123 mmol (9.028 g).
Water$_{(2)}$ phase: pH=2 HNO$_3$ solution 2.140 g (water: 118.889 mmol).
Hydrophobic surfactant: Span 80 180.00 mmol (77.152 g).
Outer oil phase: cyclohexane 300 mL.

Particle Characterisation

1. Microscope: Prior to filtration, the particles were examined using an optical microscope (Zeiss Axioplan, West Germany). After drying, the particles were further characterised using a scanning electron microscope (SEM). All SEM images were captured using JEOL SEM-6400 with the settings as image mode: secondary electron image; operating voltage of 15 kV; nominal beam setting of 1×10$^{-10}$ Å and working distance of 15 mm.

2. TGA/DTA: The surfactant residue on the particle surface was determined by thermal gravimetric analysis and differential thermal analysis (TGA/DTA). TGA was performed on a Setaram TGA 24, which was heated to 700° C. at a rate of 10° C./min. The amount of bound surfactant was taken as the difference between the wt % loss at 500° C. and the wt % loss at 140° C., since the flash point of Span 80 surfactant is higher than 148.9° C. (Industrial Surfactants (Electronic Handbook) 2002 Edition, edited by Michael and Irene Ash, Synapse Information Resources, Inc.). DTA was performed simultaneously. Two different decomposition reactions were observed; 1) an endothermic reaction associated with the evaporation of water and other volatiles at approximately 100° C. and 2) an exothermic reaction at approximately 300° C.

3. BET: Sorption isotherms: The Brunauer-Emmett-Teller method was used for the determination of specific surface area of silica particles. Nitrogen adsorption isotherms at 77 K of the silica particles sample was measured using a Micromeritics ASAP 2010 volumetric adsorption analyzer. The BET calculation was performed from the adsorption isotherm at 9 points of relative pressure (P/Po), ranging from 0.05 to 0.2. Before measurements, samples were outgassed at 333K for 10 hours in the degas port of the adsorption analyzer.

Encapsulation and Release Rate:

1. The encapsulation efficiency and release rate of the hydrophobic dye were determined by UV/Vis spectroscopy (Cary 50). The encapsulation efficiency was estimated by two methods. The first one was an indirect measurement, which consisted of measuring the U/Vis absorbance of the cyclohexane/Span 80 solutions after the silica particles had been filtered out. The encapsulation efficiency of the dye was calculated by subtracting the dye measured in the outer oil phase from the original dye concentration introduced into the system. A standard calibration curve was generated by adding accurate amounts of dye into the outer oil phase, with identical composition and concentration as the one used for the preparation of the corresponding samples. The second "direct" method consisted of measuring the release of SB-35 from the silica particles in a solvent such as ethanol, cyclohexane or dodecane, until the absorbance was stable. A standard calibration curve was produced by using the identical composition and concentration as the sample release media. (The surfactant content was estimated by the TGA/DTA result). The absorbance was measured at different intervals of time while stirring the product to produce the dye release curve.

2. A HPLC technique was also used to estimate the encapsulation efficiency of oil (limonene). The Waters HPLC unit which was used is composed of a 2487 dual λ absorbance detector, 717 plus autosampler, and 1525 binary pump. The column was a Symmetry® C$_{18}$, 5 μm 4.6×150 mm and the mobile phase was composed of a mixture of methanol:H$_2$O (9:1 v/v) with a flow rate of 0.5 mL/min. The UV/vis detector wavelength was set to 210 nm. 10 μL was injected by the autosampler. The integrated area (valley to valley) of the limonene peak was used for quantitative calculations. The limonene retention time was approximately 13.5 minutes and the detection limit was approximately 0.02 mg limonene per mL of ethanol.

3. FTIR was used to detect the oil (limonene) in the final product. Samples were immersed in known volumes of dodecane and stirred gently using a magnetic stirrer for 3 days. The supernatant was removed by centrifugation (10,000 rpm, 10 minutes), and then filtered through a 0.22 micron PTFE filter to remove any residual fine silica particles before IR analysis. IR absorption spectra were measured using a Nicolet Nexus 8700 spectrometer equipped with a (linearised) liquid-nitrogen-cooled MCT detector. The spectra were collected using a 45 degree ZnSe attenuated total reflectance accessory. Absorption spectra were generated by ratioing to the background spectrum of dodecane alone and consisted of 256 scans at 4 cm$^{-1}$ resolution. Band areas were compared with those of known concentrations of limonene in dodecane.

4. Diffuse reflectance spectra of the retinol-doped silica particles synthesised by double emulsion procedure were measured using a Cary 500 UV/Vis/NIR spectrometer equipped with a Labsphere Biconical Accessory. Samples were measured after diluting to 20 wt % in PTFE powder. Spectra were converted into reflectance units by using the spectrum of PTFE as a reference, and then transformed into Kubelka-Munk units, $F(R)=(1-R)^2/(2R)$.

Figure 2:
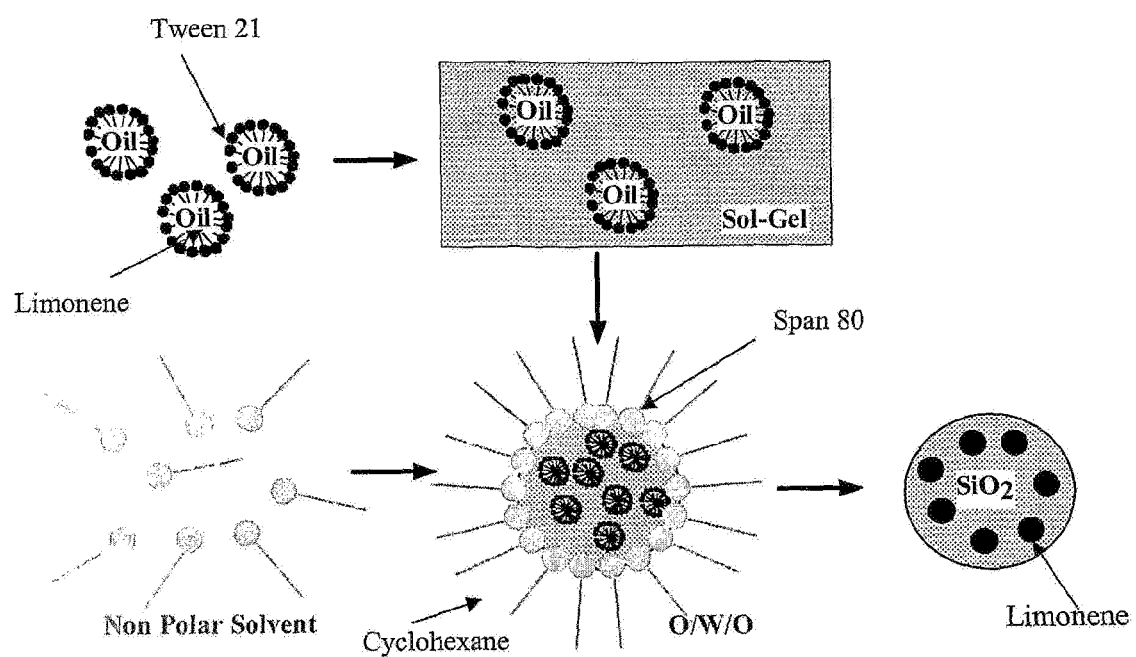
FIG. 2 is a diagram showing a schematic structure of double emulsion droplets according to the present invention during particle synthesis.

Results:

A schematic structure of the double emulsion droplet is presented in FIG. 2, which also shows the variation of emulsion droplets during the synthesis process. Many factors can affect not only the formation of silica particles but also the encapsulation of hydrophobes. Some of these factors have been discussed below.

Figure 3:
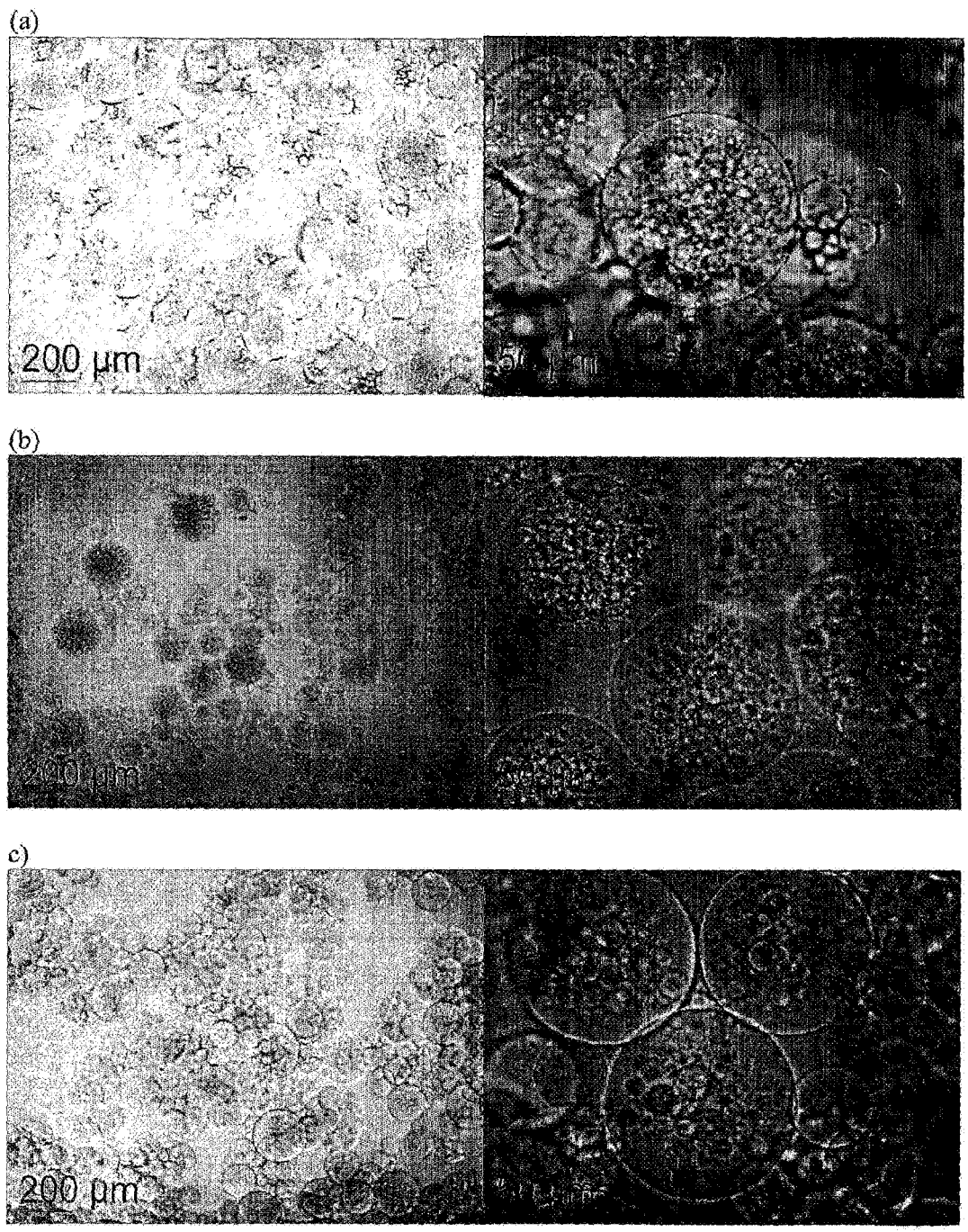
FIG. 3 shows optical micrographs of silica particles according to the present invention, obtained immediately after 20 minutes condensation before filtration, made using Span 80 concentration: (a) 0.26 mol/L, (b) 0.45 mol/L, (c) 0.60 mol/L, (d) 0.75 mol/L and other parameters are same as the typical synthesis conditions described in the examples.
Figure 3:
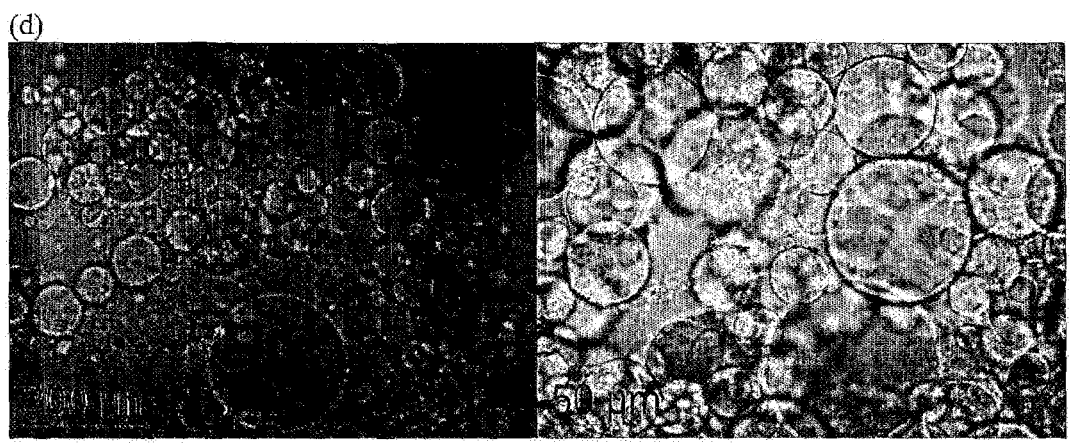

1. Influence of the Hydrophobic Surfactant (Second Surfactant) Concentration Effect on Particle Size A series of samples was synthesised using the synthetic process described above, using an increasing concentration of Span 80. The corresponding optical micrographs are shown in FIG. 3 and the corresponding SEM micrographs can be seen in FIG. 4. From the optical images it is clear that small oil globules in the size of 1 to 10 micron are distributed inside the hydrophilic droplets, which condenses into solid silica particles with ageing. The diameter of these silica particles was in the range of 10-150 μm, and the size distribution became narrower to some extent with increasing Span 80 concentration. The typical morphology of internal structure of a particle is displayed in FIG. 5. The results show that all products contain SB-35 inside and the encapsulation efficiency of dye increases with increasing Span 80 concentration, as observed visually.

This may suggest that increasing the Span 80 concentration not only leads to an increase in the viscosity of the outer oil phase, but also makes the hydrophilic droplets more rigid with multiple layers of surfactant possible rather than monolayer. Consequently, the internal oil may be less likely to diffuse out into the outer oil phase during the formation of the silica network. The size of the internal oil droplets which are distributed inside the silica matrix depends on the energy introduced during the formation of the Oil$_1$/'W' mixture. The more energy is introduced in the system, the smaller the oil droplets. Other variables may also have an influence on the internal oil droplet size. These include internal surfactant type and concentration, internal oil volume fraction, and properties of the hydrophilic domain such as the amount of water, the type of silicon precursor and its concentration, and pH.

2. Influence of the Type and Concentration of the Hydrophilic (First) Surfactant (with Dodecane as Internal Oil Phase)

Figure 6:
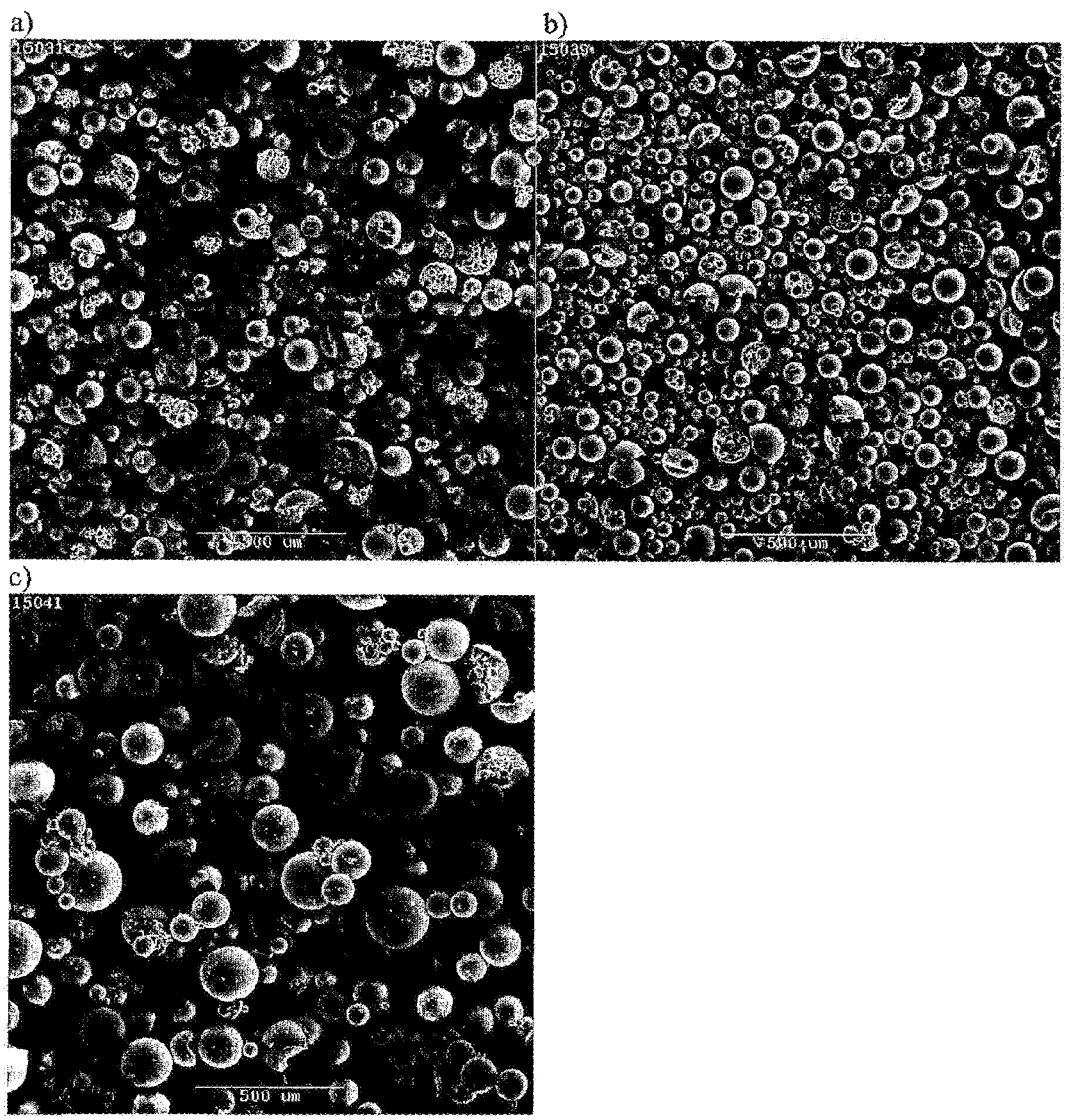
FIG. 6 shows SEM images of silica particles produced using Tween 21: (a) 1.322 mmol; (b) 0.665 mmol; (c) 0.326 mmol, with other experimental conditions being: $Oil_1$ 0.400 mL dodecane with 0.800 mg SB-35 (Solvent Blue 35); $H_2O_{(1)}$ and $H_2O_{(2)}$ 1.068 mL pH 2 $HNO_3$ solution; TMOS 29.650 mmol; $Oil_2$ 225 mL cyclohexane; $Surf_2$ Span 80 58.33 mmol.
Figure 7:
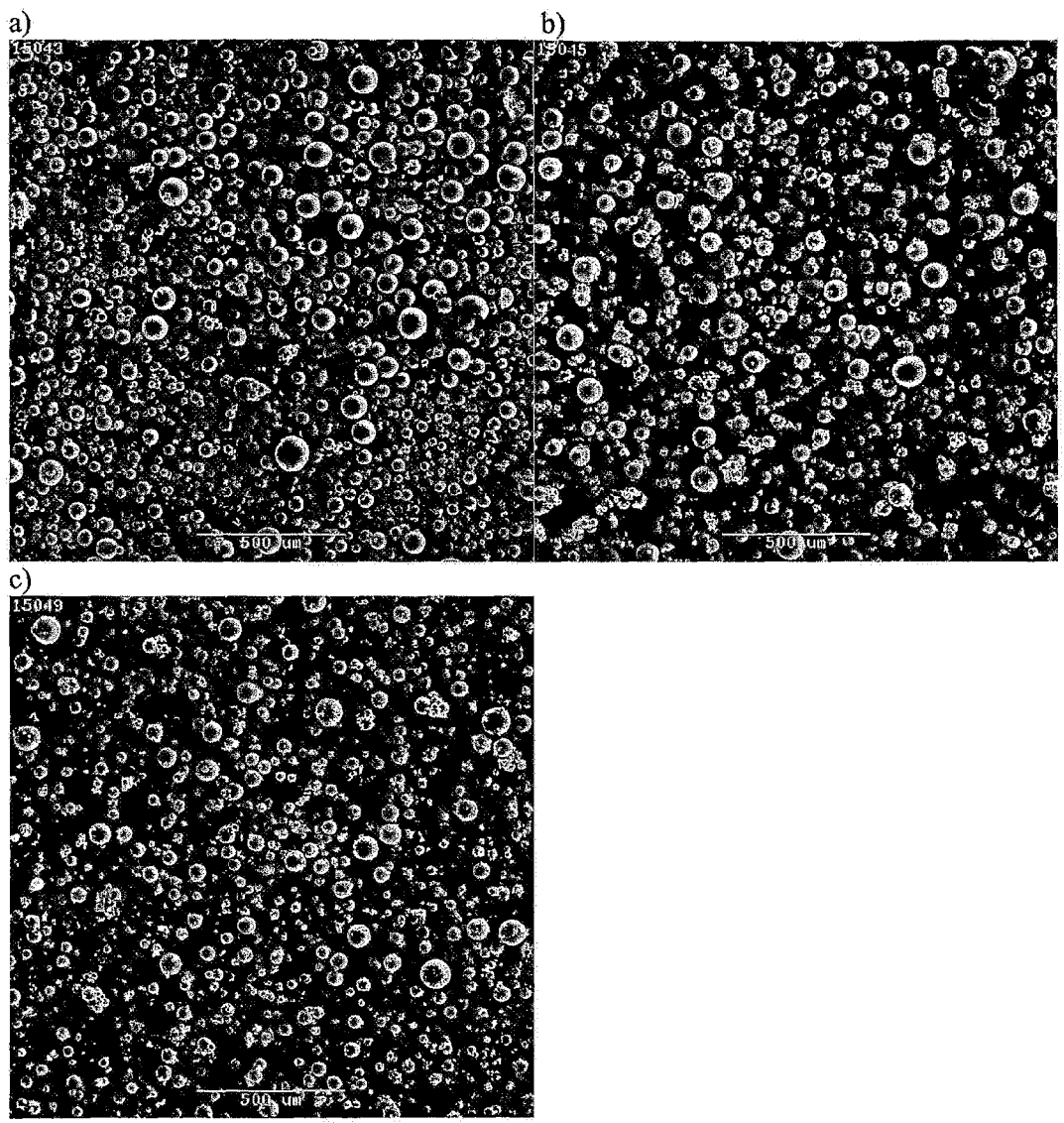
FIG. 7 shows SEM images of silica particles produced using Tween 20: (a) 1.313 mmol, (b) 0.661 mmol, (c) 0.329 mmol, with other experimental conditions as described for FIG. 6.
Figure 8:
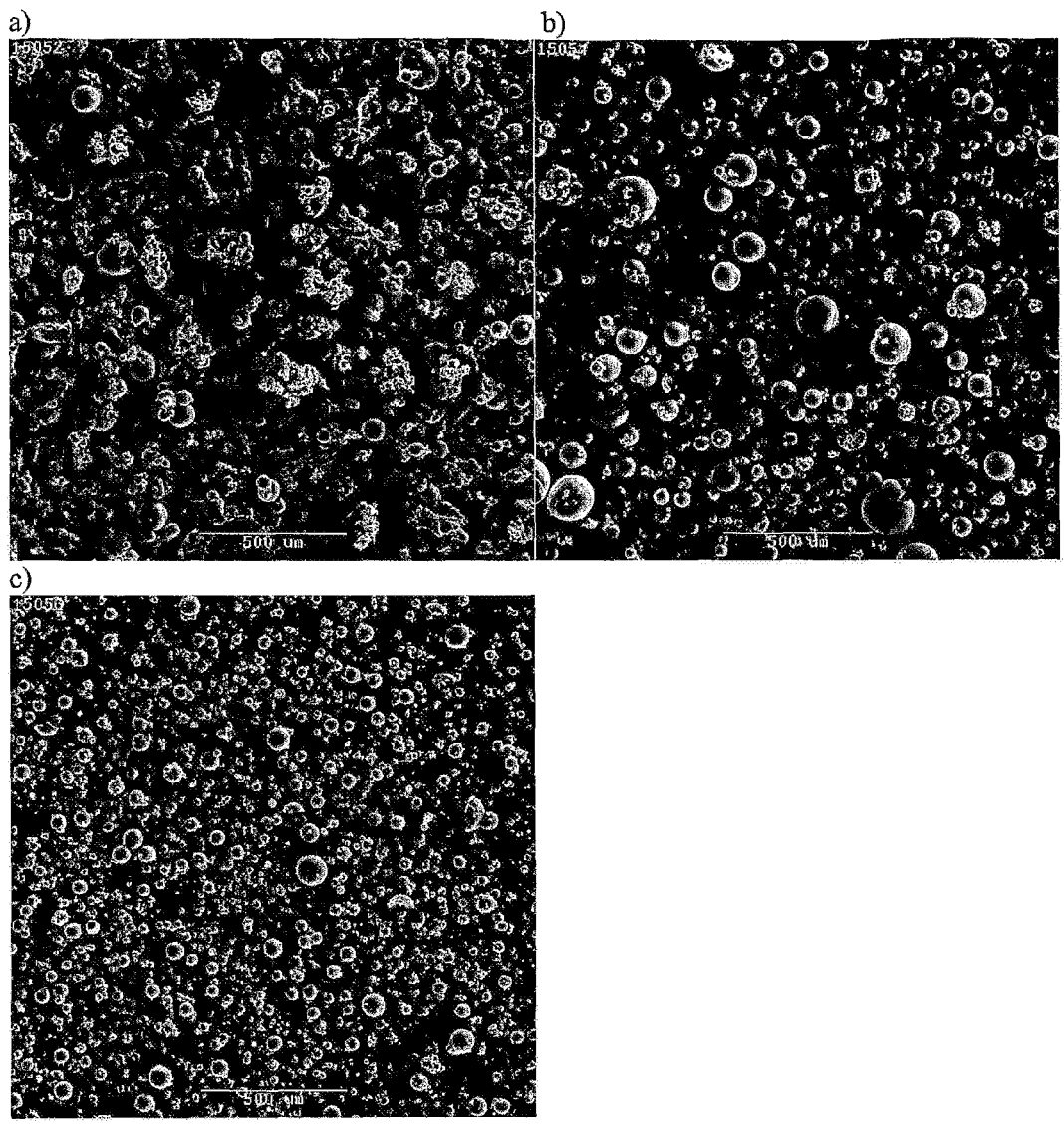
FIG. 8 shows SEM images of silica particles produced using Tween 80: (a) 1.317 mmol, (b) 0.659 mmol, (c) 0.329 mmol, with other experimental conditions as described for FIG. 6.

FIG. 6 shows the SEM images for silica particles prepared at different Tween 21 concentrations, whereas FIGS. 7 and 8 display the SEM results for particles produced by Tween 20 and Tween 80 at various concentrations. The most effective synthesis conditions were obtained for the samples produced using Tween 21, which resulted in the encapsulation of dodecane/SB-35 and a high yield of spherical silica particles. Higher Tween 21 concentrations led to smaller particle size and narrower size distribution. Above approximately 0.6 mmol, no improvement was observed. Particles produced using Tween 20 were smaller in size, but the encapsulation of dodecane/SB-35 was low, whereas particles formed using Tween 80 were more polydispersed, with irregular shapes, especially at higher surfactant concentration. It can be seen from the molecular structure of these surfactants (shown later) that Tween 21 is significantly different from the other two. Tween 21 has only four ethylene oxide units, while Tween 20 and Tween 80 each have 20 ethylene oxide units. This difference in structure, together which with a significant difference in HLB, may explain their significant influence on both the particle formation and oil encapsulation.

3. Influence of the Water to TMOS Molar Ratio

Figure 9:
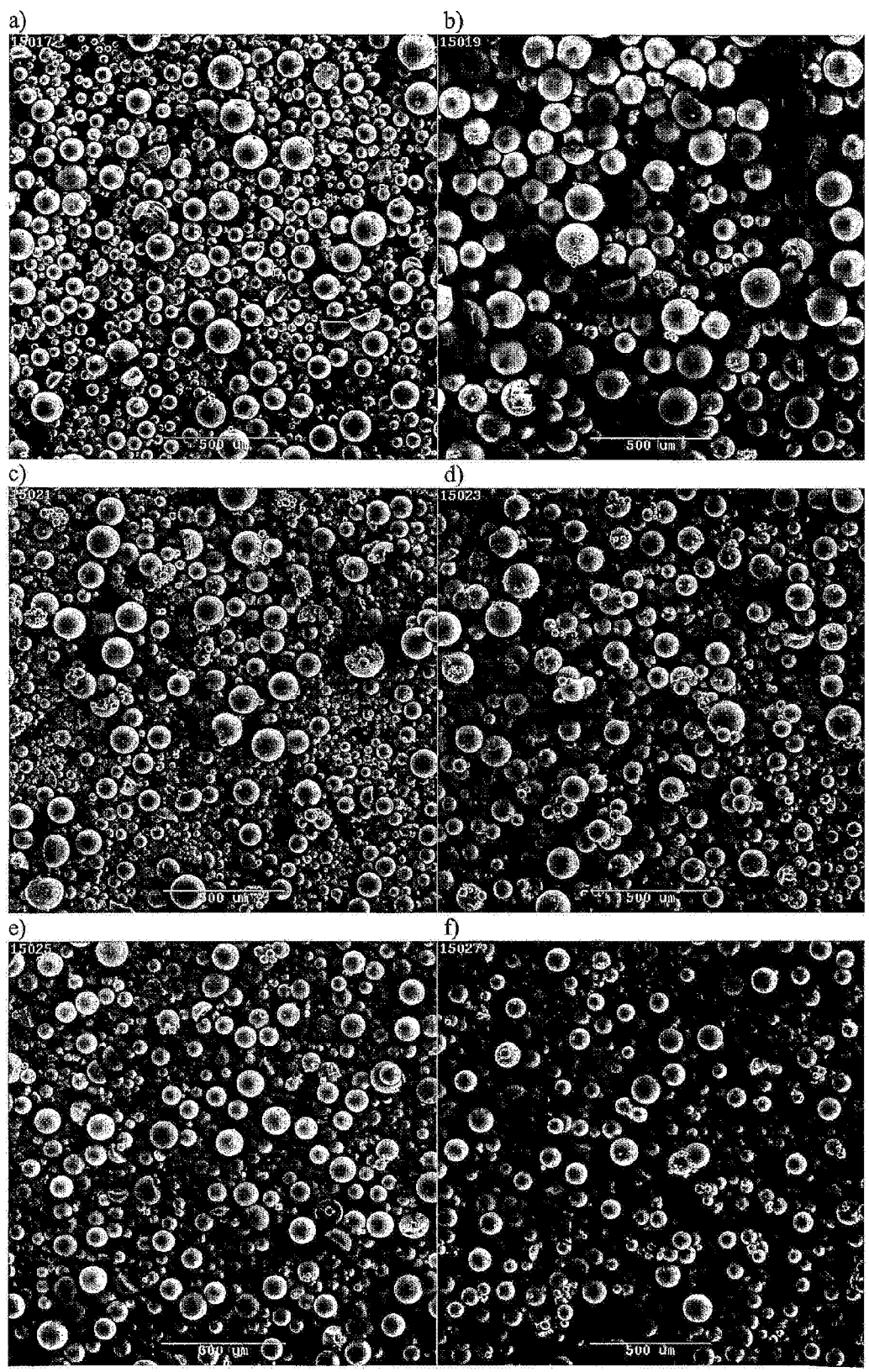
FIG. 9 shows electron micrographs of silica particles according to the invention, illustrating size and distribution of the particles as a function of water:TMOS molar ratio, with this ratio being: (a) 2; (b) 3; (c) 4; (d) 5; (e) 6; (f) 8; (g) 16 and other experimental conditions being: $Oil_1$ 0.400 mL dodecane with 0.800 mg SB-35; Tween 21 0.665 mmol; $H_2O_{(1)}$ and $H_2O_{(2)}$ pH2 $HNO_3$ solution; TMOS 29.650 mmol; $Oil_2$ 225 mL cyclohexane; $Surf_2$ Span 80 58.33 mmol.
Figure 9:
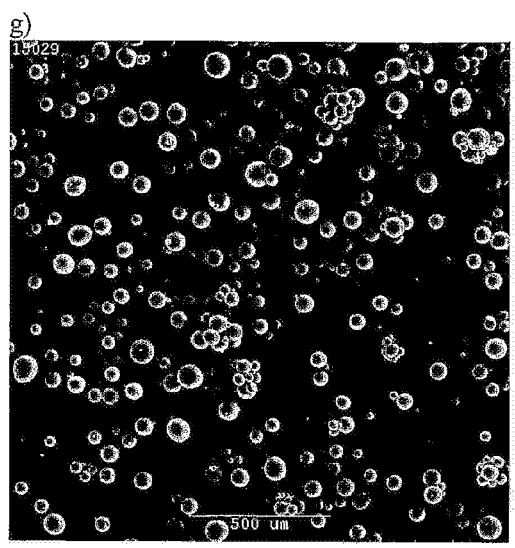

With dodecane as the internal oil phase, the particle size and distribution as a function of water:TMOS molar ratio is shown in FIG. 9. As the water: TMOS molar ratio was increased from 2 to 8, the particle size and size distribution hardly changed. However, at a water:TMOS molar ratio of 16, the size distribution became narrower and particles became smaller. The highest encapsulation efficiency of SB-35 resulted from a water:TMOS molar ratio of 4, by visual observation. The stoichiometric amount of water for the sol-gel reaction is 2. Usually, to drive the reaction to completion in a reasonable time, a water:TMOS molar ratio of 4 was used. The increasing amount of water, which is the reactant, as well as an increasing amount of catalyst ($H^+$) might be expected to increase the rate of the condensation reaction which might thus lead to a faster gelation inside the hydrophilic domains, and smaller and less polydisperse particles. Because the emulsion system is kinetically unstable (i.e. the double emulsion droplets will coalesce and phase separate with time), if the condensation rate is too low then droplet coalescence takes place prior to "freezing" of the structure by gelation, thus leading to an increased particle size. The reason behind the optimum oil encapsulation observed for a water: TMOS molar ratio of 4 is not clear. One can surmise that this specific ratio provided the fastest condensation time without an increased dilution (at high water ratio) that allows the internal oil droplets to migrate to the outside oil phase, thus decreasing the encapsulation efficiency. In other words, the ratio of 4 might present a good compromise between gelation speed and viscosity of the hydrophilic domain to keep the hydrophobe inside.

The same experiments were repeated replacing dodecane with limonene, with the results showing that the highest encapsulation efficiency was obtained at a water:TMOS molar ratio of 4, observed visually.

4. Influence of ORMOSIL Addition

Figure 10:
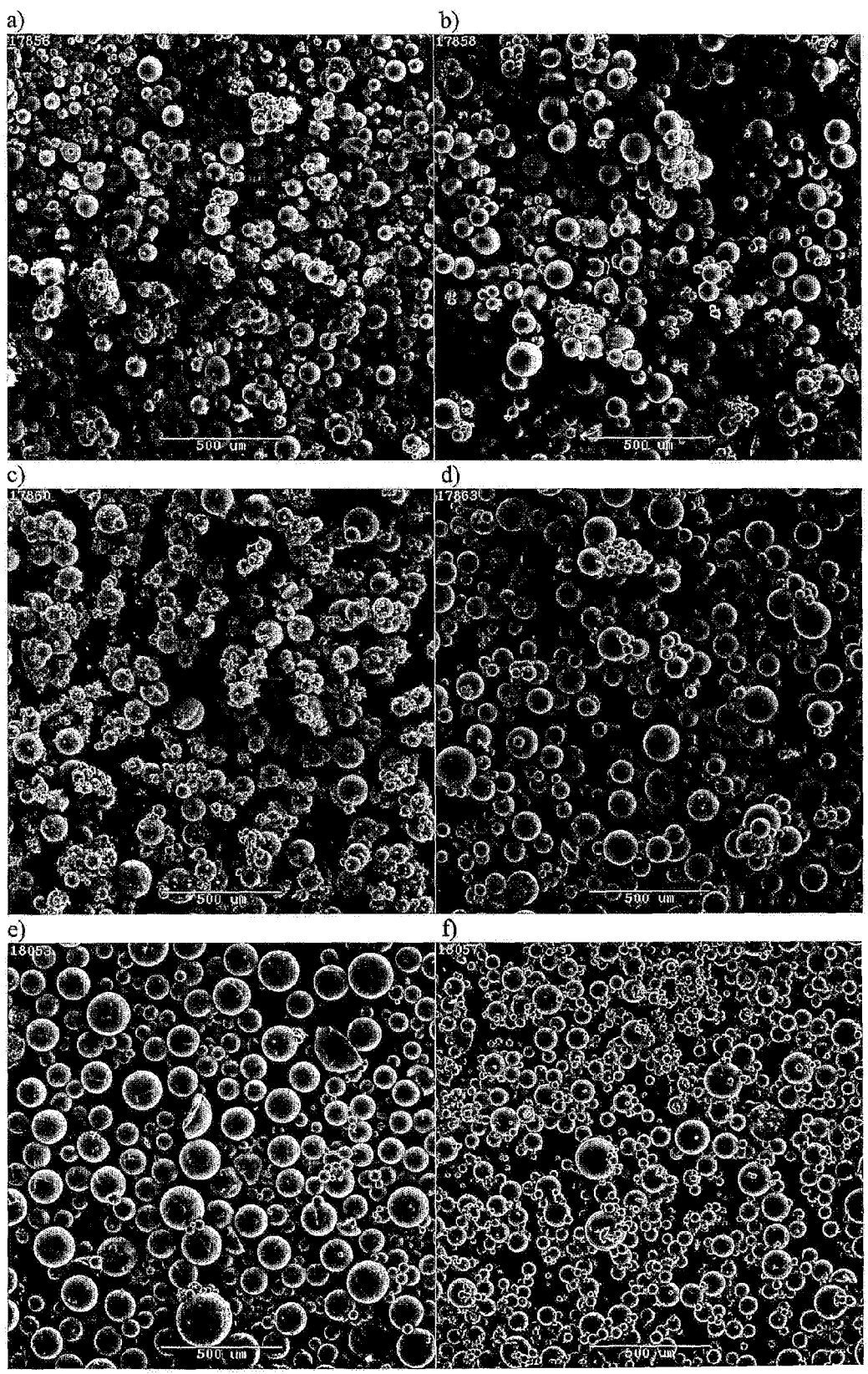
FIG. 10 shows electron micrographs illustrating the ORMOCER effect on particle formation: (a) 100 mol % TMOS; (b) 75 mol % TMOS and 25 mol % VTMS; (c) 75 mol % TMOS and 25 mol % PTMS; (d) 75 mol % TMOS and 25 mol % MTMS in which other experimental conditions are: $Oil_1$ 0.360 mL limonene with 0.720 mg SB-35; Tween 21 0.575 mmol; $H_2O_{(1)}$ and $H_2O_{(2)}$ 1.068 mL pH2 $HNO_3$ solution; total silicon precursor 29.650 mmol; $Oil_2$ 150 mL cyclohexane; $Surf_2$ Span 80 30.03 mmol and in which (e) was made using the same conditions as (d) except Span 80 was 90 mmol; and (f) was made using the same conditions as (b) except Span 80 was 90 mmol.

The SEM images in FIG. 10 shows that spherical particles were formed by mixed precursors, except APTMS, which results in a gelled product. In addition, it was also observed that the particle size distribution became narrow as the Span 80 concentration increased from 0.2 mol/L to 0.6 mol/L, which is consistent with results described above.

The rationale for using hybrid chemistry was that the encapsulation efficiency of the hydrophobic dye might be increased by introducing ORMOSIL such as MTMS, VTMS and PTMS. These precursors were expected to be able to increase the hydrophobic sites inside particles and to interact with the inner oil phase more effectively, thus keeping the oil inside the microspheres. In addition, the ORMOSIL was expected to assist to narrow the internal channels of the silica matrix, thus decreasing the opportunities of the inner oil to be released. However, addition of ORMOSIL did not improve the encapsulation efficiency of hydrophobic molecules (see Table 2). Compared with TMOS, ORMOSIL precursors have faster hydrolysis rates but slower condensation rates due to the poisoning effect of the organic group on the condensation reaction (loss of 1 condensation site out of 4). This decrease in the condensation rate as well as a decrease in connectivity resulting in a reduced viscosity of the hydrophilic domain, might produce increased migration of the hydrophobe towards the external oil phase and thus may explain the lower encapsulation efficiency.

Figure 11:
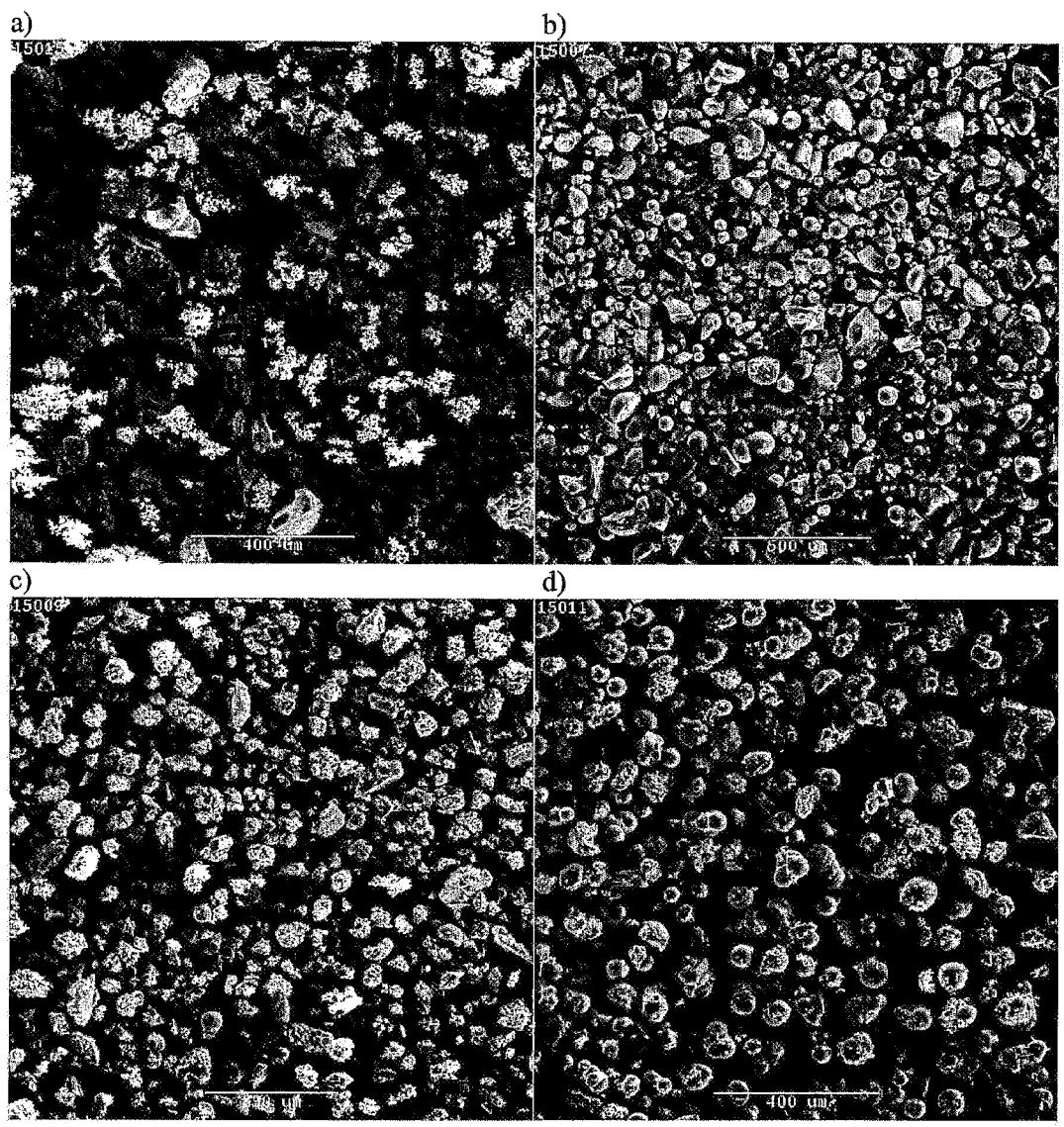
FIG. 11 shows SEM images of silica particles produced using TEOS with a water to TEOS molar ratio: (a) 2; (b) 4; (c) 8; (d) 16, and other experimental conditions being: $Oil_1$ 0.400 mL dodecane with 0.800 mg SB-35; Tween 21 0.665 mmol; $H_2O_{(1)}$ and $H_2O_{(2)}$ pH2 $HNO_3$ solution; TEOS 29.650 mmol; ethanol 118.6 mmol (added in sol-gel solution); $Oil_2$ 225 mL cyclohexane; $Surf_2$ Span 80 58.33 mmol.

5. Water to TEOS Molar Ratio Effect:

TEOS was also used as silicon precursor and the water: TEOS molar ratio was varied from 2 to 16. The corresponding SEM images are shown in FIG. 11. Most of the products were irregularly shaped except the last sample, suggesting that TEOS may need more ageing time to form spherical particles. Increasing the water:TEOS molar ratio accelerated the reaction rate, hence more spherical particles were obtained at higher ratios. An alcohol such as ethanol is required for miscibility of TEOS and water. This added alcohol together with the ethanol generated by hydrolysing TEOS can perturb/destroy the double emulsion structure if it is not removed during the evaporation process. As a result, more irregularly shaped particles were produced.

Figure 12:
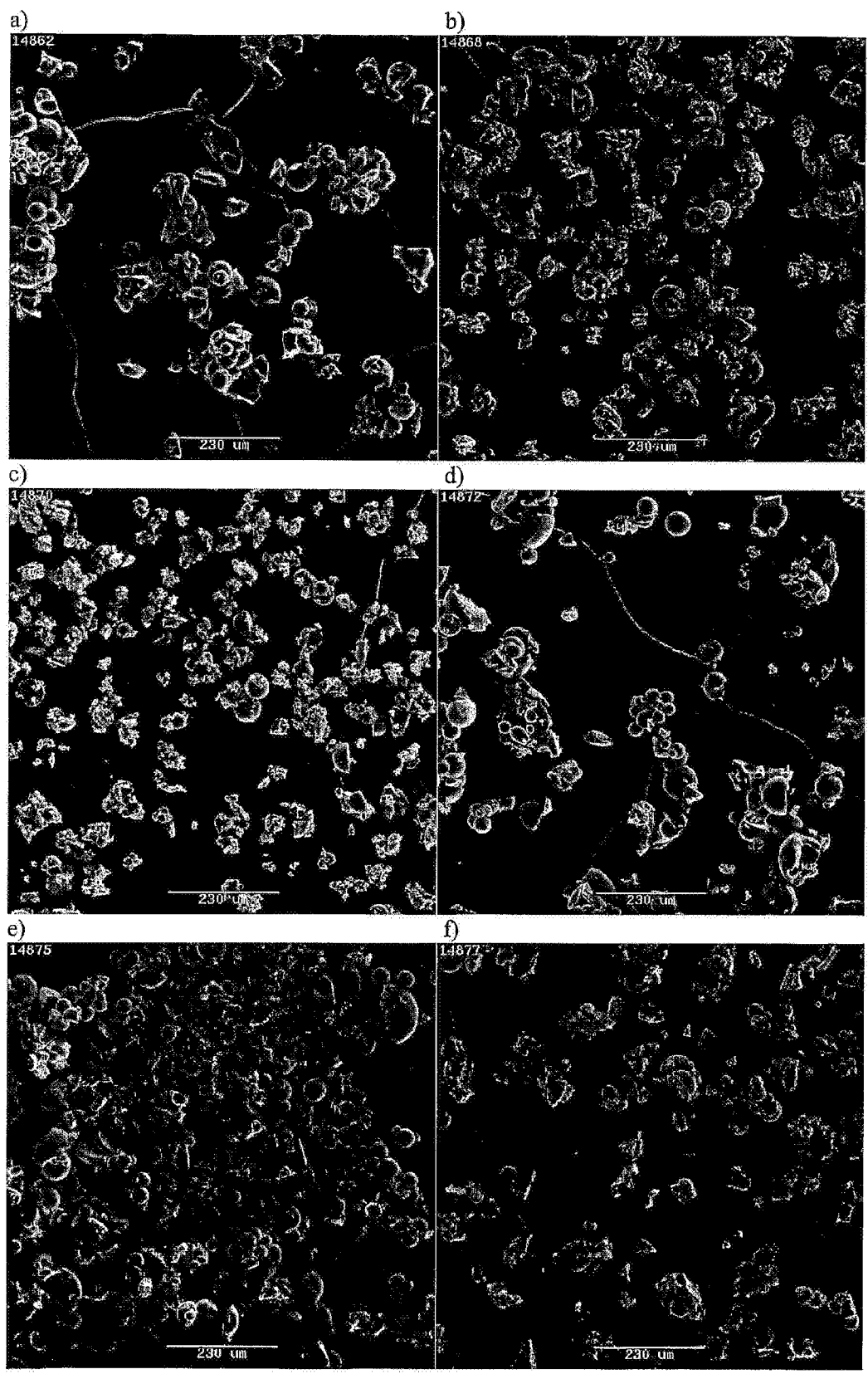
FIG. 12 shows SEM images of silica particles produced using Span 20 as hydrophobic surfactant, with a Tween 21 amount: (a) 0.575 mmol; (b) 0.968 mmol; (c) 1.314 mmol; (d) 1.724 mmol; (e) 2.107 mmol; (f) 2.490 mmol and other experimental conditions being: $Oil_1$ 0.400 mL dodecane with 0.800 mg SB-35; $H_2O_{(1)}$ and $H_2O_{(2)}$ 1.068 mL pH2 $HNO_3$ solution; TMOS 29.650 mmol; $Oil_2$ 185 mL cyclohexane; $Surf_2$ Span 20 59.17 mmol.
Figure 13:
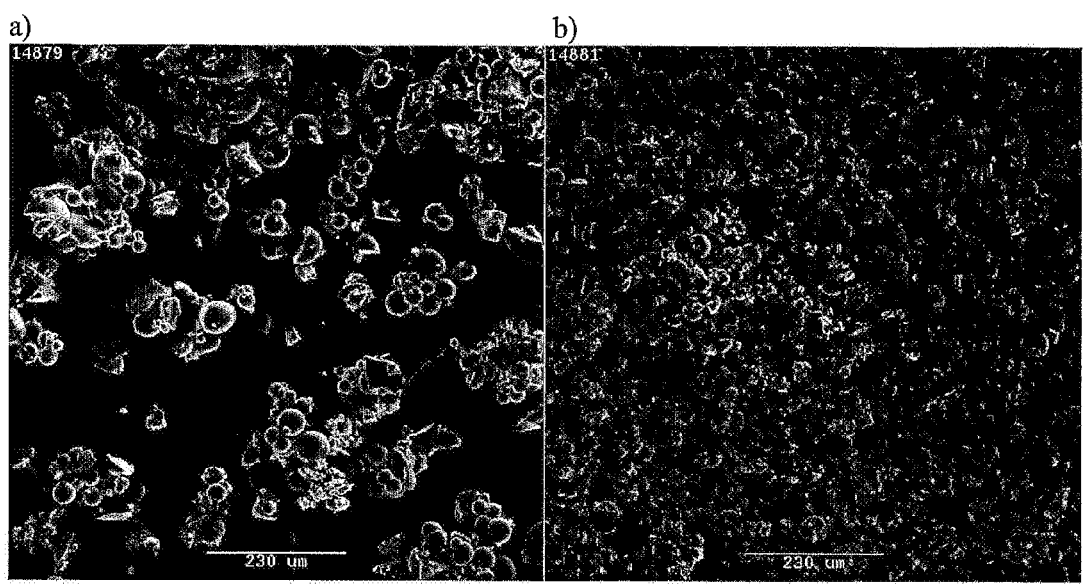
FIG. 13 shows SEM images of silica particles produced using Tween 20 and Tween 80: (a) Tween 20 0.245 mmol; (b) Tween 80 0.229 mmol; and other experimental conditions are same as described for FIG. 11.

6. Hydrophobic Surfactant Effect:

Span 20 was also examined as a surfactant for the outer oil phase. FIG. 12 displays the SEM images of silica particles prepared at different Tween 21 concentrations, while FIG. 13 shows the SEM results for particles produced using Tween 20 and Tween 80 combined with Span 20. Regardless of the type of hydrophilic surfactant and concentration, the results show that more spherical silica particles were produced using Span 80 than using Span 20. This confirms that the low HLB value of surfactants such as Span 80 facilitated the formation of the hydrophilic droplets and thus enhanced the production of spherical particles.

Figure 14:
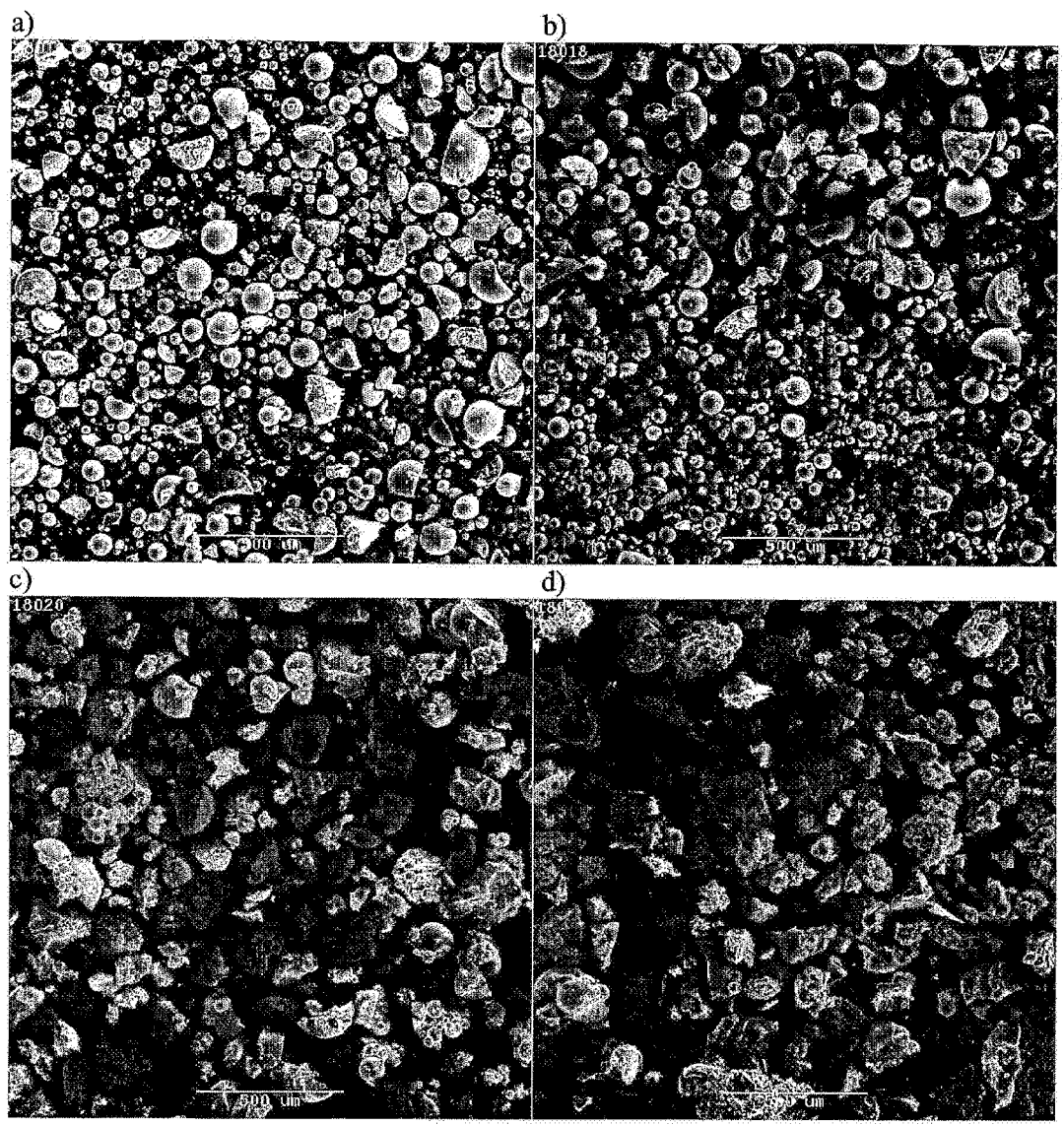
FIG. 14 shows SEM images of silica particles produced by adding PEG (polyethylene glycol) in the hydrophilic domain and HPC (hydroxypropyl cellulose) in the hydrophobic domain combined with variation of hydrophilic surfactant and outer oil phase, in which the experimental conditions are as shown in Table 3.
Figure 14:
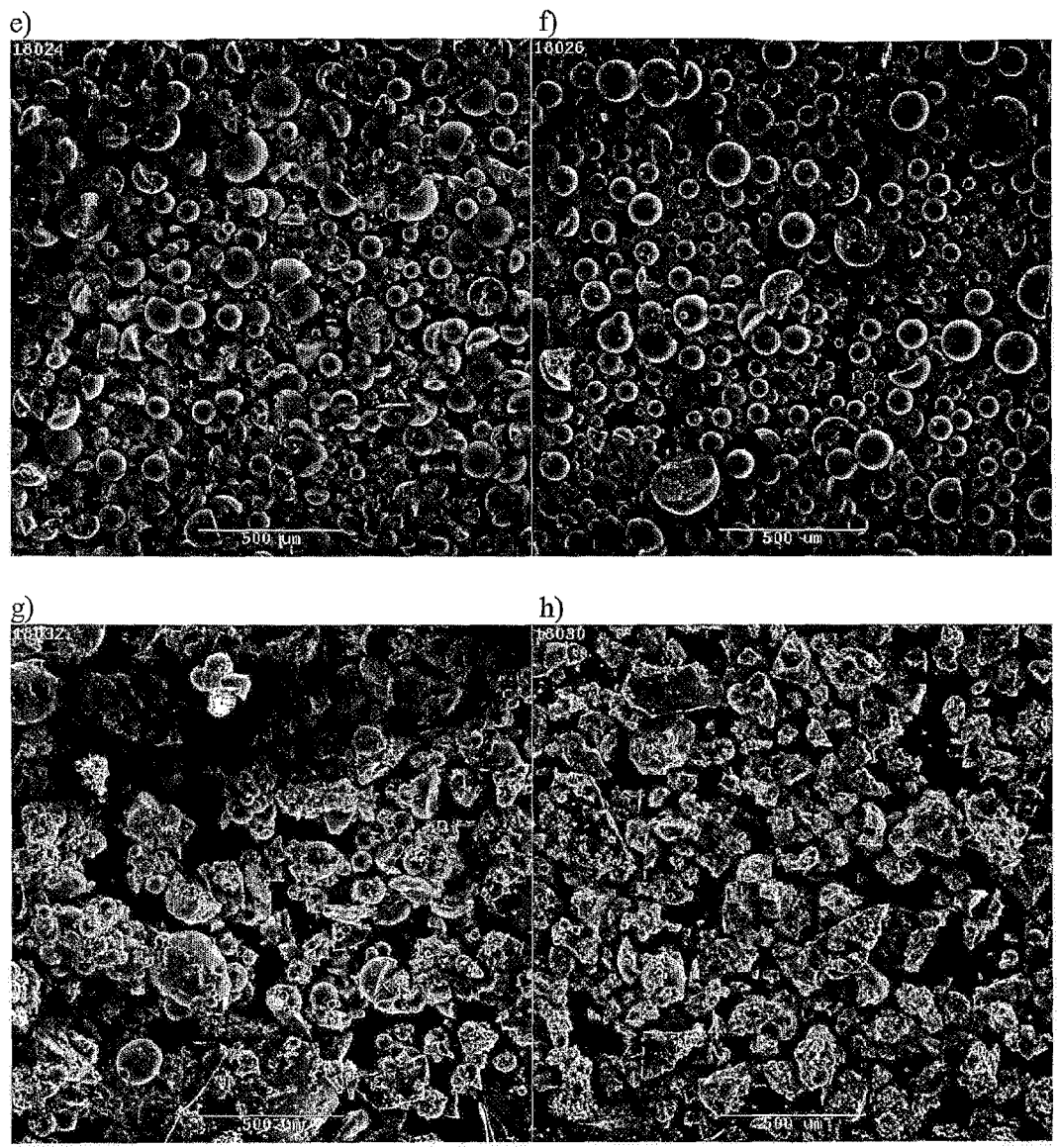

7. Comparative Test: Influence of the Addition of PEG in the Hydrophilic Domain and HPC in the Hydrophobic Domain PEG (MW: 20,000) solution was prepared by dissolving 0.300 g PEG in 1.000 mL pH=2 $HNO_3$ solution, and the calculated amount of this solution was used as Water$_{(1)}$ phase. HPC (MW: 370000) solution was made by completely dissolving 2.500 g HPC in 100.00 mL (82.00 g) 1-hexanol (density: 0.82 g/cm$^3$). A known amount of this solution was added to the outer oil phase to increase the viscosity. The detailed experimental conditions are presented in Table 3 and the corresponding SEM images are illustrated in FIG. 14.

The particles produced using cyclohexane as the outer oil phase (e and f) were more spherical and less damaged compared with those produced using kerosene (a and b). In addition, the presence of PEG in the aqueous phase and HPC in the outer oil phase led to irregular particles regardless of the type of outer oil phase used and only a fraction of SB-35 could be incorporated in the product. These results conflict with earlier results in which only HPC was used. This may suggest that the influence of PEG and HPC should have been investigated separately. In addition it is proposed that PEG may exert a detrimental effect on the particle morphology while HPC may be able to assist the particle formation if no alcohol is introduced. This is discussed further in the next section.

Figure 15:
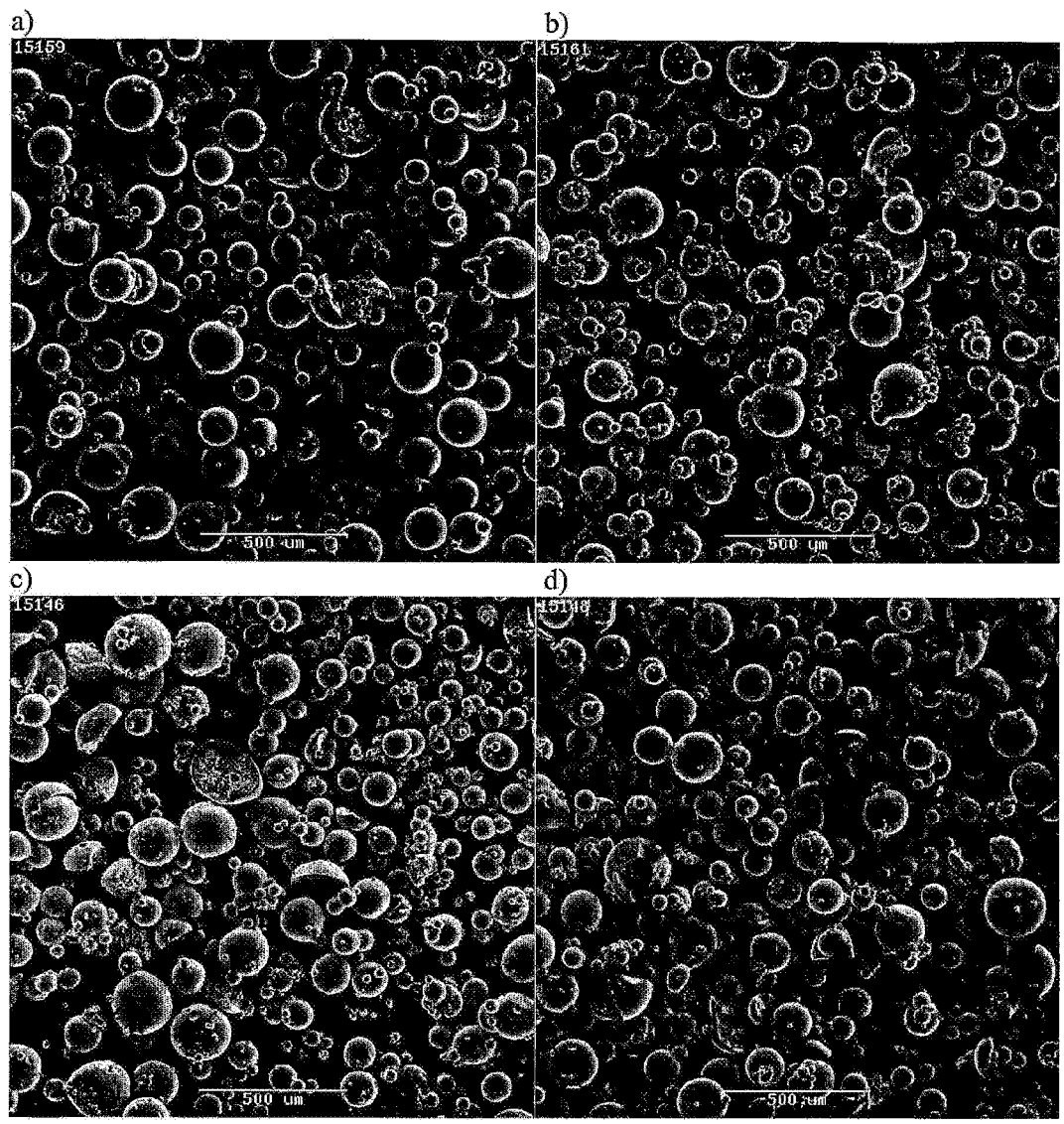
FIG. 15 shows electron micrographs illustrating particle morphology produced by different hydrophilic surfactants in presence of PEG and HPC, in which the experimental conditions are as shown in Table 4.
Figure 15:
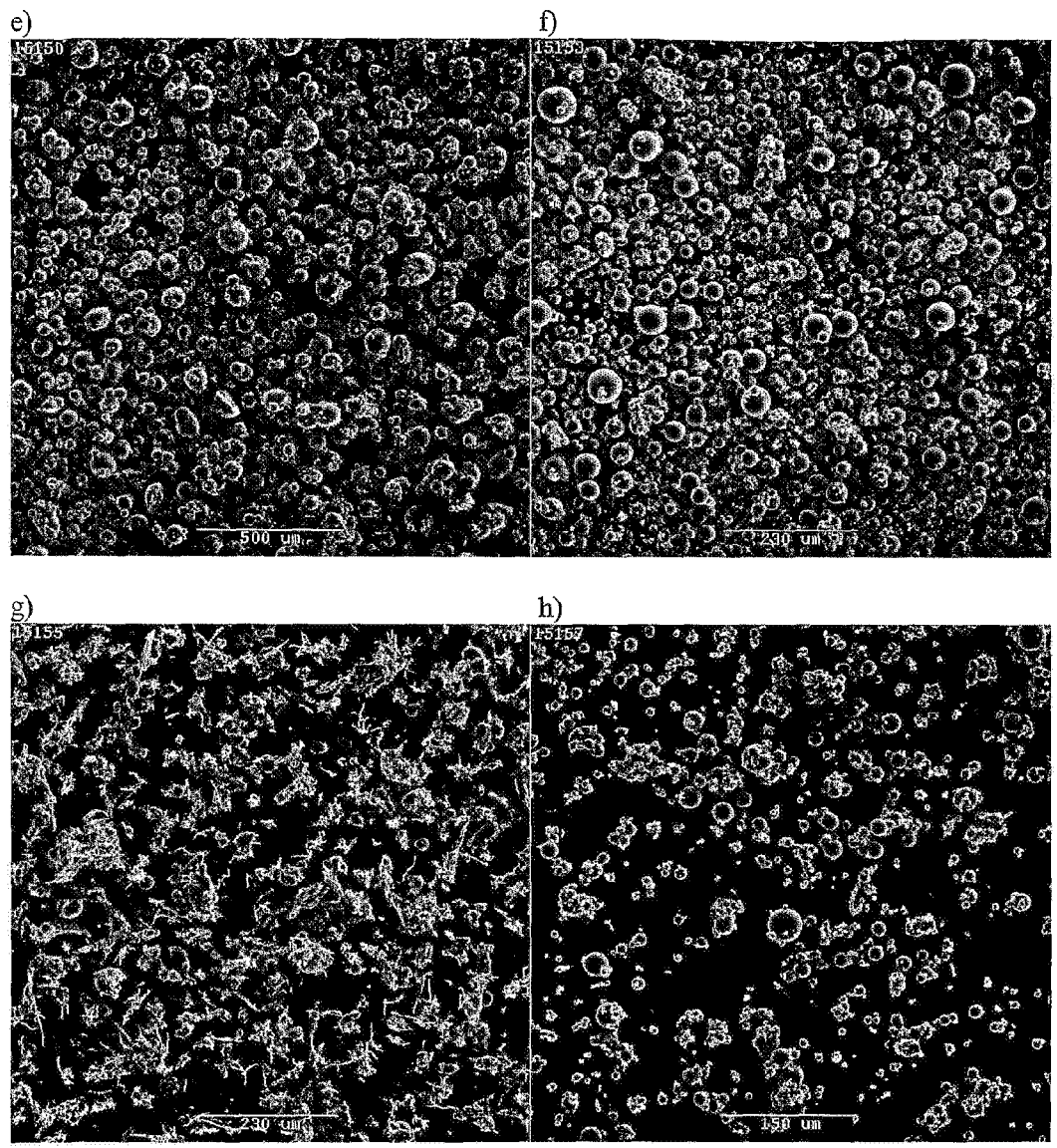

8. Comparative Test: Particle Morphology Produced with Different Hydrophilic Surfactants in Presence of PEG and HPC:

The experimental conditions are summarised in Table 4 and the corresponding SEM images are shown in FIG. 15. Compared with the previous investigation (see Table 3), the outer phase oil volume was doubled and the hydrophobic surfactant concentration increased slightly from 0.5 mol/L to 0.6 mol/L. Despite the presence of PEG and HPC, spherical particles were formed and doubling the HPC amount was found to have no significant effect on particle morphologies except for the Tween 80 system. A slight increase in the volume of the internal phase had a small influence on particle size and size distribution which is shown from a to d. Particles produced using Tween 21 incorporated the most dye by visual observation. The corresponding particle size was quite large. Use of Tween 20 resulted in successful encapsulation of the dye although the encapsulation efficiency was not as high as for the Tween 21 system, and the Tween 20 system formed much smaller particles. For the Tween 80 system, no dye was incorporated (as judged visually) and irregularly shaped particles were produced at high HPC contents.

Stability of the multiple emulsion has been considered as a prerequisite for successful encapsulation of the hydrophobic molecule, retinol. Therefore trials with increasing viscosity of the inner phase (by adding PEG) and the outer oil phase (by adding HPC) were performed as in section 7 above. Comparison with FIG. 6c shows that no significant change in the particles morphology was observed upon addition of PEG and HPC. Comparison with FIG. 7 also showed little change for the Tween 20 system upon addition of both thickening agents. In contrast, the addition of PEG and HPC to the Tween 80 system did lead to some smaller size particles (comparison between FIGS. 15h and 8c). However, non-spherical particles were produced, as particularly noted in FIG. 15g.

It is generally believed that increasing the viscosity of the outer oil phase facilitates the formation of a stable double emulsion, thus producing spherical particles. However, the addition of HPC may slightly change the Span 80 interface between the outer oil and hydrophilic phase, and as a result, in some cases, irregularly shaped particles are produced. In addition, increasing the outer oil phase viscosity by adding HPC or increasing Span 80 may lead to different results. As discussed earlier, increasing the Span 80 concentration resulted in a higher encapsulation efficiency for SB-35. On the other hand, the presence of PEG in the hydrophilic domain possibly results in destruction of the local structure of the internal oil phase and internal silica surface, thus producing particles with irregular shapes and without incorporated dye.

9. Influence of the Hydrophilic Surfactant Concentration (with Limonene as the Internal Oil Phase)

Figure 16:
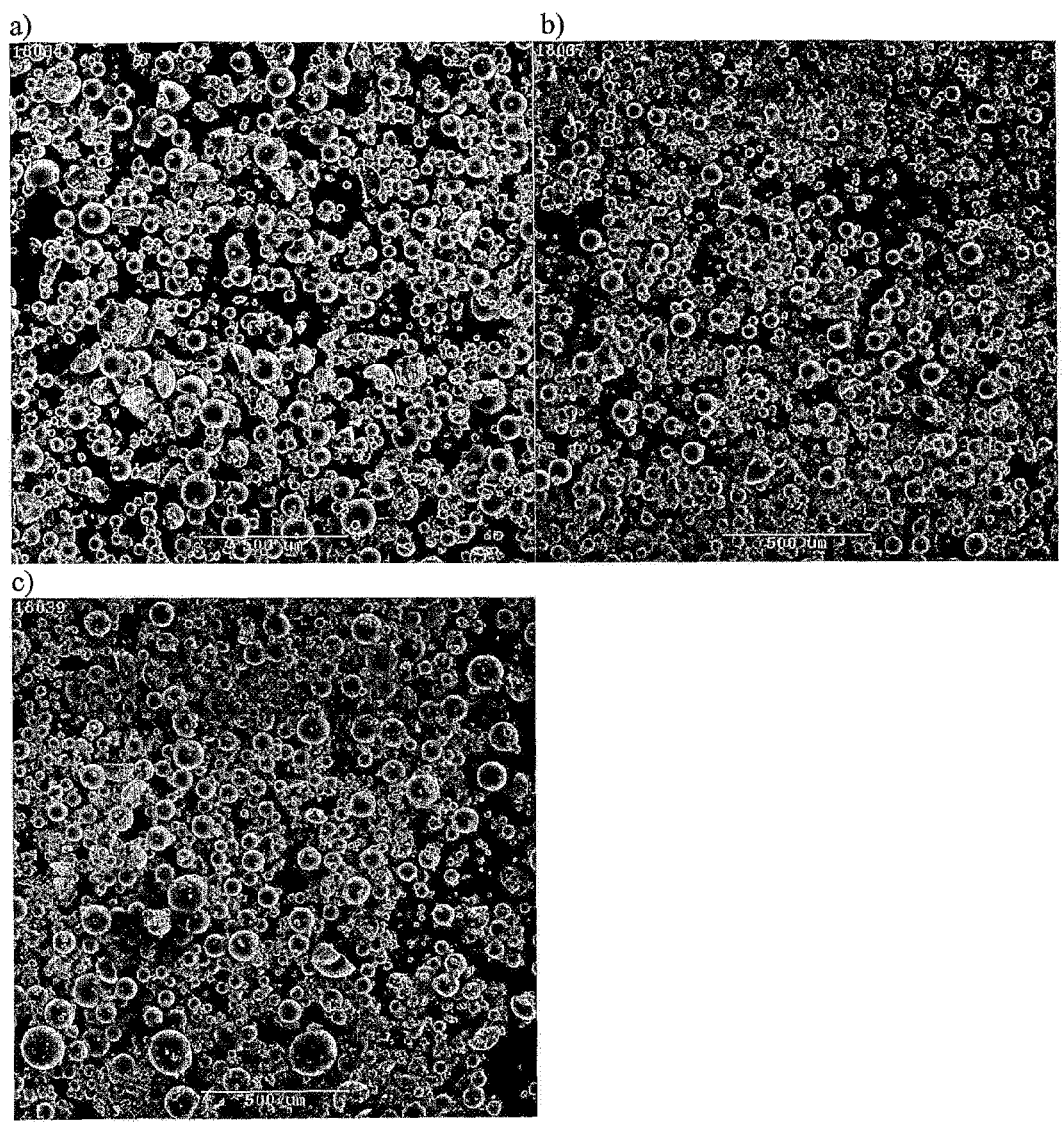
FIG. 16 shows SEM images of silica particles synthesised at various hydrophilic surfactant concentrations with limonene as the internal oil phase, the amounts of Tween 21 being: (a) 0.958 mmol; (b) 2.874 mmol; (c) 3.831 mmol; and other experimental conditions being: $Oil_1$ 0.360 mL limonene with 0.720 mg SB-35; $H_2O_{(1)}$ and $H_2O_{(2)}$ 1.068 mL pH2 $HNO_3$ solution; TMOS 29.650 mmol; $Oil_2$ 150 mL cyclohexane; $Surf_2$ Span 80 90 mmol.
Figure 17:
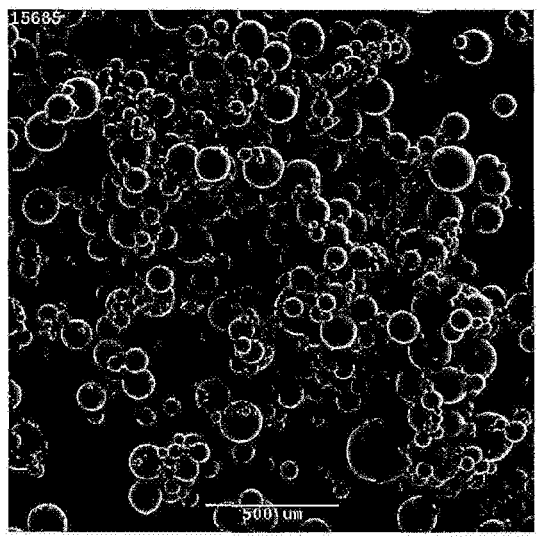
FIG. 17 shows an SEM image of silica particles with encapsulated retinol, where the amount of each component is 40% of that in the typical synthesis of the examples with the amount of retinol 0.210 g.

As noted above, higher Tween 21 concentrations led to a smaller particle size and narrower size distribution, even though no improvement was observed when the concentration is above about 0.6 mmol (FIG. 6). This may suggest that the increase in surfactant (Tween 21) concentration was moderately effective in stabilising the oil$_1$/'W' system. Nevertheless, this increase in stability did not improve the encapsulation efficiency of the dye. There were no significant differences observed in the particle size and distribution for the various surfactant concentrations (see FIG. 16). This suggests that the properties and concentration of the hydrophobic surfactant in the outer oil phase have a significant effect on the particle morphology while the internal surfactant plays a major role in the encapsulation of hydrophobic species (once above a certain threshold value). The internal oil characteristics have less effect on the particle morphology as shown by the substitution of limonene by retinol, which produces slightly less polydispersed silica particles (see FIG. 17).

10. Influence of the Internal (Oil$_1$/'W'):External (Oil$_2$) Volume Ratio

Figure 4:
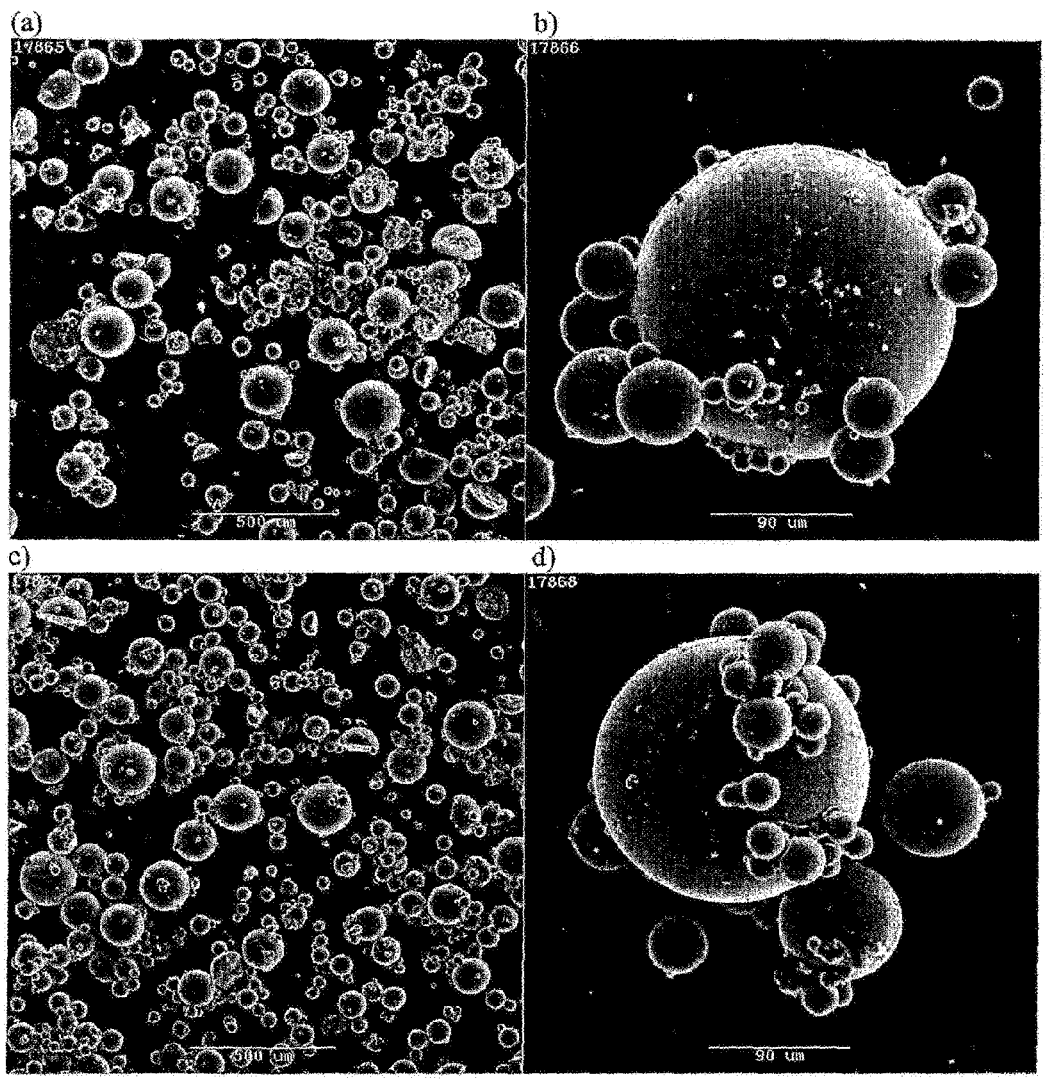
FIG. 4 shows SEM (scanning electron micrograph) images of micron silica particles according to the present invention, made using different Span 80 concentrations: (a and b) 0.26 mol/L, (c and d) 0.45 mol/L, (e and f) 0.60 mol/L, (g and h) 0.75 mol/L. Other parameters are same as the typical synthesis conditions described in the examples.
Figure 4:
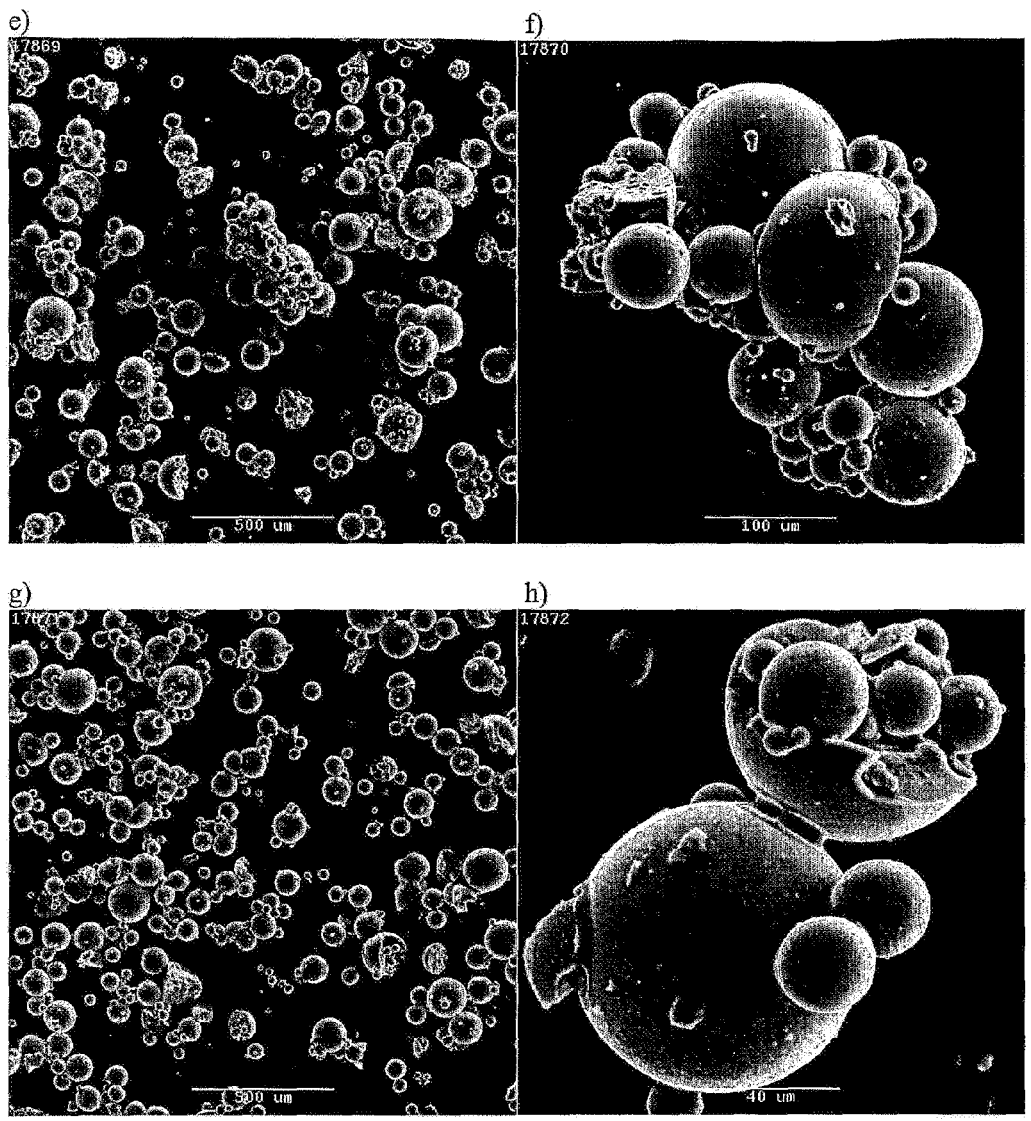
Figure 5:
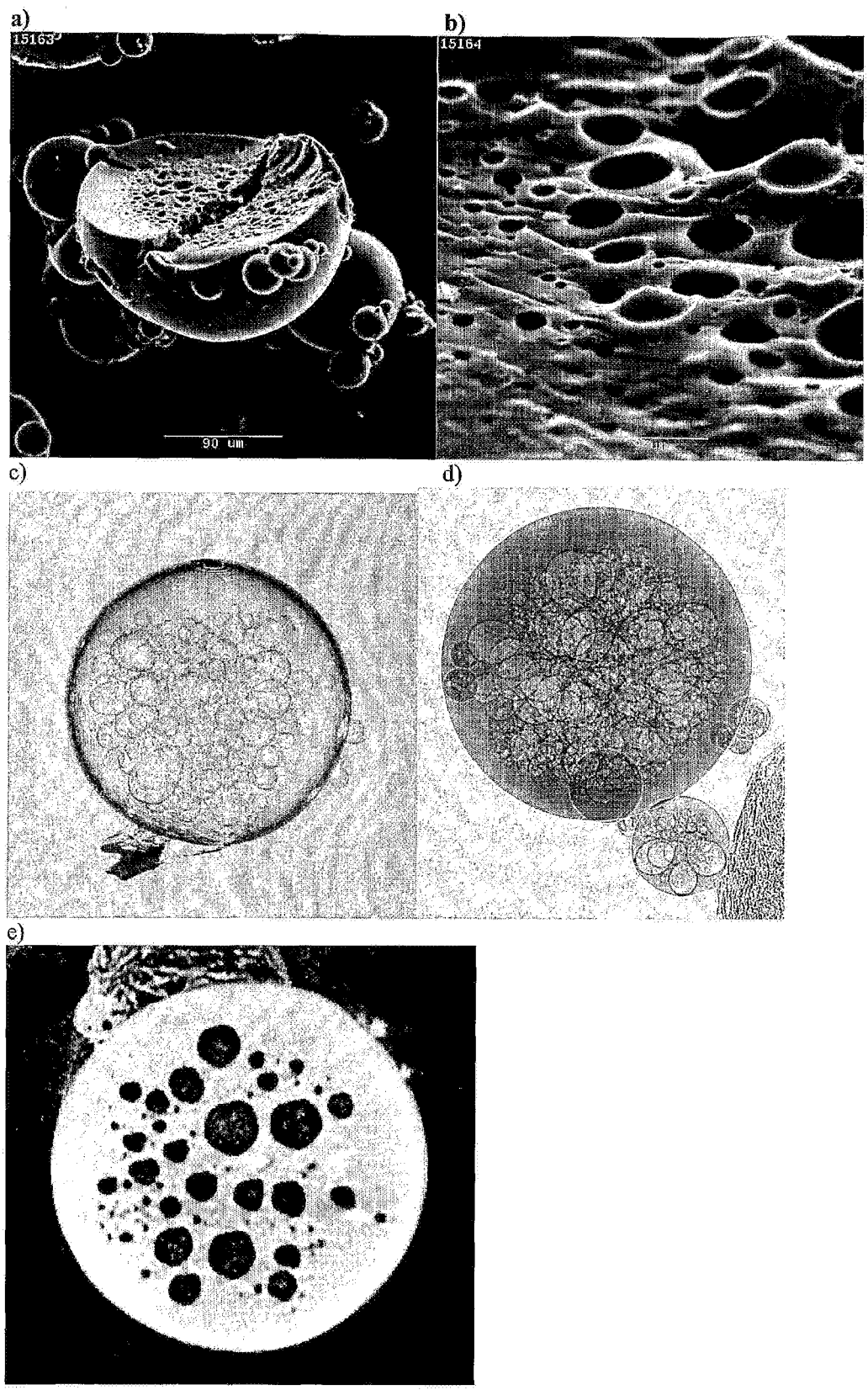
FIG. 5 shows (a and b) electron micrographs at two different magnifications, (c and d) phase-contrast x-ray microtomographic images, and (e) x-ray image. All images show the typical morphology of silica particles produced using the typical synthesis parameters of the examples.
Figure 18:
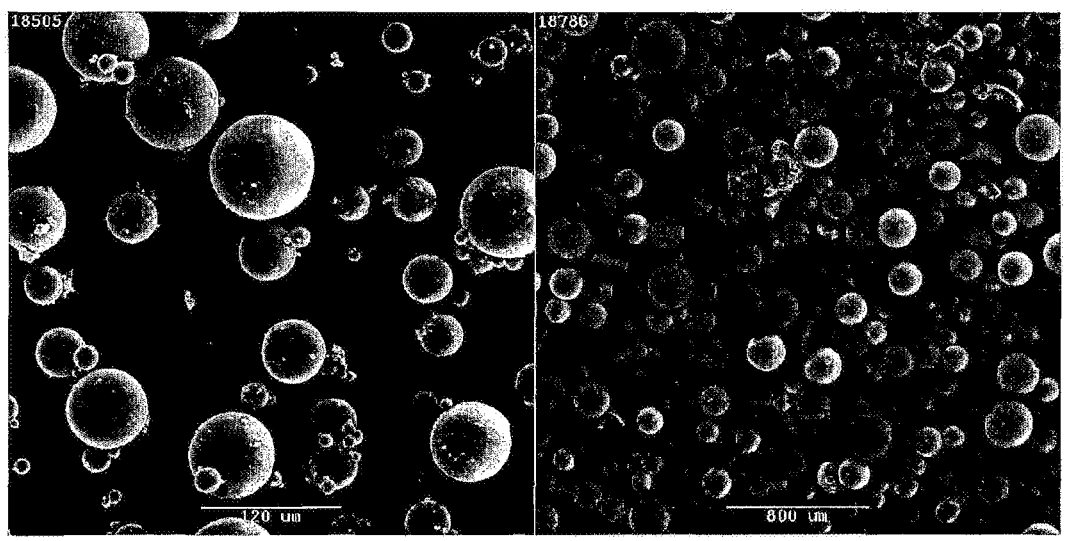
FIG. 18 shows SEM images of particles produced by adding double and four times amount of internal content, in which the experimental parameters are same as the typical synthesis conditions except: (a) cyclohexane 150 mL with Span 80 90 mmol; (b) cyclohexane 75 mL with Span 80 45 mmol.

Under the typical synthesis conditions described above, the particle size distribution was in the range 10-150 μm (FIG. 4-c). If the content of Oil$_1$/'W' was doubled, the particle size remained the same (FIG. 18-a). However, if the Oil$_1$/'W' was multiplied four times and the volume of outer oil phase was kept constant, the particle size increased and size distribution became much broader (10-300 μm): see FIG. 18-b. This increase in the internal volume led to a decrease in the Span 80:water molar ratio thus decreasing the rigidity of the outer walls and increasing the coalescence, leading to particle growth.

11. TGA/DTA Characterisation

Figure 19:
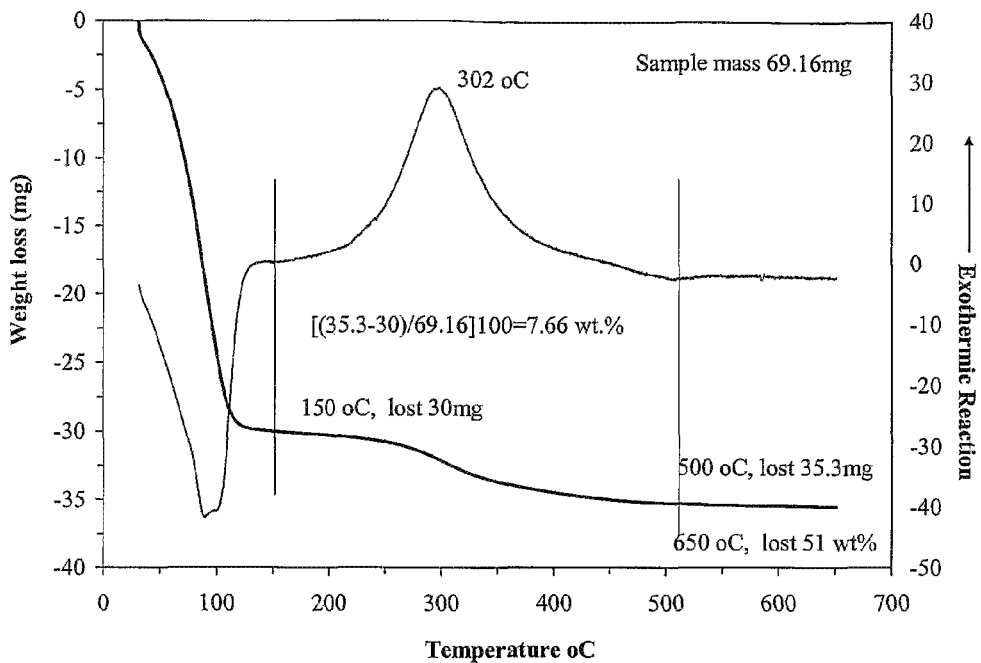
FIG. 19 shows TGA (thermogravimetric analysis) and DTA (differential thermal analysis) results for estimation of surfactant residue on particle surfaces for silica particles according to the present invention.

The surfactant residue on the particle surface was estimated by TGA/DTA analysis (FIG. 19). Two different decomposition steps were observed. The first weight loss (T<120° C.) corresponds to an endothermic reaction and can be attributed to the evaporation of volatiles (limonene and water). The second weight loss (120<T<500° C.) corresponds to an exothermic reaction and can be attributed to the combustion of the residual surfactant. The corresponding composition of limonene doped silica micron particles is 43.4 wt % water plus oil, 7.6 wt % surfactant, 49.0 wt % silica.

12. Characterisation of the Porous Structure Using Nitrogen Adsorption

Figure 20:
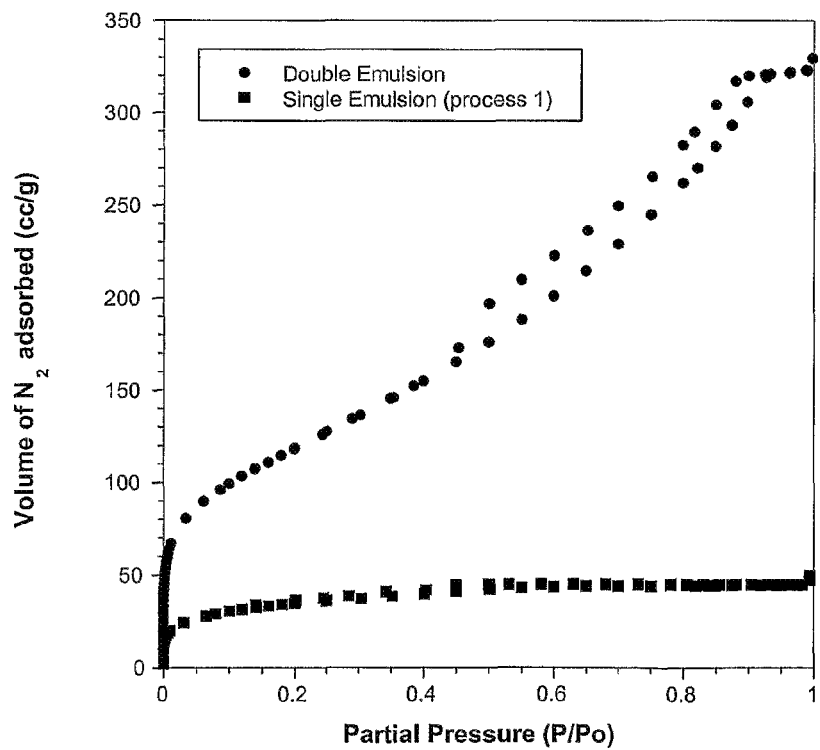
FIG. 20 shows sorption isotherms of two samples of particles: 1) produced according to the process of the present invention ("double emulsion") using Tween 21 as internal surfactant, and 2) produced using "process 1" of WO1/62232.

The curve of the adsorption isotherm represents a fingerprint of the texture of the solid under study (FIG. 20). The shape of the adsorption isotherm indicated the presence of a small amount of micropores and a large amount of mesopores. The BET specific surface area value of 431.3 m$^2$/g confirmed the presence of micropores and suggested that the porosity in the sphere was not due only to the micron-sized cavities observed by SEM in FIG. 5 but to some internal matrix porosity. The maximum pore volume value of 0.51 cm$^3$/g (measured at relative pressure 0.99755) confirmed the production of a very highly porous solid. The hysteresis between the adsorption and desorption branches, signified cylindrical shaped pores. Based on this assumption, a DFT (Density Functional Theory) analysis using a cylindrical pore model was conducted and revealed the presence of a broad pore size distribution (from 1-30 nm) with a peak at 6 nm.

It is interesting to note the difference between the internal product of those spheres with that produced by the process 1 (C. J. Barbé, J. R Bartlett, Controlled Release Ceramic Particles, Compositions Thereof, Processes of Preparation and Methods, PCT WO 01/62232, (2001)) using similar sol-gel conditions (TMOS, water:alkoxide ratio of 4 and pH=2). The particles produced by process 1 were primarily microporous, with a pore volume around 0.1 cm$^3$/g. This suggests that either the oil encapsulation or the internal surfactant (e.g. Tween 21) played a significant role in the modification of the internal structure of the matrix. It is likely to be of primary importance to control the internal structure of the silica matrix in order to control the release rate of the hydrophobe.

13. Encapsulation and Release Rate of Dye:

Indirect method: Five standard solutions with varying concentrations of limonene (containing 0.200 mg/ml of SB-35) were prepared using 0.6 mol/L Span 80/cyclohexane. The solutions were scanned from 450 to 800 nm, and the height of absorbance (Abs) between the peak and baseline at 650 nm recorded. SB-35 doped silica particles were produced by the synthesis process described earlier, and the encapsulation efficiency was 47.8 wt. % (average of three samples).

Direct method: The standard calibration curve was obtained as above, and the Span 80 concentration in ethanol was estimated from the surfactant residue on the particle surface. A known fraction of product was dispersed in ethanol, and the suspension was stirred for 3 days until the absorbance of the supernatant was stable. The calculated encapsulation efficiency of SB-35 was 38.4 wt %, which is about 10 wt % less than the result from indirect method. This may be due to some binding of the dye molecules to the internal surface of the particle, thus artificially decreasing the efficiency.

Encapsulation efficiency by ORMOSIL spheres: SB-35 encapsulation efficiencies in silica spheres made by mixed precursors are shown in Table 3. The highest encapsulation efficiency was observed for the sample made by 25 mol. % MTMS, but the value is approximately 13 wt % less than the particles made with 100% TMOS. It is interesting to note that again the efficiency obtained by direct method was 10 wt % less than by the indirect method, but remained independent of the release media.

Figure 21:
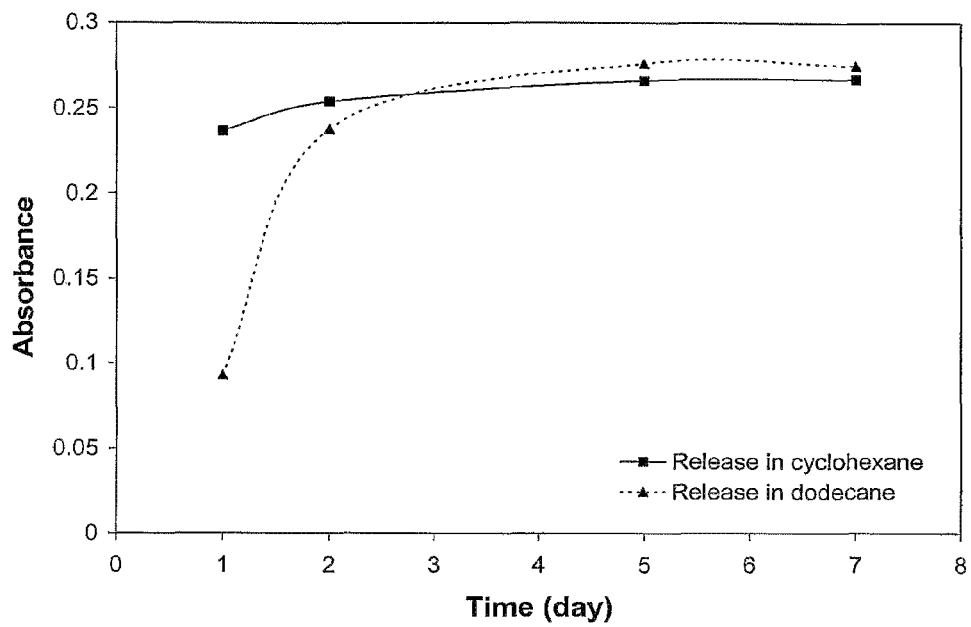
FIG. 21 is a graph showing release rate of SB-35 from silica microparticles according to the present invention in cyclohexane and dodecane.

Release rate: FIG. 21 shows the release rate of SB-35 from silica microparticles in cyclohexane and dodecane. The release of dye in cyclohexane was faster than in dodecane but after 3 days the absorbance stabilised to the same values in both systems suggesting that all dye was removed. The faster release rate observed in the case of the cyclohexane may be explained by the higher lipophilicity of the cyclohexane.

14. Encapsulation of Retinol

Figure 22:
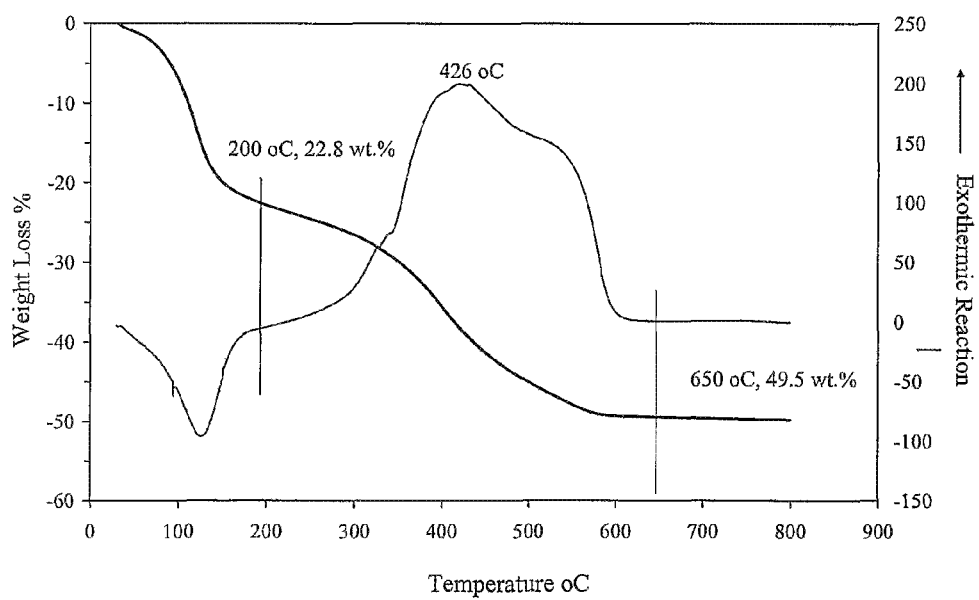
FIG. 22 shows TGA and DTA results of retinol doped silica particles according to the present invention, wherein the amount of each component is 40% of that in the typical synthesis with retinol 0.210 g.

The SEM image of retinol-doped silica particles (FIG. 17) reveals that the particle size and distribution were independent of the internal oil phase, which may be either a liquid (dodecane or limonene) or a solid (retinol). The TGA/DTA results of the retinol doped particles are displayed in FIG. 22. The first weight loss (T<200° C.) can be attributed to the evaporation of water and retinol, whereas the second weight loss (200<T<650° C.) corresponds to the combustion of the residual surfactant. The composition of the retinol-doped silica micron particles was 22.8 wt % water plus retinol, 26.7 wt % surfactant, and 50.5 wt % silica.

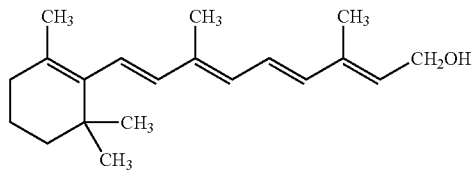

Retinol: MW 286.5, $\lambda_{max}$ 325 nm, yellow powder

Figure 23:
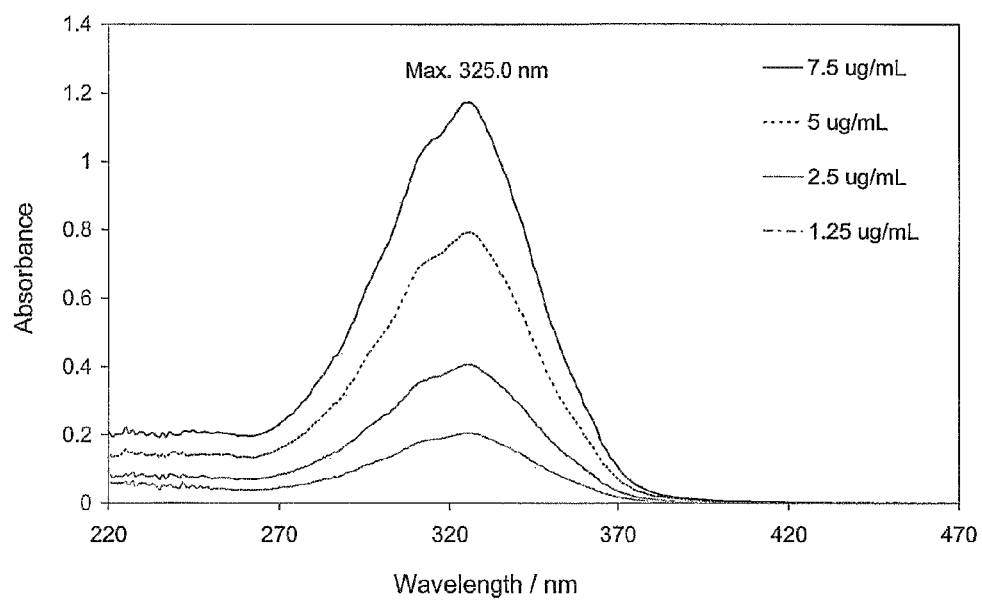
FIG. 23 shows UV/Vis spectra of retinol at different concentrations dissolved in ethanol.

The UV/Vis spectrum of pure retinol dissolved in anhydrous ethanol is shown in FIG. 23. Retinol exhibits a strong absorption peak at 325 nm and has a detection limit of approximately 0.1 ppm. Unfortunately the retinol band disappeared during release in anhydrous ethanol, suggesting that the retinol was either strongly bonded to the silica surface or degraded to another species. FT-IR analysis of the silica particles containing retinol could not detect the retinol because the weak retinol bands were swamped by the much more intense silica and surfactant bands.

Figure 24:
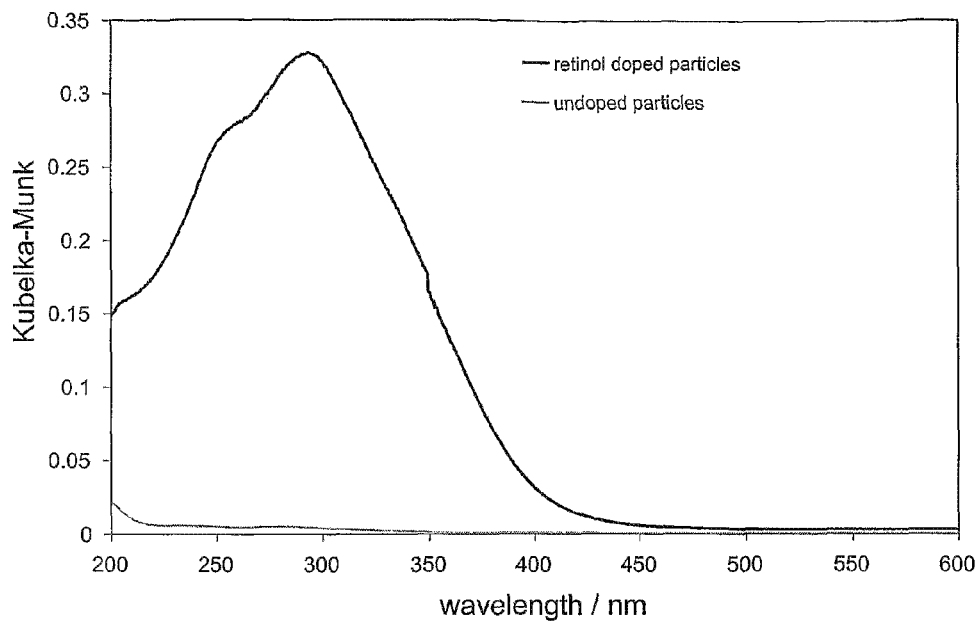
FIG. 24 shows a diffuse reflectance spectrum of retinol-doped particles and control particles according to the present invention.

Solid samples of retinol-doped silica particles were analysed by UV/Vis spectroscopy. The corresponding spectrum is shown in FIG. 24 with a control sample produced by the same process in absence of retinol. A strong band was observed centered around 300 nm. In contrast, no significant absorbance appeared for the control sample. This confirms that the double emulsion process led to the encapsulation of retinol in silica particles.

Figure 25:
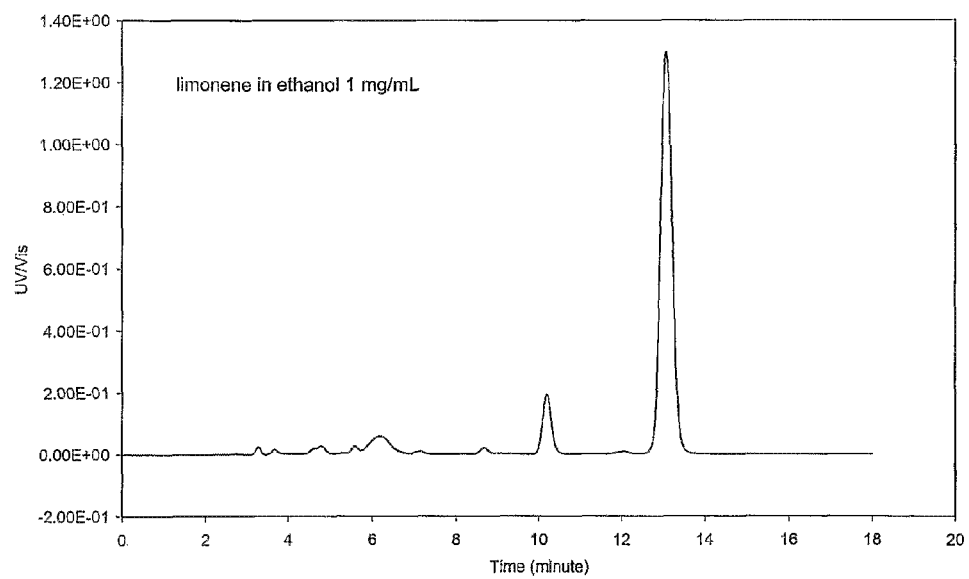
FIG. 25 shows a typical HPLC chromatogram to determine limonene.

15. HPLC Estimation of Limonene Encapsulation Efficiency:

A typical HPLC spectrum used to determine the limonene content of the particles is shown in FIG. 25. The encapsulation efficiency of limonene in silica microparticles was estimated at 14±6% for a typical synthesis. The encapsulation efficiency value can be obtained only by a direct method (i.e. leaching from the final particles) since a high amount of Span 80 significantly perturbs the quantitative measurement of limonene. The high variation in efficiency observed is possibly due to several reasons, such as variations in the washing and drying process, during which limonene is likely to be removed. Another interference factor during the HPLC measurement is the presence of surfactant Span 80, which has a broad retention time. This interferes with the limonene signal thus increasing the difficulty to quantify the release rate of limonene by HPLC.

The lower encapsulation efficiency of limonene compared to the hydrophobic dye (SB-35) can be explained by the different molecular structures:

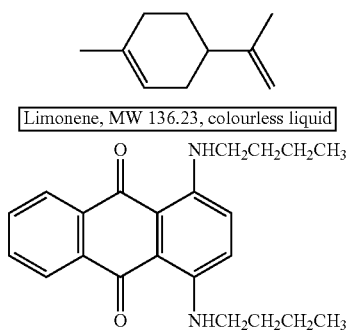

Solvent Blue-35 has hydrophilic sites (amine functional groups) which can conjugate or associate with the silica surface, possibly via hydrogen bonding. In addition, it has larger molecules than limonene and may be thus less likely to diffuse out from the silica matrix due to steric effects. Another possible explanation resides in the partition coefficient of limonene and solvent blue-35 between the hydrophilic domain and the outer oil phase, which may be different.

16. Characterisation of the Limonene Content Using FTIR

The concentration of limonene leached into dodecane was determined by FTIR spectroscopy. The limonene band used for concentration analysis depended on the concentrations of other components present. In the case of the unwashed solid, the 797 cm$^{-1}$ limonene band was used to determine the concentration, which corresponded to an encapsulation efficiency of 19 wt. %. For the washed solid, where the concentration of surfactant is considerably reduced, the 888 cm$^{-1}$ limonene band was used. An encapsulation efficiency of 5% was determined, indicating the extent to which limonene was also removed during the washing process. In terms of solid content, this corresponded to 1 wt % with respect to silica. Even though the IR technique is not as ideal as HPLC for analysing a mixture of component (as there is no mechanism available, such as retention time on a column, for separating the various components contributing to the IR spectrum), in situations where HPLC analysis is problematic (such as the presence of a high amount of surfactant), the IR can be used to get an approximate idea of the concentration in solution. The other species detected by FTIR as leached out from the particles in dodecane were Span 80, Tween 21, and possibly some dissolved silica.

17. Mechanism for Encapsulation of Hydrophobic Materials

Figure 26:
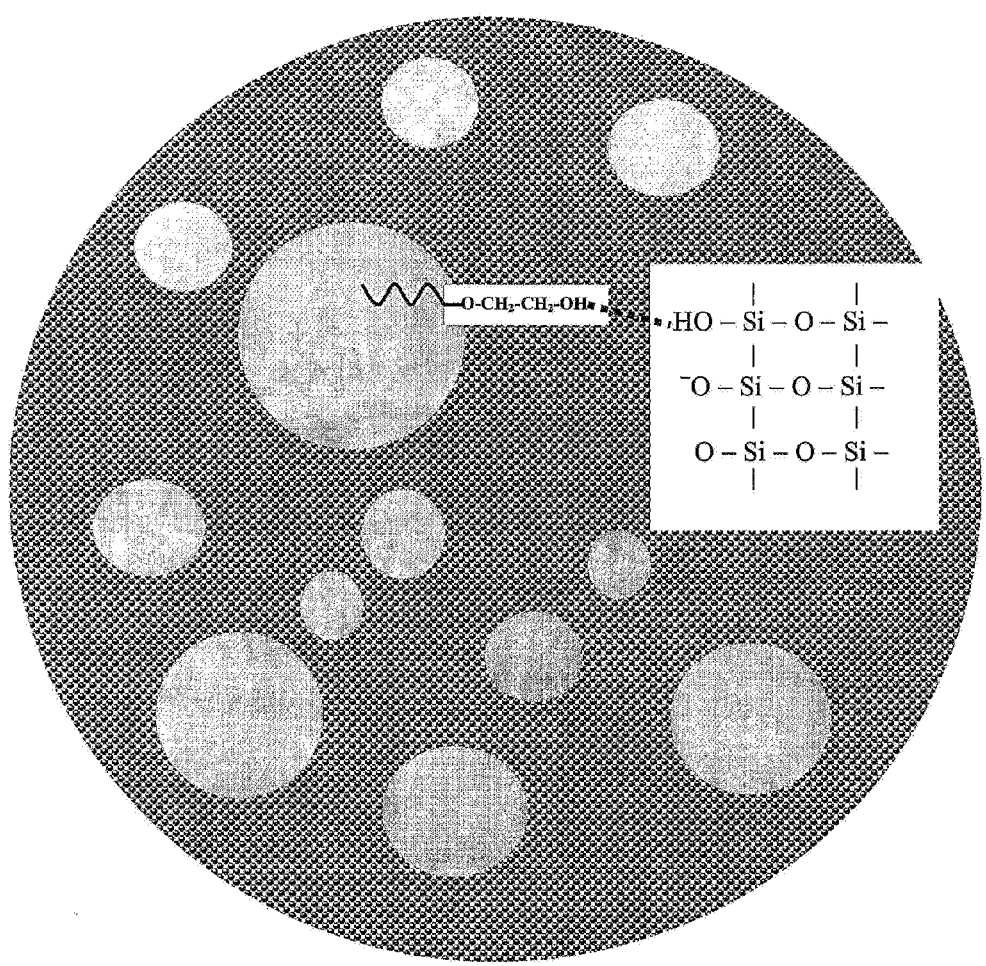
FIG. 26 is a diagram showing a schematic cross-sectional view of a typical single silica microsphere according to the present invention.

FIG. 26 displays a schematic cross-sectional view of a typical single silica microsphere showing oil droplets dispersed inside a silica matrix. The oil droplets are stabilised during synthesis by the presence of internal surfactant. The hydrophobic section of the internal surfactant (i.e. Tween 21) can dissolve in the internal oil or associate with the hydrophobic molecule such as SB-35, whereas the hydrophilic part (ethylene oxide) penetrates into the hydrophilic domain i.e. the silica matrix.

From section 2, we know that the maximum encapsulation efficiency was achieved using Tween 21. This suggests that only Tween surfactants with short PEG units are able to retain a high proportion of the oil in silica matrix. In other words it appears that the silica matrix can only accommodate a relatively small interaction with the PEG. When the PEG chain is too long, its interaction with the silicate species is too disruptive and leads to either the formation of a conduit leaking the internal oil to the outside oil phase or the expulsion of the internal oil droplet to the outer oil phase. In both cases this results in negligible encapsulation.

The perturbation of the internal structure of the silica was confirmed by the BET analysis which showed the formation of a drastically different porous network when Tween 21 was introduced into the system (see FIG. 20 and section 12).

As mentioned in section 3 and 4, the encapsulation efficiency also depended on the speed of gelation of the hydrolysed silicon phase and its viscosity. Both are dictated by the initial sol-gel chemistry and will dictate whether the internal oil droplets stay inside the particles or merge with the outer oil phase and thus lead to the formation of empty particles.

18. Replication of an Earlier Process

Figure 27:
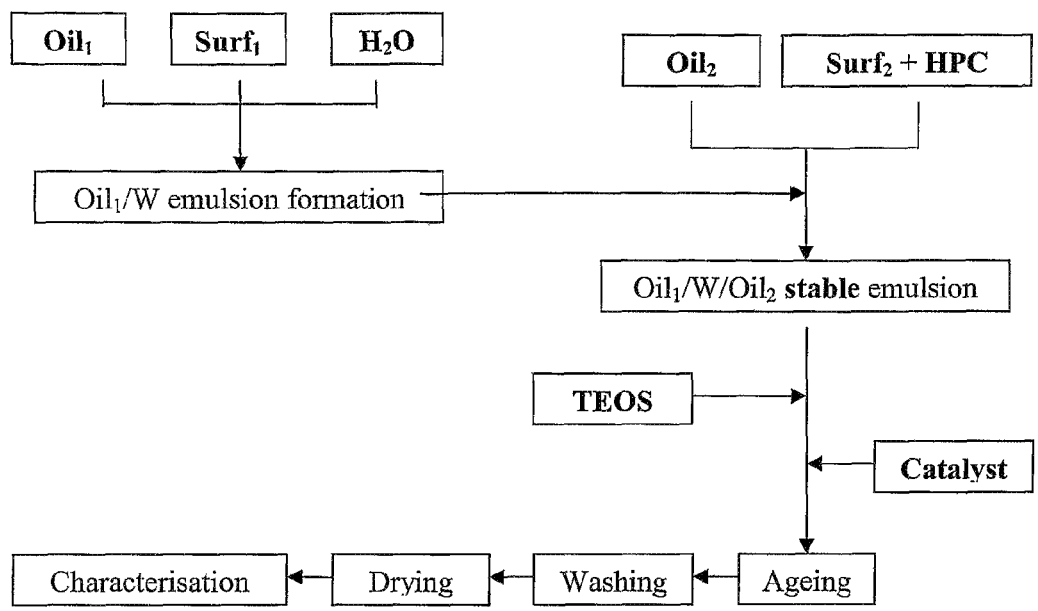
FIG. 27 is a flow chart of synthesis procedure for particles according to an earlier process.

FIG. 27 shows the flow chart of the earlier synthetic process. The main difference between the present process and the earlier process is that in the latter process a stable double emulsion must be formed before adding the silicon precursor. Another significant difference is the addition in the earlier process of HPC to the double emulsion system to increase the viscosity of the outer oil phase in order to improve the double emulsion stability. In the earlier process, only the use of a basic catalyst led to formation of spherical particles and the water:TEOS molar ratio needed to be strictly kept at 4. Furthermore, the volume ratio of internal phase ($O_1$/W) to outer oil phase needed to be less than 5%. Most importantly, the experimental process is very fragile as demonstrated by the lack of reproducibility (i.e. our inability to reproduce it despite numerous attempts).

The description in the literature of the earlier process does not fully detail the experimental procedure, and therefore the experimental procedure that was used in the present attempt to reproduce that work is described below. The internal phase was composed of 7 wt %. limonene, 3.5 wt % Tween 20 and 89.5 wt % water. This mixture was mixed using a shear mixer at 20500 rpm for 5 minutes to produce a stable $O_1$/W emulsion. In a second step, the primary $O_1$/W emulsion was slowly added to the outer oil phase, decyl alcohol, which contained 2 wt % Span 80 and 0.5 wt % HPC (MW: 370,000). This emulsion system was agitated at mild stirring speed (magnetically) for 30 minutes, then the amount of TEOS equivalent to the total water:TEOS molar ratio of 4 was added. The mixture was continuously stirred for 10 minutes, then 2.667 mol/L $NH_4OH$ was added with an ammonia to water volume ratio of 1:9. The final ammonia concentration in water phase was 0.267 mol/L. After reaction, sample was centrifuged at 6000 rpm for 15 min. The resulting particles were washed repeatedly with pure water, and dried at room temperature under nitrogen.

Figure 28:
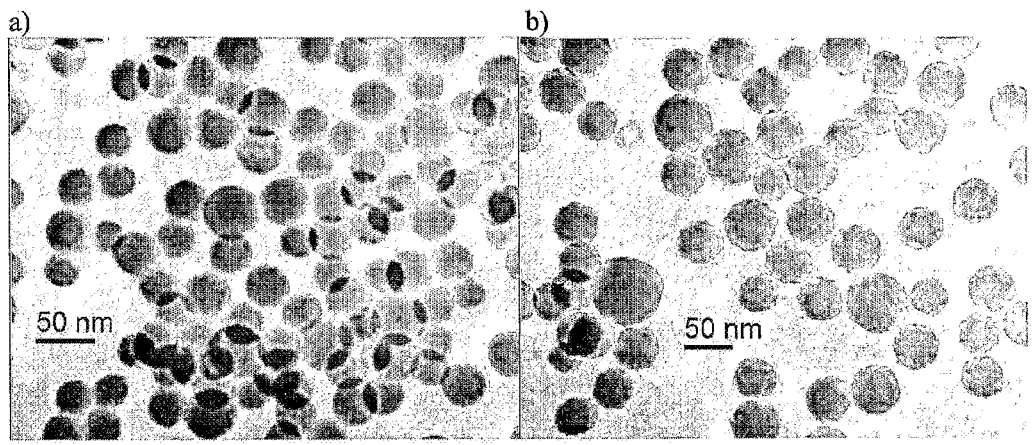
FIG. 28 shows TEM (transmission electron microscopy) images of silica particles produced by the present inventors according to the earlier process described in FIG. 27, with reaction time (a) 7 hrs, (b) 24 hrs.
Figure 29:
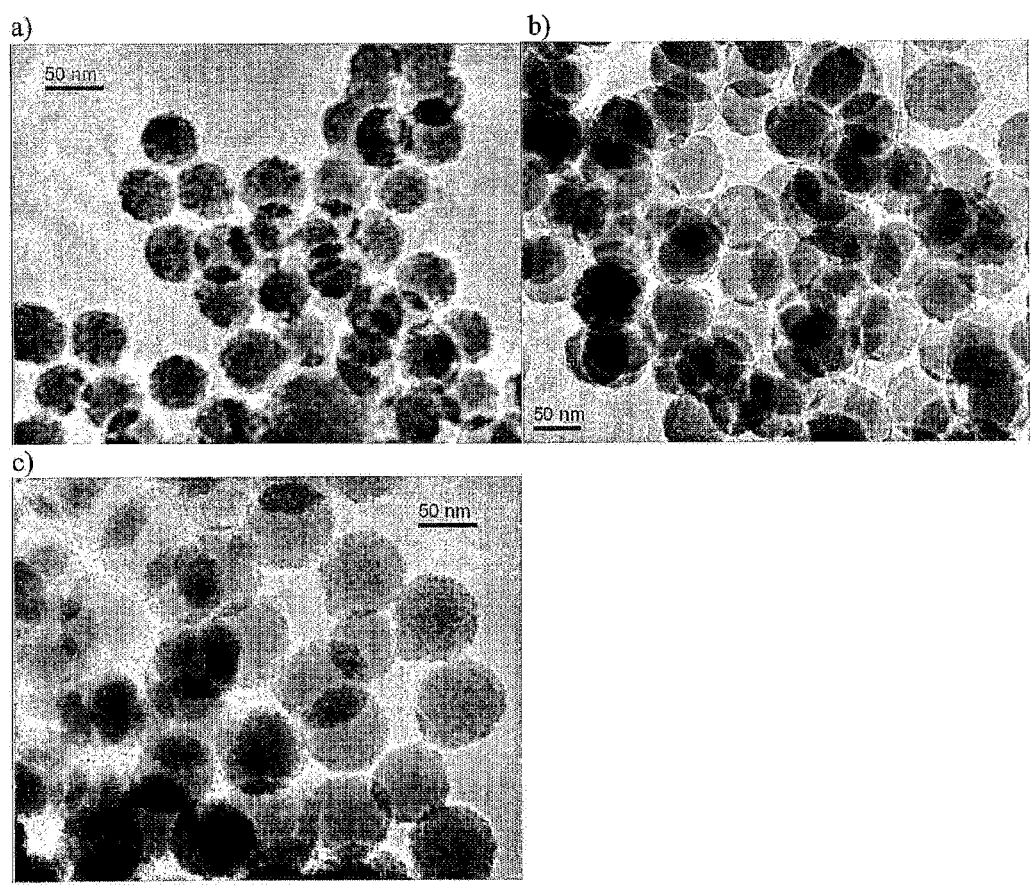
FIG. 29 shows TEM images of silica particles produced by the present inventors according to the earlier process described in FIG. 27, with reaction time 24 hours and stirring speed (a) 100 rpm, (b) 250 rpm, (c) 500 rpm during double emulsion formation.
Figure 30:
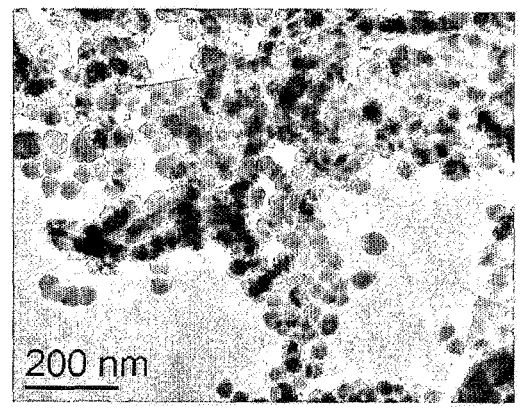
FIG. 30 shows TEM images of retinol doped silica particles produced by the present inventors according to the earlier process described in FIG. 27, with reaction time 24 hours and stirring speed 250 rpm during double emulsion formation.

FIG. 28 displays the TEM images of silica particles using the earlier process described in FIG. 27 with limonene as the internal oil phase. According to the earlier process, particles were extracted by centrifugation after a 7 hour reaction (FIG. 28a). However, it is generally believed that the reaction time for TEOS under basic conditions is at least 24 hours. This has been confirmed by the observation that more particles were formed in the supernatant several days after centrifugation. FIG. 28b shows the particles after a 24 hour reaction time. Nanoparticles with a size range of 50-60 nm diameter were produced for both experiments, which suggest there was no double emulsion formed in the present case, but rather a single water-in-oil emulsion system. During the course of the experiment, we also found that the $Oil_1$/W emulsion was reasonably stable, with no phase separation observed for at least several hours. This suggested that agitation might play a major role for formation of a stable double emulsion. Hence, we investigated three stirring speeds (100, 250 and 500 rpm) to produce particles. The corresponding TEM images are shown in FIG. 29 a-c. Again, nanoparticles with size diameter about 60 nm were produced regardless of the stirring speed. After that, we hypothesised that micron sized particles may only be produced if retinol is employed as the internal oil phase. However, as observed in FIG. 30, which displays the TEM image of silica particles with retinol as the internal oil phase, similar sized particles (but less spherical) were produced as above.

Figure 31:
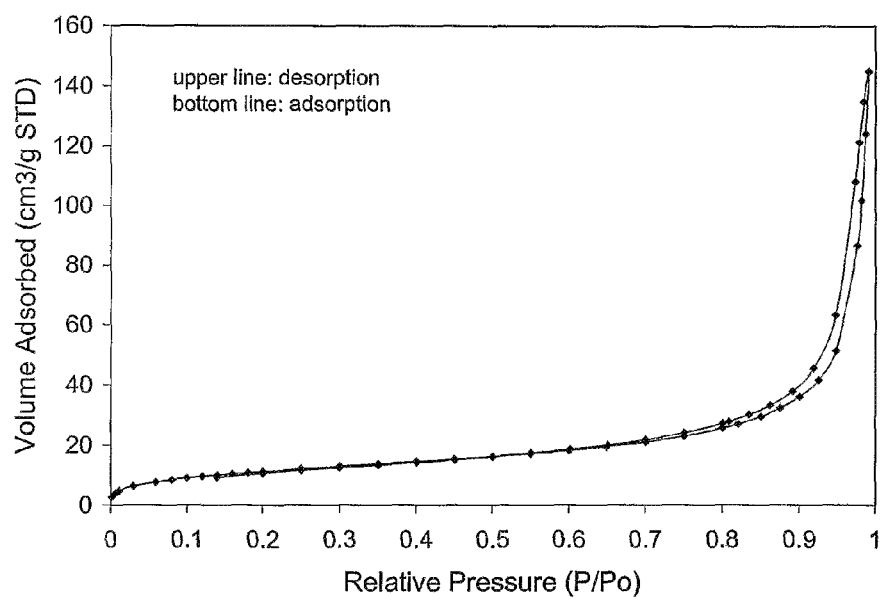
FIG. 31 shows sorption isotherms of silica particles produced by the present inventors according to the earlier process described in FIG. 27.

FIG. 31 shows the sorption isotherm diagram for particles produced according to the earlier process described in FIG. 27. The BET surface area was 42 $m^2$/g, suggesting the formation of dense particles. The porosity observed (median pore radius of 21.6 nm) is due to the interparticle porosity. This further confirmed the difference between the two processes. The internal structures of both silica matrices are drastically different.

Figure 32:
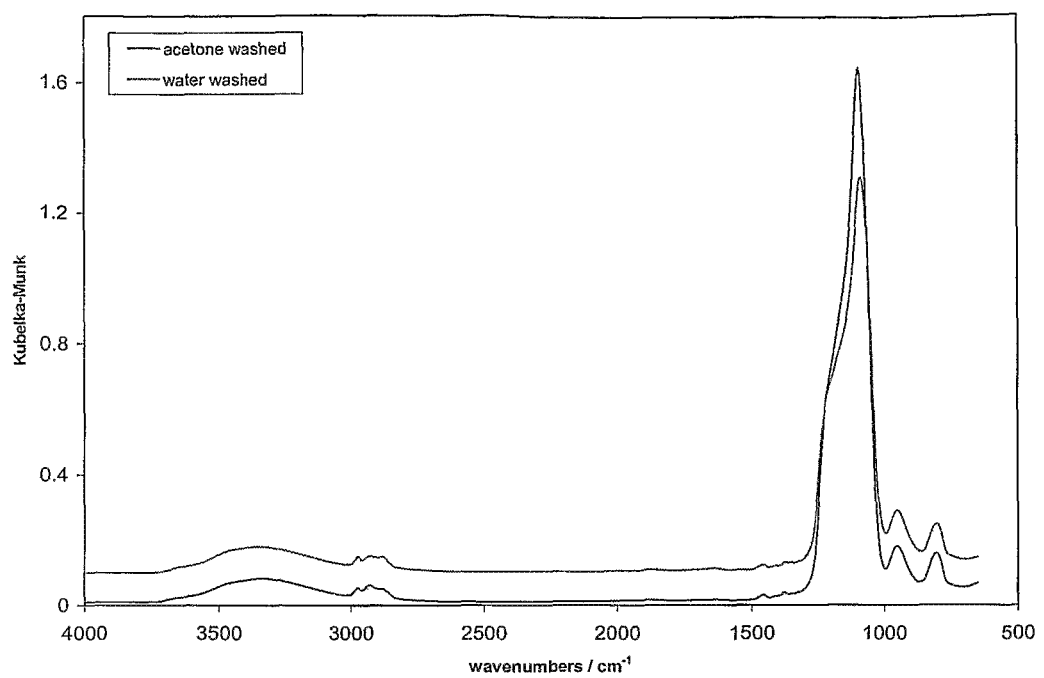
FIG. 32 shows DRIFT (diffuse reflectance infra-red Fourier transform) spectra (650-4000 $cm^{-1}$) of the sample of FIG. 31.

The FTIR spectra of the nanoparticles made by the earlier process, washed either by acetone or by water, were measured to determine if there was evidence of hydroxypropyl cellulose adsorbed on the particle surface. The spectra were measured of samples diluted to 2 wt. % in KBr, using a DRIFT cell. The full IR spectra of the samples made by the earlier process are shown in FIG. 32. There was very little difference between the two samples.

Figure 33:
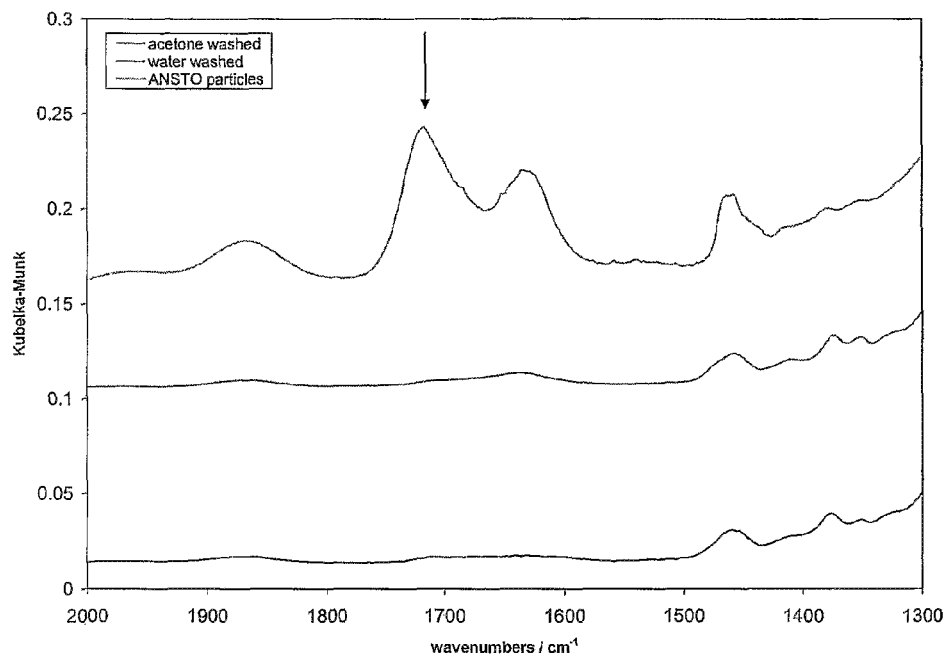
FIG. 33 shows (a) DRIFT spectra (1300-2000 $cm^{-1}$) of the samples of FIG. 31 and of particles according to the present invention ("ANSTO particles"); and (b) DRIFT spectra (2700-3100 $cm^{-1}$) of the samples of FIG. 31, HPC and particles according to the present invention.
Figure 33:
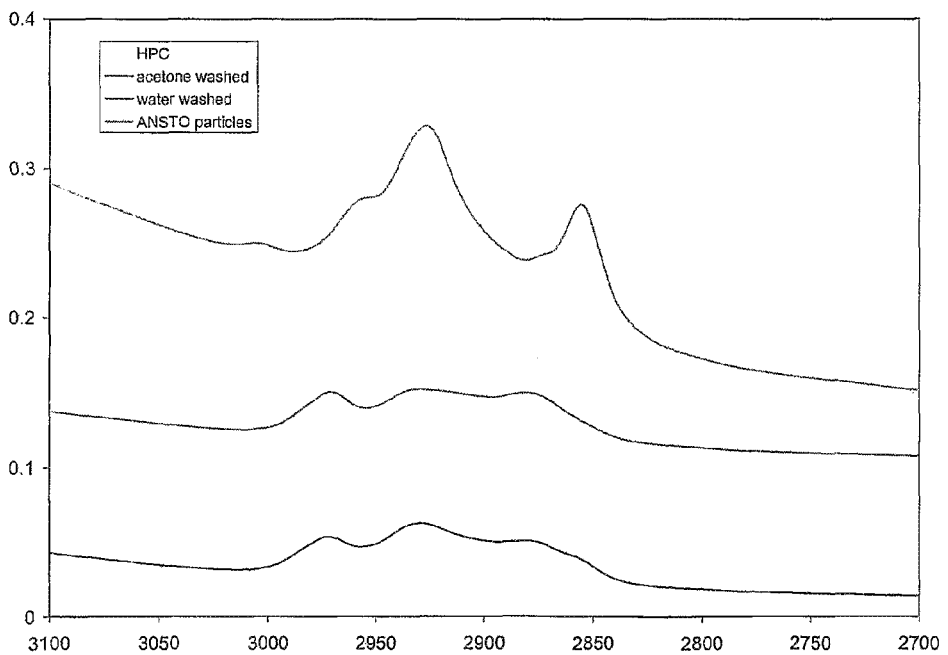

FIG. 33 (a) shows spectra of the sample prepared according to the earlier process as well as a sample double emulsion particles produced by the process of the present invention. The band at about 1740 $cm^{-1}$ marked with an arrow in the spectrum of the particles of the present invention is present in both Span 80 and Tween 21 and is due to C=O bonds in the surfactants. It was not observed in either of the particles made by the earlier process. Similarly, the spectra in the C-H region (2700-3100 $cm^{-1}$) are compared in FIG. 33 (b), which also includes the spectrum of HPC. The prominent C-H bands in the particles made by the earlier process and in HPC are at 2972, 2930 and 2881 $cm^{-1}$, indicating a significant amount of $CH_3$ groups present as well as $CH_2$. However, the spectrum of the particles of the present invention is dominated by two bands at 2926 and 2855 $cm^{-1}$, which is indicative of long —$CH_2$— chains—as observed in both Span 80 and Tween 21. These observations suggest that the majority of organic material absorbed on the particles made by the earlier process was due to HPC, whereas that on the surface of the particles of the present invention was due to either Span 80 or Tween 21. Analysis of the band areas shows that the amount of HPC absorbed on the water-washed sample was virtually identical to that of the acetone sample.

Figure 34:
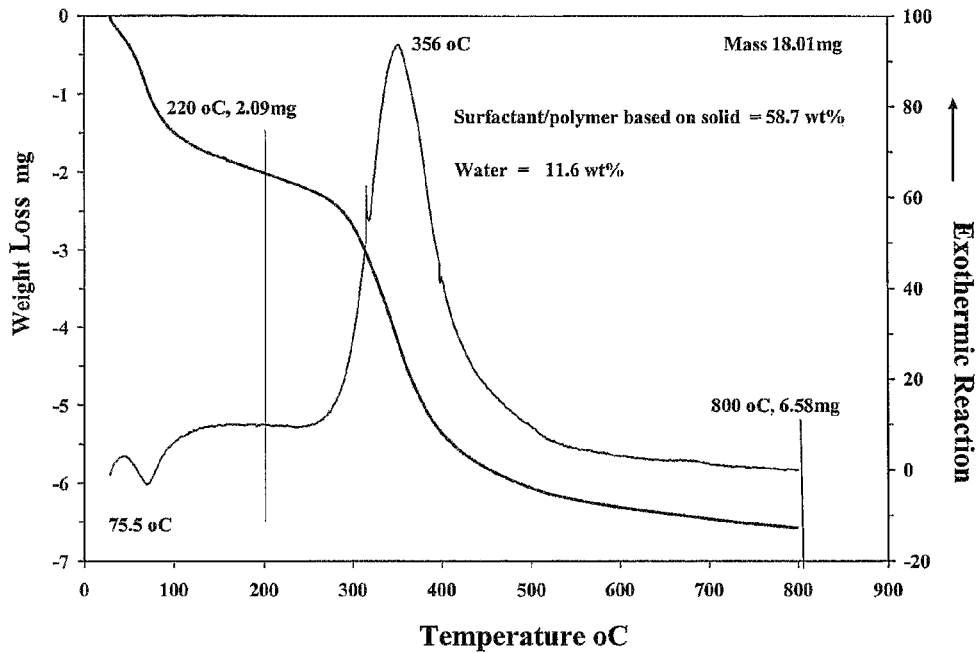
FIG. 34 shows TGA and DTA results for estimation of surfactant residue on the surface of silica particles of FIG. 31, (a) acetone washed, (b) water washed.
Figure 34:
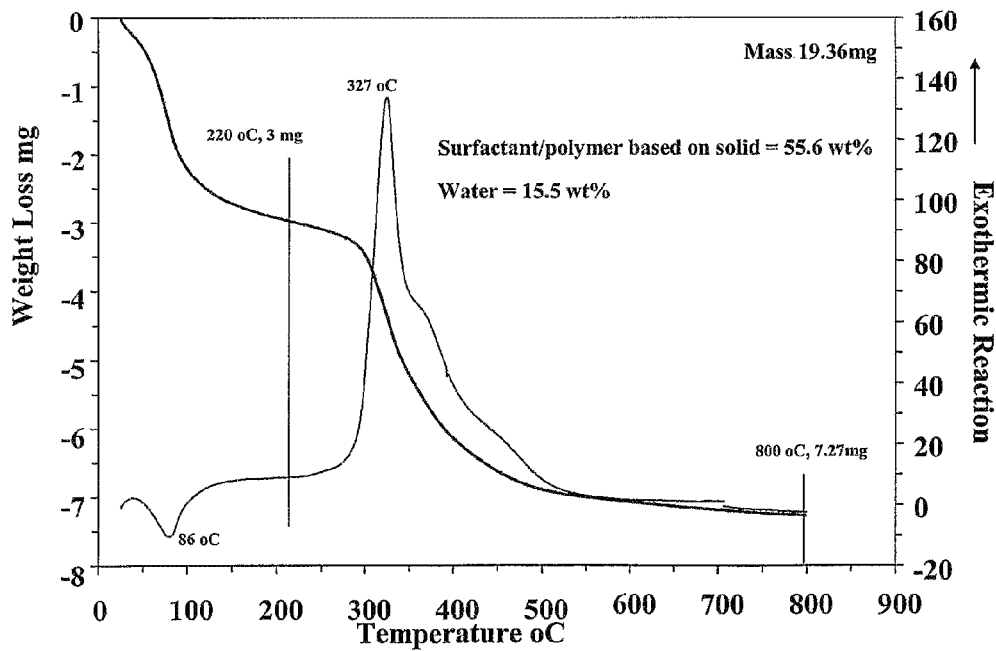

FIG. 34(a) shows the TGA/DTA results of acetone washed particles produced by the earlier process described in FIG. 27. The water and solvent were evaporated before 200° C., and the volatile content was 11.6 wt %. The exothermic peak at 356° C. corresponds to the decomposition of the surfactant and polymer. The percentage of these organic materials was 59 wt % of the dry weight (i.e. neglecting the mass of water from the calculation). The results for water washed particles are displayed in FIG. 34b. The initial mass of sample used for the analysis was 19.36 mg. The exothermic peak occurred at 327° C. The water content was 15.5 wt % of the product, while the surfactant and polymer represented 55 wt % of the dry weight.

Figure 35:
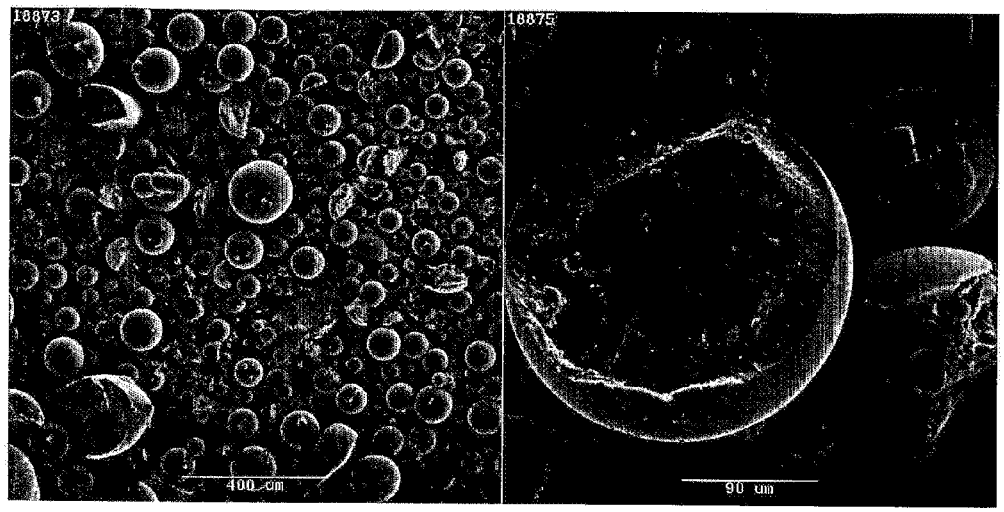
FIG. 35 shows SEM images of silica particles synthesised at different pH: (a) 1.640; (b) 1.000; (c) 0.602; (d) 0.301, with other experimental conditions as described for the typical synthesis.
Figure 35:
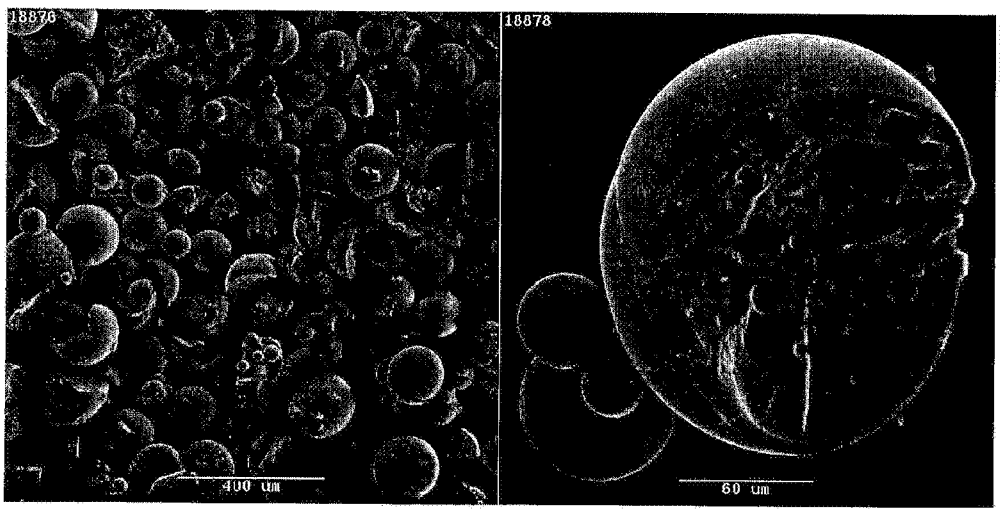
Figure 35:
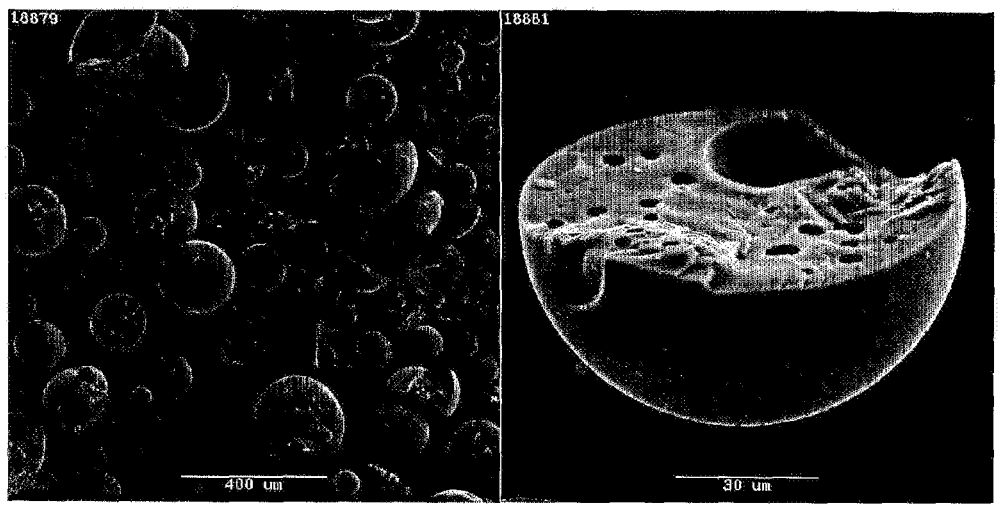
Figure 35:
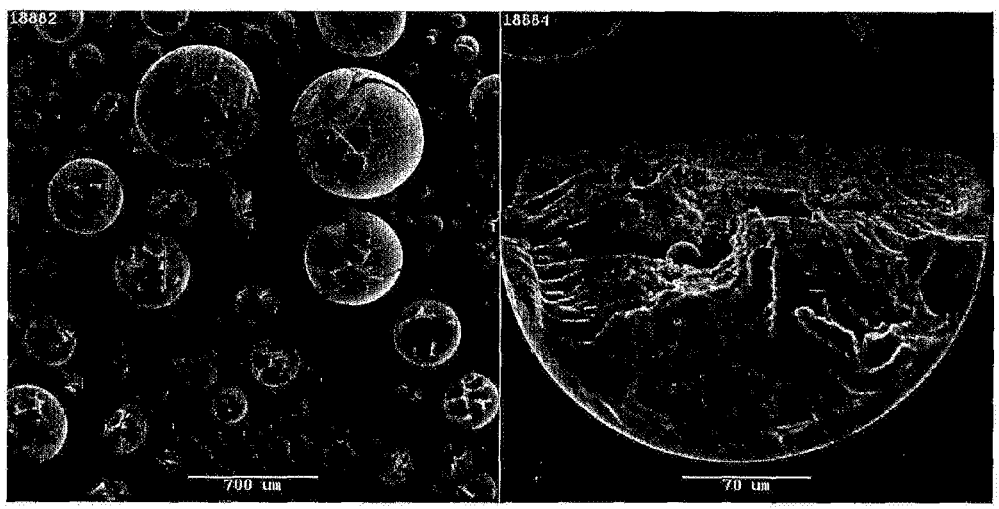
Figure 36:
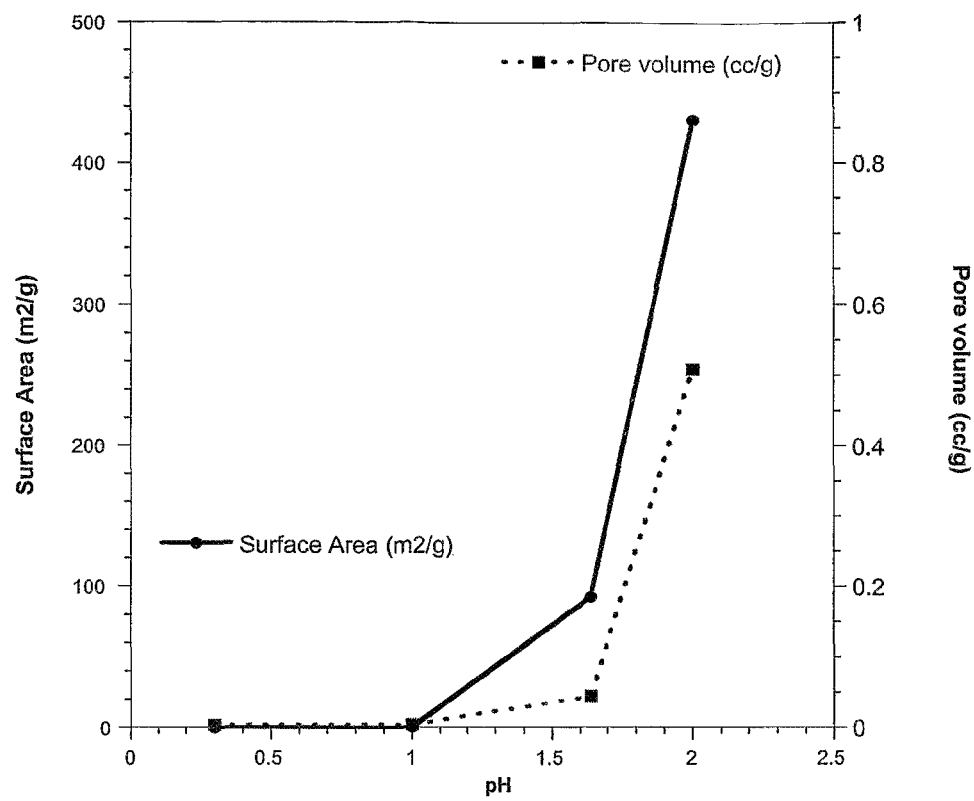
FIG. 36 shows BET surface area results as a function of pH.

19 Influence of pH pH may have a significant effect on the particle properties. Under the typical synthesis conditions described earlier, at pH 2, the particles are in the size range 10-150 µm. When the pH is decreased from 2 to 0.301, the particle size increases significantly, as well as the size distribution (i.e. polydispersity). FIG. 35 shows the SEM images of particles synthesised at pH 1.64, 1.00, 0.602, and 0.301. From pH 1.64 to 0.602, particles were in the size range of 50-230 µm. However, the particle size increased to 80-700 µm at pH 0.301. The BET results as a function of pH are shown in FIG. 36. The surface area decreased drastically from approx. 430 $m^2/g$ to approx. 92 $m^2/g$ as the pH decreased from pH 2.00 to pH 1.64. When pH was 1.00, the particles became more dense and their surface area was about 0.3 $m^2/g$. The BET surface area was only 0.01 $m^2/g$ at pH 0.301. The pore volume also decreased with pH from 0.51 $cm^3/g$ at pH 2 to about 0.045 $cm^3/g$ at pH 1.64, and down to 0.005 $cm^3/g$ at pH 1.00 and 0.004 $cm^3/g$ at pH 0.301. The dye (solvent blue-35) encapsulation efficiency also decreased with decreasing pH.

Figure 37:
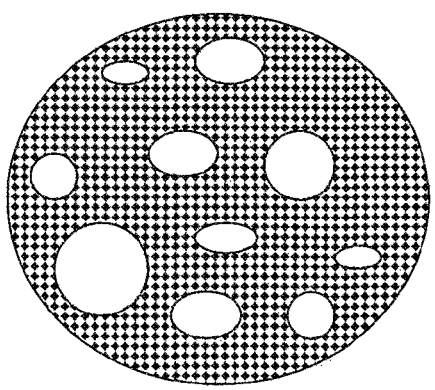
FIG. 37 is a diagrammatic representation of a particle according to the present invention.

FIG. 37 shows a diagram of a particle having internal cavities, such as those of the present invention. In this figure, the squares represent the matrix, which is sufficiently porous to allow the hydrophobic material to diffuse from the cavities to the outside of the particle. The BET measurement concerns the small pores between the squares (1-20 nm). By contrast, SEM is capable of measuring the larger cavities (1-100 microns=1000-100000 nm).

The minimum of the condensation rate of silicon alkoxide is observed at pH=2 [Scherer, Brinker Sol-Gel Science and Technology, Academic Science 1990, Chapter 3 page 213].

Thus when the pH decreases to pH=1 or lower, the condensation rate increases, leading to an increase in particle size. From the point of view of the internal structure, although the exact mechanisms governing the particle formation remain largely unknown, the inventors postulate that the change of pH leads to a change in the nature of the interaction between the Tween 21 (i.e. the internal, or first, surfactant) and the silica matrix. Indeed, pH=2 also corresponds to the point of zero charge of silica: above pH=2, the surface of the silicate species are negatively charged, and below pH=2 the silicate species (i.e. the hydrolysed oligomers) are positively charged. Although the surfactants are nonionic, a change in the surface charge of the silicate could lead to a repulsion or perturbation of the Van der Waals interaction between the surfactant and the silica which might result in an expulsion of the oil droplets outside of the sphere during formation. Although no significant changes with pH were observed by SEM in the internal structure of the spheres, the fact that the encapsulation efficiency decreased with decreasing pH tends to confirm this hypothesis. Furthermore, the decrease in pore volume and surface area, which corresponds to a densification of the spheres, suggests the importance of the surfactant-silicate interaction on the formation of the internal porosity. The nitrogen adsorption-desorption isotherms revealed that the structure was transformed from a largely mesoporous solid at pH=2, to a microporous solid at pH=1.64, and to a non-porous solid at pH=1.

1. Investigation of Internal Hydrophilic Surfactant

A range of additional surfactants was tested to better understand the influence of the nature of the internal surfactant (i.e. the first surfactant) on the particle morphology and oil encapsulation efficiency. The surfactants used were: polyoxyethylene 4 lauryl ether, $C_{12}H_{25}(OCH_2CH_2)_4OH$ (Brij30, Sigma, MW 362, HLB 9.7); nonylphenol polyethylene glycol, $C_9H_{19}C_6H_4(OCH_2CH_2)_nOH$, NP-5 (Sigma, n=5, MW 440, HLB 10.0); NP-6 (Sigma, n=6, MW 485, HLB 10.9); Tergitol NP-9 (Fluka, n=9-10, MW 630, HLB 13.0); octylphenol polyethylene glycol $C_8H_{17}C_6H_4(OCH_2CH_2)_mOH$, Triton X-114 (Aldrich, m=7-8, MW 537, HLB 12.4), Triton X-100 (Sigma, m≈10, MW 646, HLB 13.5). These surfactants were all white, viscous liquids and contained less than 0.12 wt. % of water, as determined by Karl Fisher titration. Other surfactants investigated were POE (4) sorbitan monostearate (Tween 61: MW 606, HLB 9.6) and POE (5) sorbitan monooleate (Tween 81: MW 650, HLB 10).

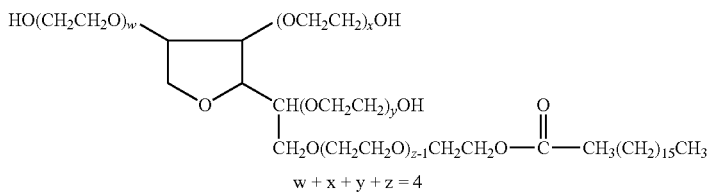

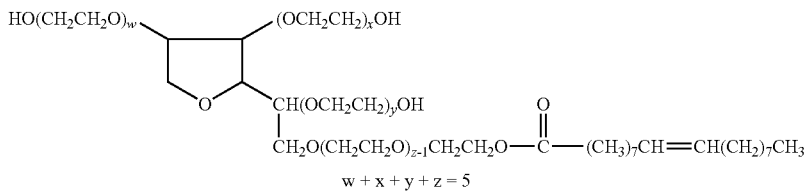

The synthesis procedure and the amount of each material are according to the "typical synthesis conditions" described earlier, except where stated. The encapsulation efficiencies and particles morphology results are summarised in tables 6 and 7.

Previous studies described above show that the internal surfactant type and concentration have significant effects on the particle morphology and encapsulation of the active species. However, only a few surfactants had been trialled previously, and the best results were obtained by using Tween 21, which has HLB 13.3 and 4 PEO units. In this part of the work, other types of non-ionic surfactants with HLB values between 9.6 and 13.5 and PEO units less than 10 were tested.

Figure 38:
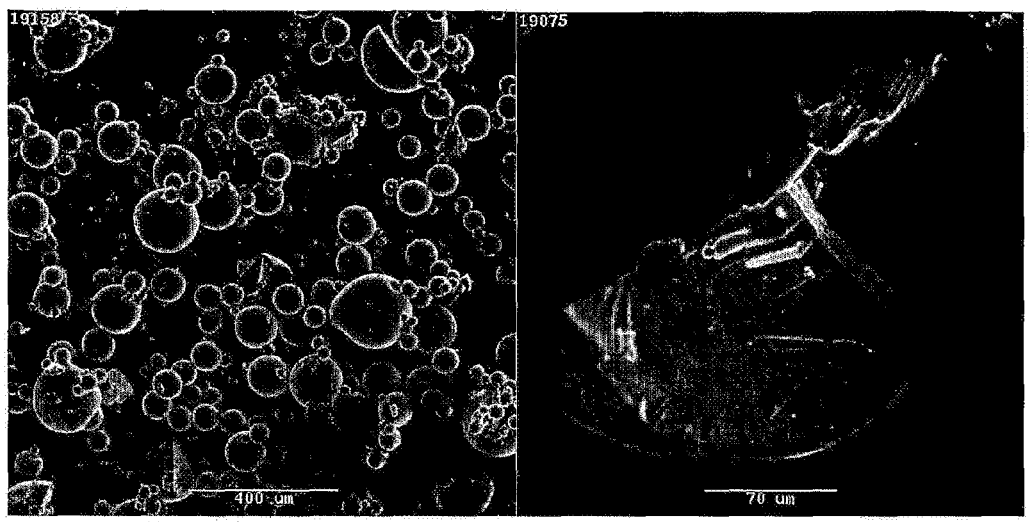
FIG. 38 shows SEM images of silica microparticles made using various internal surfactants: (a) NP-5; (b) NP-6; (c) NP-9; (d) Triton X-100; (e) Triton X-114; (f) Brij 30.
Figure 38:
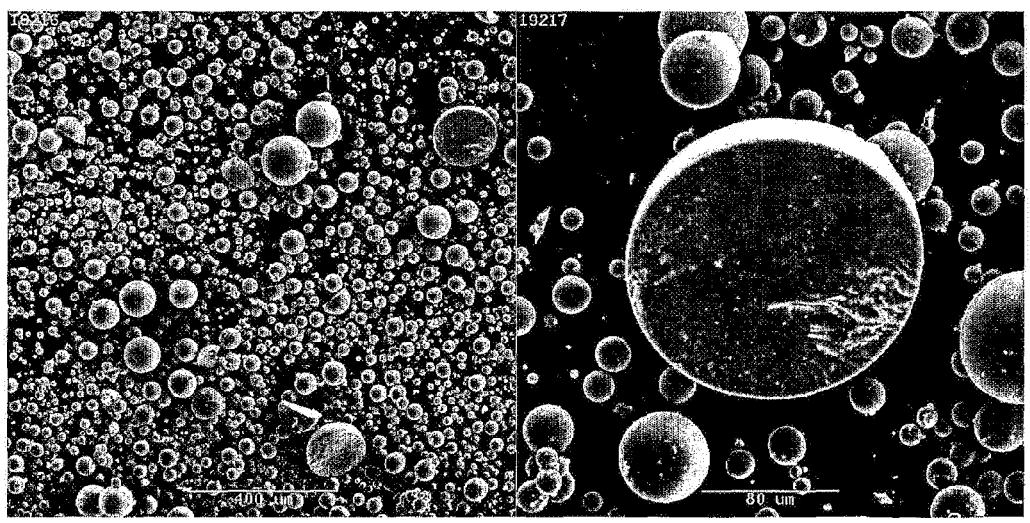
Figure 38:
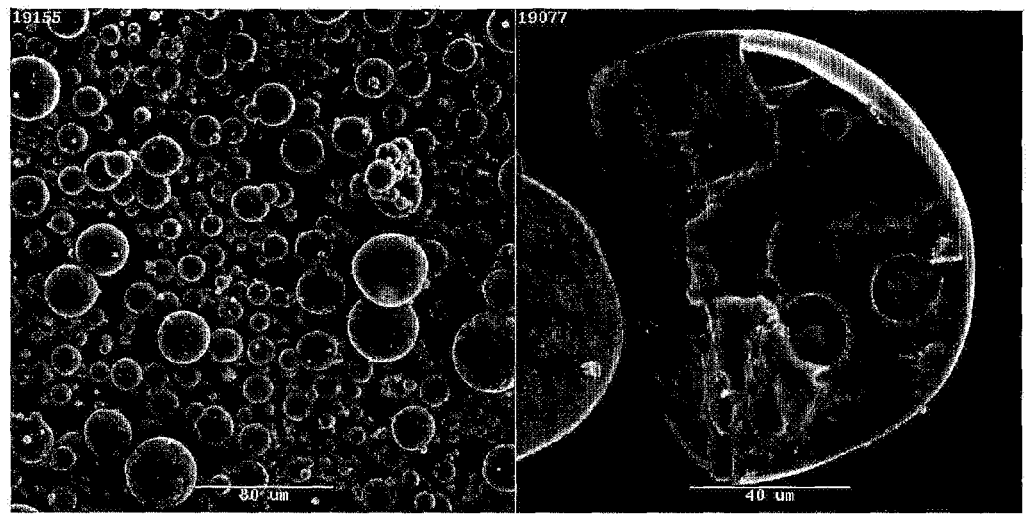
Figure 38:
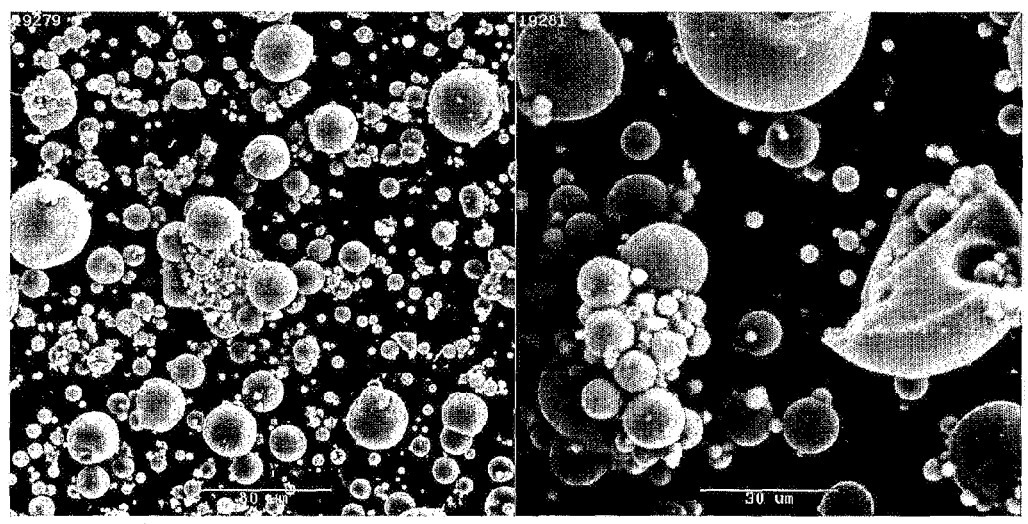
Figure 38:
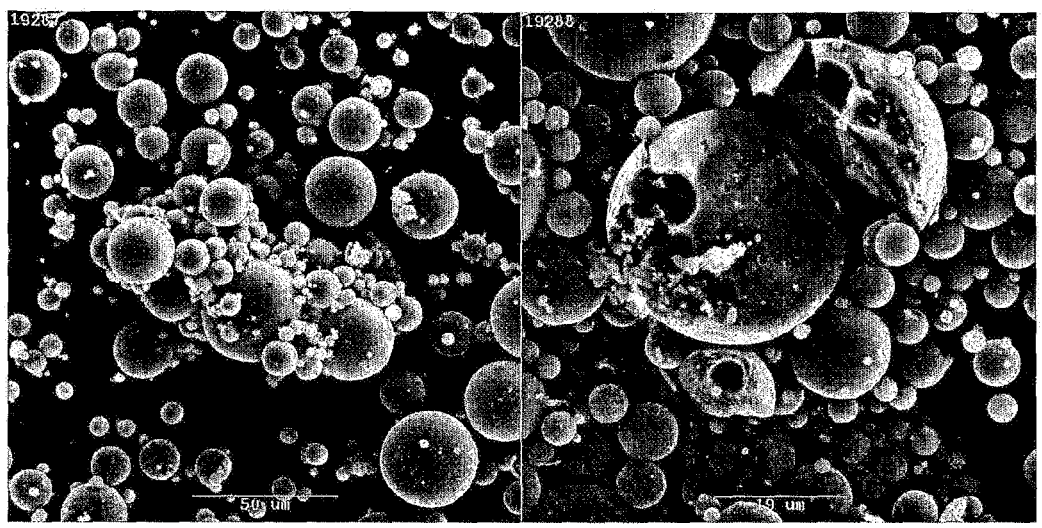
Figure 38:
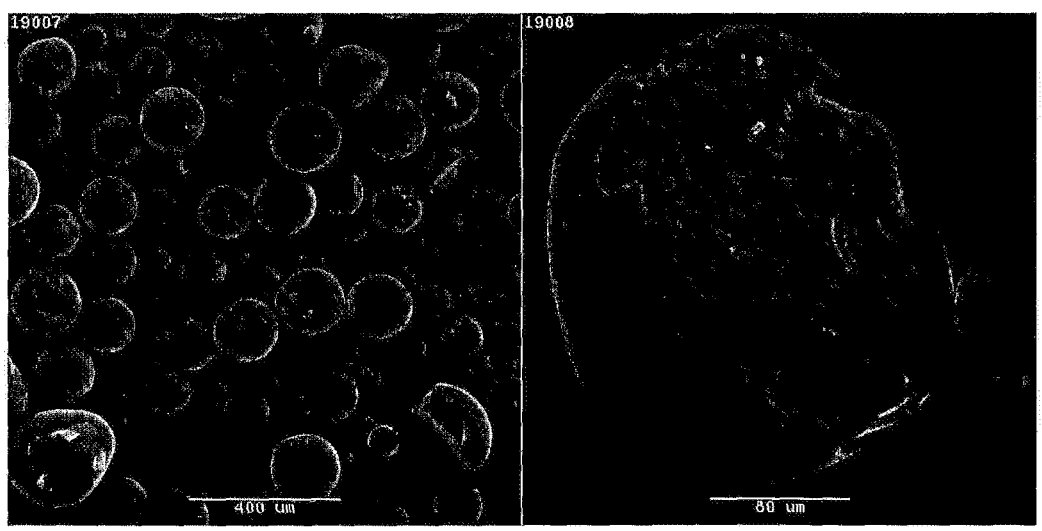

Compared with the encapsulation efficiency of solvent blue using Tween 21 (approximately 38%), the encapsulation efficiencies were low, ranging from 0.5% to 1.8%, when using NP-5 or NP-6 as internal surfactant. Spherical particles were produced, but the particles did not exhibit vacuoles inside the silica matrices (FIG. 38). In addition, the encapsulation efficiency increased to about 12-22% using NP-9 as the internal surfactant. The encapsulation efficiency when using Triton X-100 and Triton X-114 was about 10%, while only a slight amount of dye was encapsulated using Brij 30.

A possible reason for the low encapsulation efficiency observed for the NP, Triton and Brij series relates to the molecular structure of these surfactants, which are significantly different from Tween 21.

Tween 21: $C_{20}H_{38}O_7(CH_2CH_2O)_3$ w + x + y + z = 4

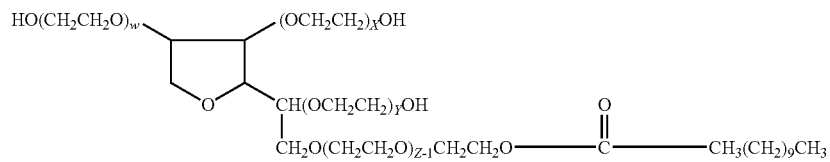

Tween 21 (structure shown above) has a short hydrophobic tail and a big hydrophilic head with branched PEO units, whereas the NP, Triton and Brij molecules consist of long linear chains containing hydrophilic and hydrophobic parts. If one assumes that the surfactant is associated with the hydrophilic domain (the hydrolysed silica precursor together with water) by its PEO units, then it appears likely that the Tween structure can form micelles more easily, and the micelles formed may be more stable because of the presence of more than one "anchor" on a single surfactant molecule. By contrast, molecules of the other surfactants studied are likely to adopt a linear configuration, and thus the micelles formed using these surfactants may be expected not to be stable. As a result, the molecular structure of the Tween surfactant is expected to favour the formation of spherical internal compartments and so enable the encapsulation of oil. However, the length of the PEO anchors on Tween surfactant should not be too long, as in the case of Tween 20 or Tween 80, as this appears to lead to low encapsulation of oil.

Tween 61 and Tween 81 have a similar molecular structure to Tween 21 (shown above) and slightly lower HLB values. The encapsulation efficiencies of the Tween 61 system were slightly higher than those of Tween 21, while the encapsulation efficiencies of the Tween 81 system were lower than with Tween 21. In contrast to the systems of NP, Triton and Brij surfactants, the high encapsulation efficiency of the Tween surfactants suggests that oil droplets are encapsulated inside the observed cavities, which can be seen in FIG. 39. The concentration of Tween 61 appears to have no significant influence on the encapsulation efficiency, while the encapsulation efficiency was decreased to some extent with increasing the amount of Tween 81.

The particle size decreased with increasing the amount of internal surfactant, except in the case of Brij 30. This result is unexpected because the internal surfactant acts on the $Oil_1$/Water emulsion, i.e. the dispersion of droplets of oil in the hydrophilic domain and thus would not be expected to influence the overall droplet size of the hydrophilic entities, which shape and size would be expected only to be affected by the outer (second) surfactant properties. These results suggest that the two surfactants may interact with each other. Hypothetically, as the concentration of internal surfactant increases, an increasing part of the surfactant is not involved in the stabilisation of the oil droplets but interacts with the outer surfactant walls. It is known that mixture of surfactants can increase the stiffness of micellar walls and thus stabilise emulsion phase. In terms of particle size this might translate to production of smaller particles.

Figure 40:
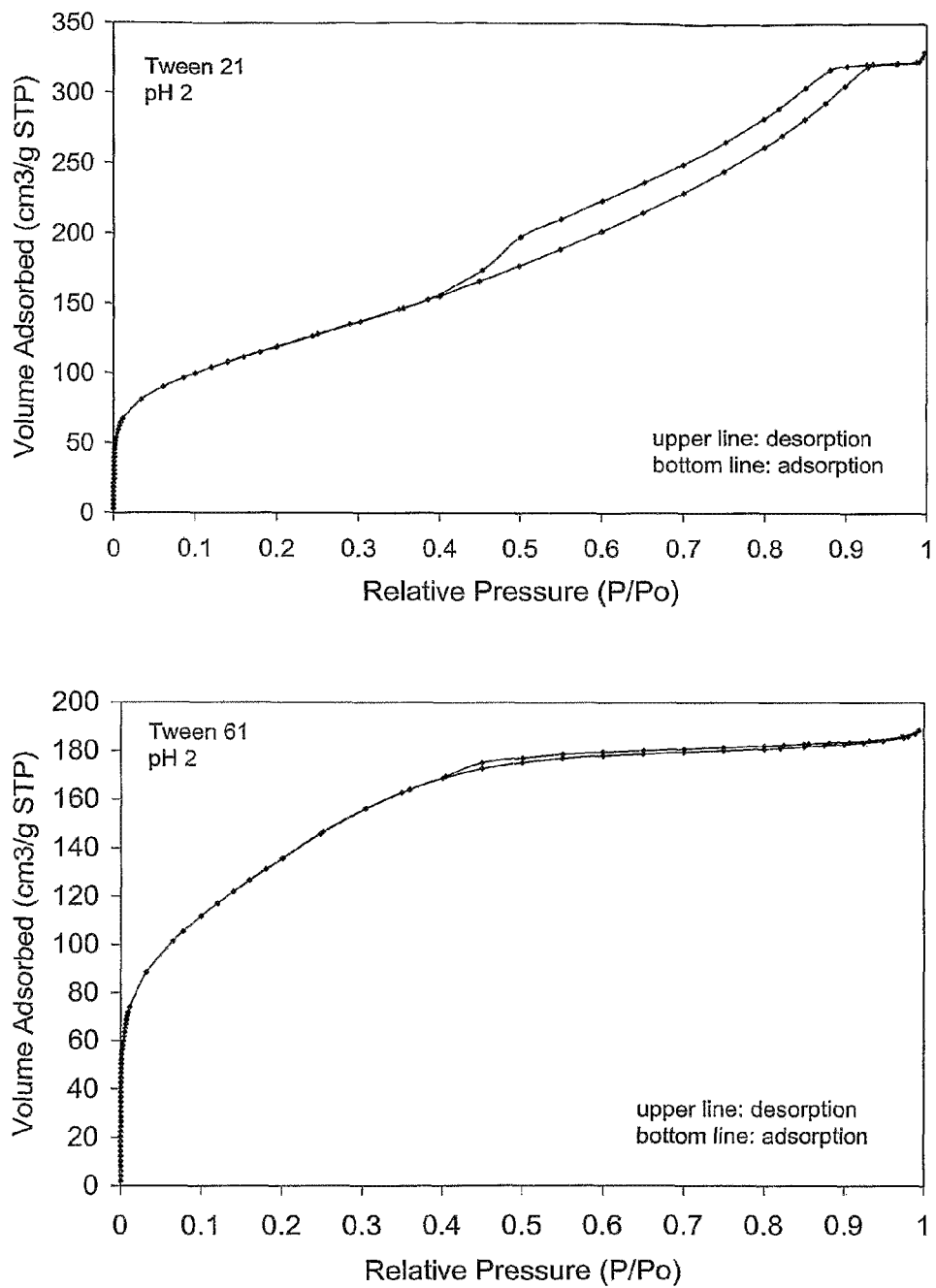
FIG. 40 shows sorption isotherms of silica particles produced with different internal surfactants.
Figure 40:
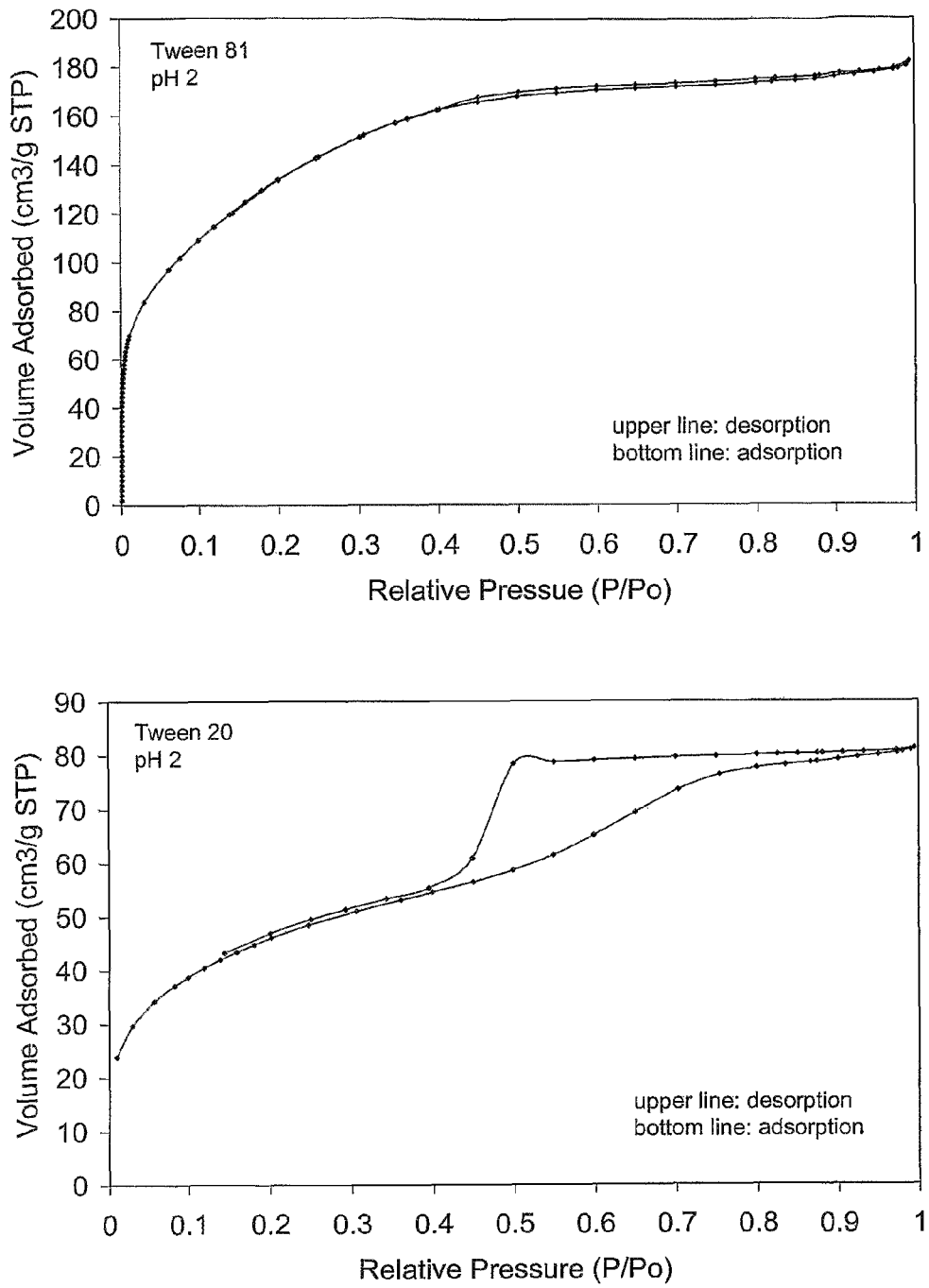
Figure 40:
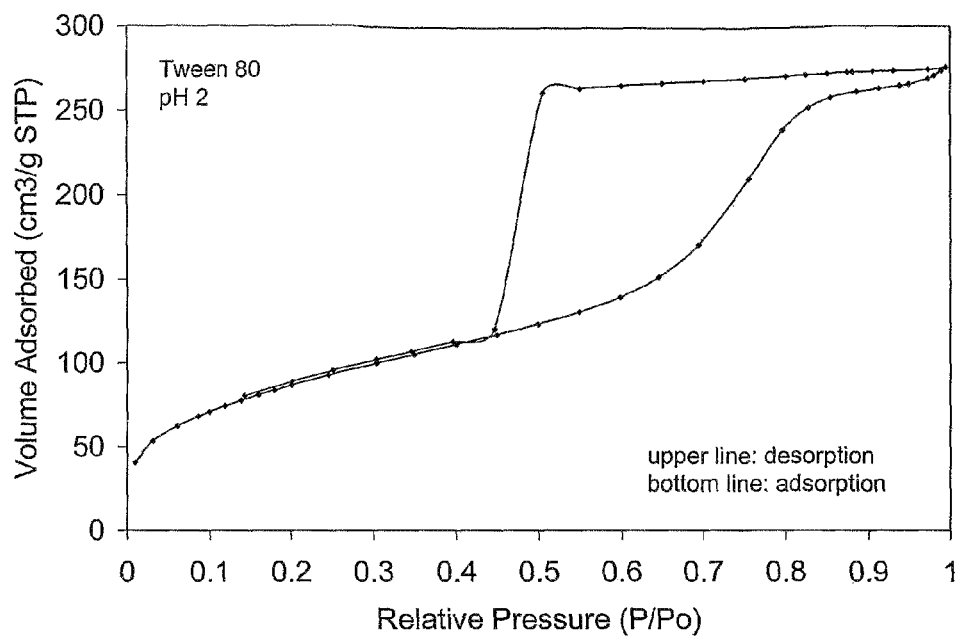
Figure 41:
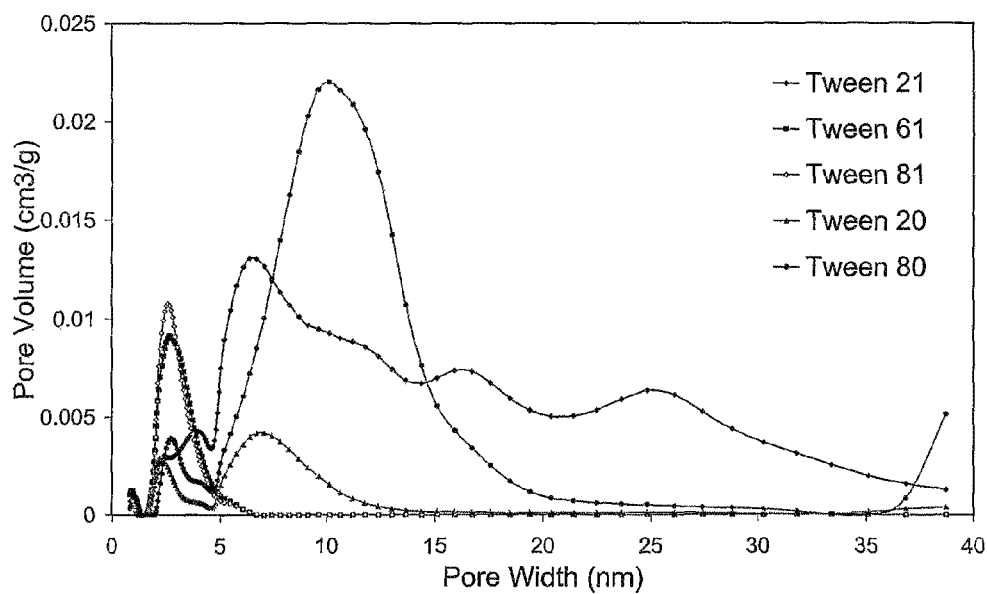
FIG. 41 shows pore size distributions of silica particles produced with different internal surfactants using a DFT (density-functional theory) model.

The BET results are displayed in Table 8 and corresponding sorption isotherms are shown in FIG. 40. FIG. 41 shows the corresponding pore size distribution calculated using the DFT model. FIG. 40 shows that the nature of the internal surfactant influences the porous structure of the silica matrix. All isotherms reveal the presence of a microporous and mesoporous region. Isotherms from particles made using Tween 21, 61 and 81 exhibit a small hysteresis in the mesoporous region, suggesting homogeneous pore structure. Particles made using Tween 61 and 81 exhibited a monodispersed pore size. In contrast particles made using Tween 80 and 20 displayed an isotherm with extensive hysteresis in the mesoporous region that suggests a "bottle-neck" type pore structure. These different morphologies obtained using the different surfactants confirm the important role of the internal surfactant in the internal morphology of the spheres and, as described below, in their release behaviour. The absence of correlation between the EE (encapsulation efficiency) and the internal structure of the silica matrix may be explained by the fact that the nitrogen adsorption experiments are characterising the porous structure on the nanometer scale, thus neglecting the macroporosity which is apparent in the SEM micrographs. As discussed above the macroporosity, i.e. the vacuoles, are the reservoir for the oil encapsulation and their presence can be linked to a higher encapsulation efficiency. The diameter of the vacuoles may be from 10 nm to 50 microns or between 50 nm to 50 microns, for example.

2. Influence of the Quantity of Internal Oil

The "typical synthesis conditions" were employed, and the results are displayed in Table 9. In general, increasing the internal oil quantity decreased the encapsulation efficiency and led to the formation of broken particles.

In a typical synthesis, 58.123 mmol TMOS and 0.714 mL limonene were used. If it is assumed that the sol-gel reaction yield was 100% efficient, 3.492 g of silica would be produced (MW of SiO$_2$ is 60.0843). If it is assumed that the density of the pure silica matrix is 2.0 g/cm$^3$, the oil-to-silica volume ratio would be approximately 15 vol. % for 0.714 mL limonene (encapsulation efficiency of SB-35: 38%), and about 25 vol. % for 1.428 mL limonene (encapsulation efficiency of SB-35: 31%). The BJH average pore volume for particles made using Tween 61 under typical synthesis conditions is 0.18 cm$^3$/g, and therefore the pore volume to silica volume ratio is about 22%. These results suggest that there may be a threshold value of internal oil-to-silica volume ratio, above which silica microparticles are easily broken. For instance, from table 9 doubling the internal quantities of oil leads to particle breakage. It follows that the particles may be more fragile with increasing volume proportion of vacuoles.

If this occurs, the internal oil would be leached into the outer oil phase and the encapsulation efficiency would be decreased. Other factors such as the viscosity of the outer oil phase and the shear force during stirring may be adjusted in order to reduce the likelihood of particle breakage.

3. Influence of Ageing Time

Figure 42:
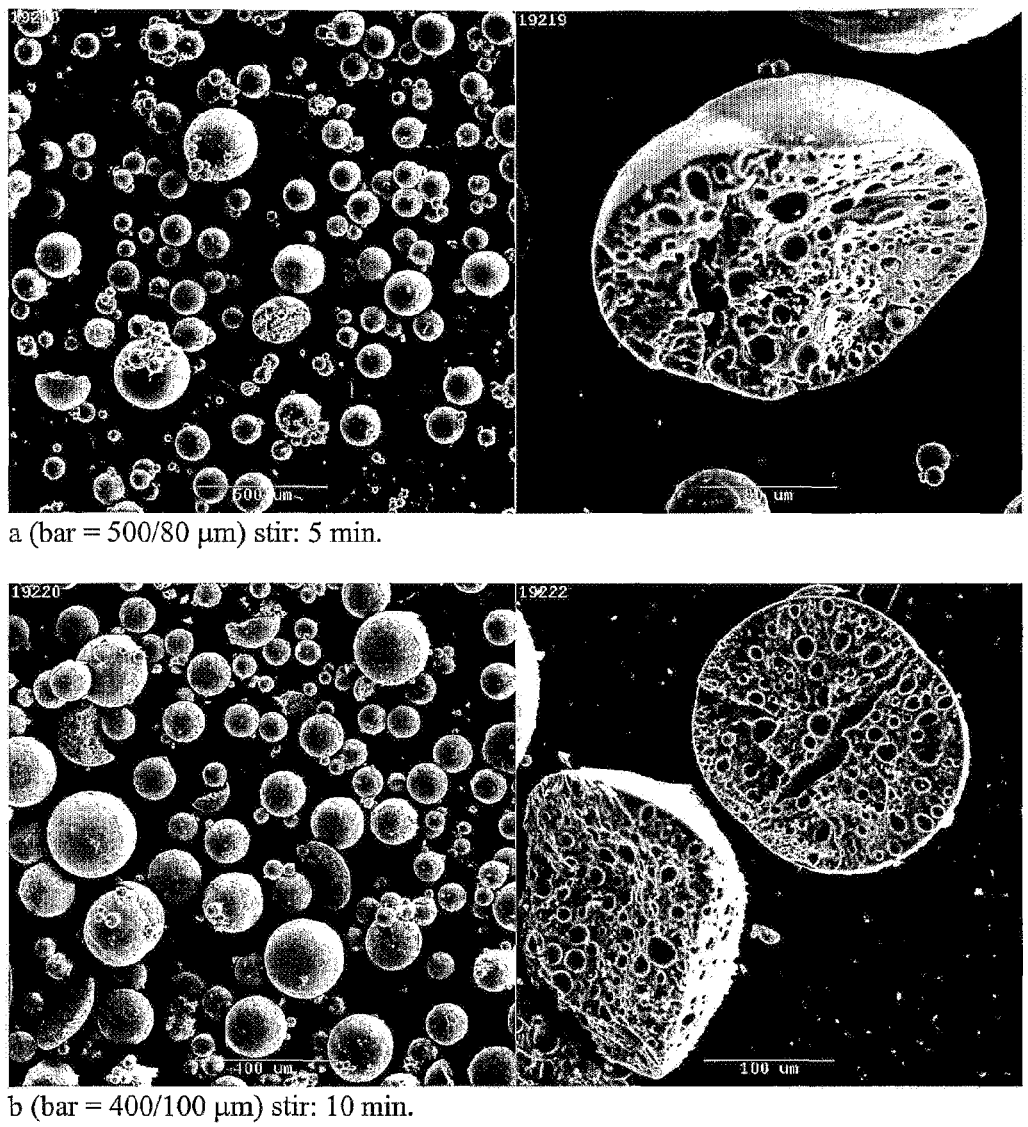
FIG. 42 shows SEM images of silica microparticles at different ageing times: (a) 5 minutes, (b) 10 minutes; (c) 20 minutes; (d) 40 minutes.
Figure 42:
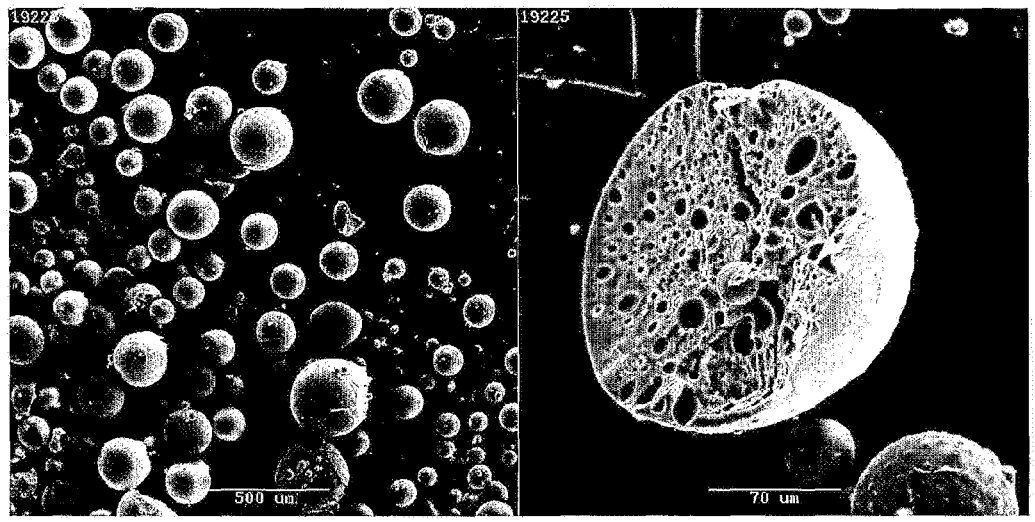
Figure 42:
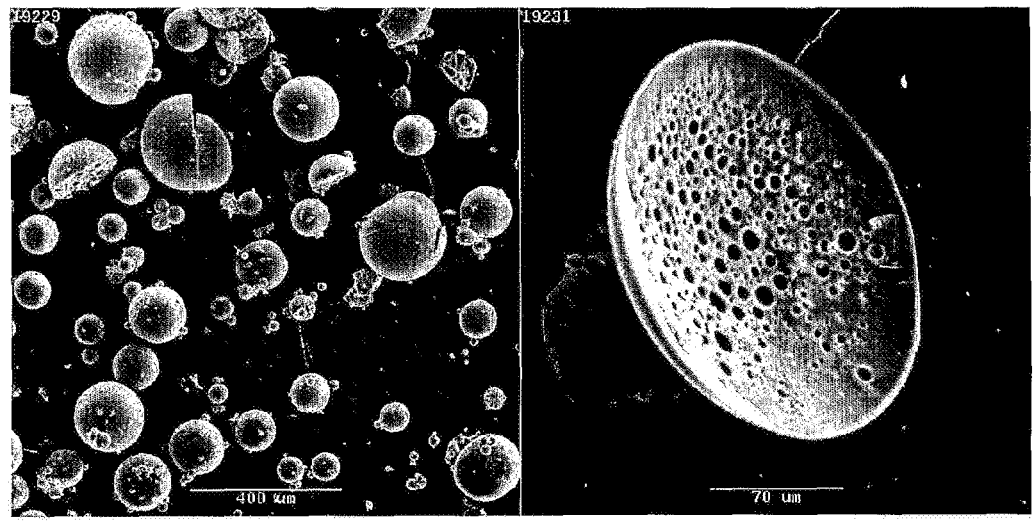
Figure 43:
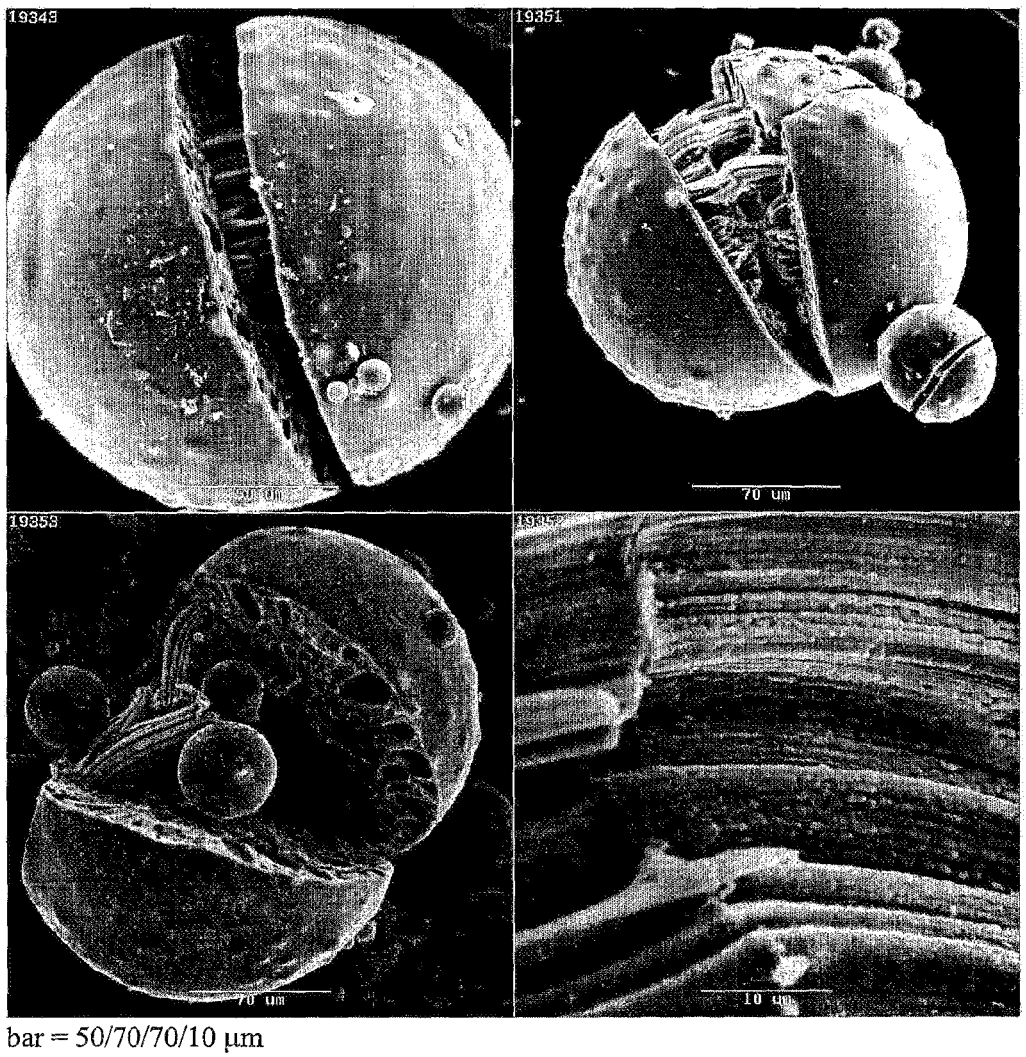
FIG. 43 shows SEM micrographs displaying the fracture of soft particles.

Table 10 and FIG. 42 show the effect of ageing time on the encapsulation efficiency of the dye and particle morphology under the typical synthesis conditions (using 0.600 g Tween 61). After the Oil$_1$/W phase (i.e. the first emulsion) was poured into the outer oil phase (the hydrophobic medium), the hydrolysed silica precursor condensed very rapidly to form microparticles. The results show that the highest encapsulation efficiency was obtained for a stirring time of 10 minutes. It is expected that the longer the stirring time, the more opportunity the internal oil (the hydrophobic phase) has to leach into the outer oil phase, thus reducing the encapsulation efficiency. However, too short a stirring time is not beneficial as it does not allow sufficient time for particles to attain sufficient strength to withstand filtration. Some SEM micrographs display the breakage of soft particles (FIG. 43). The particle size remained unchanged for different ageing times, but more broken particles were observed for longer stirring times.

4. Influence of the Methanol Evaporation and Addition

Figure 44:
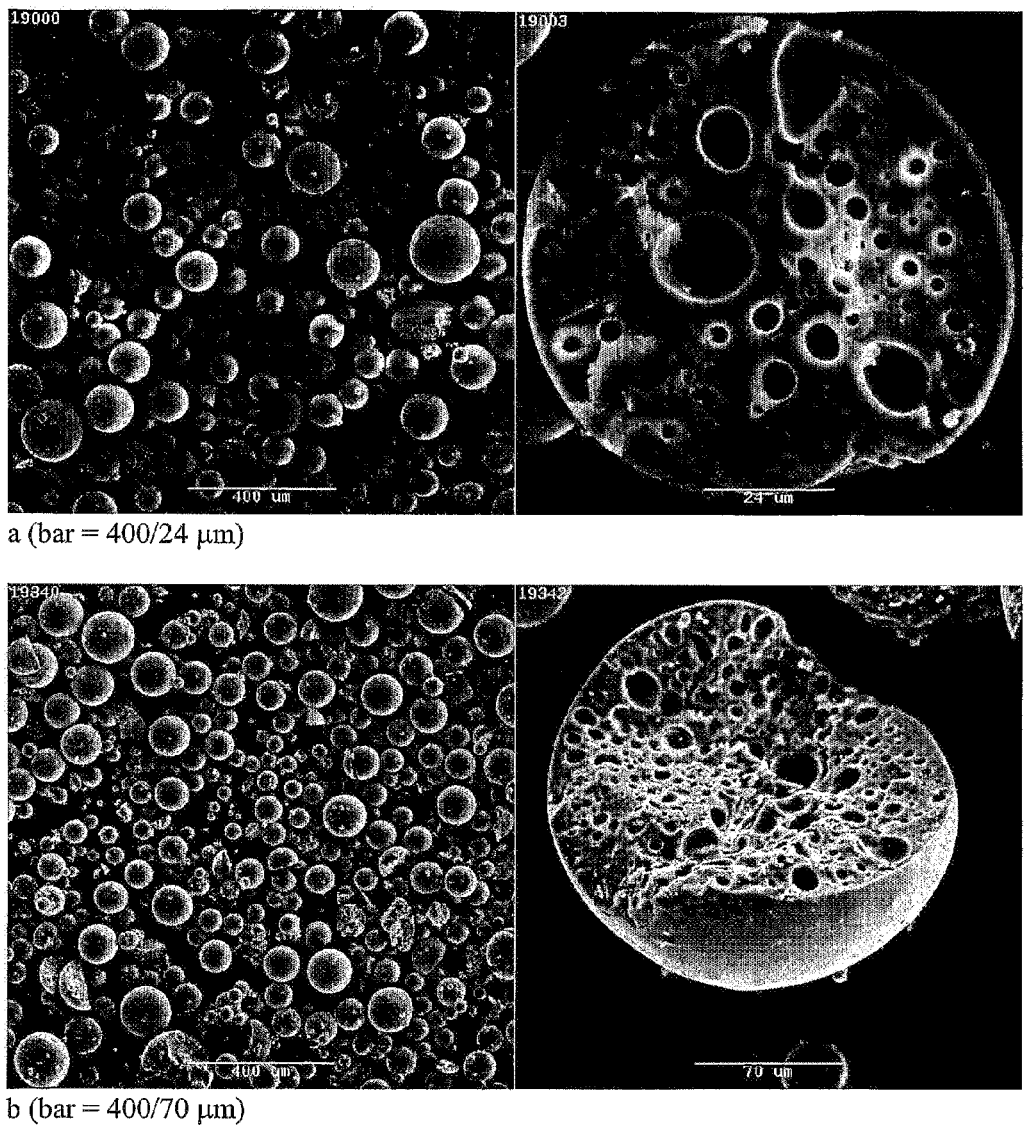
FIG. 44 shows SEM images of silica microparticles at different methanol evaporation times: (a) 1.5 hr, (b) 1 hr; (c) 0.5 hr; (d) no evaporation.
Figure 44:
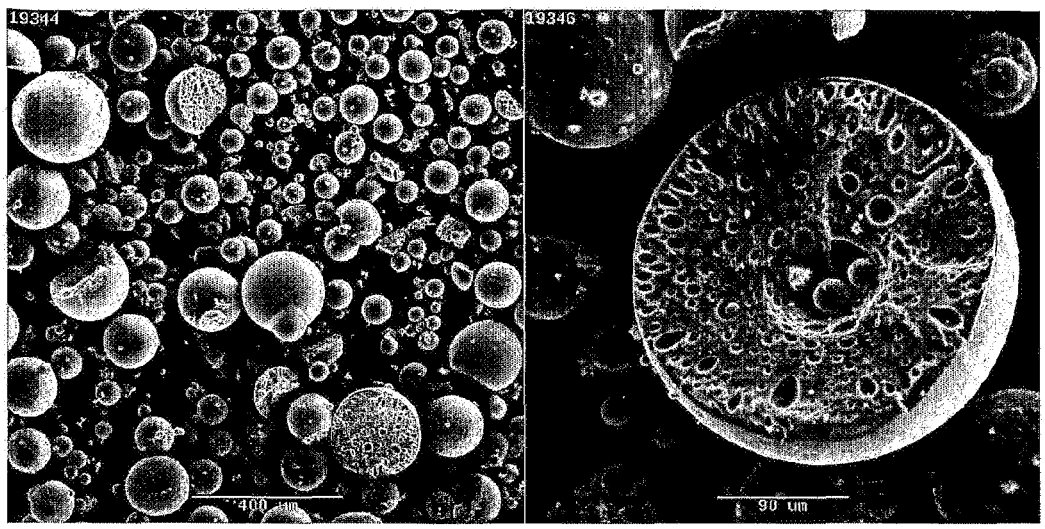
Figure 44:
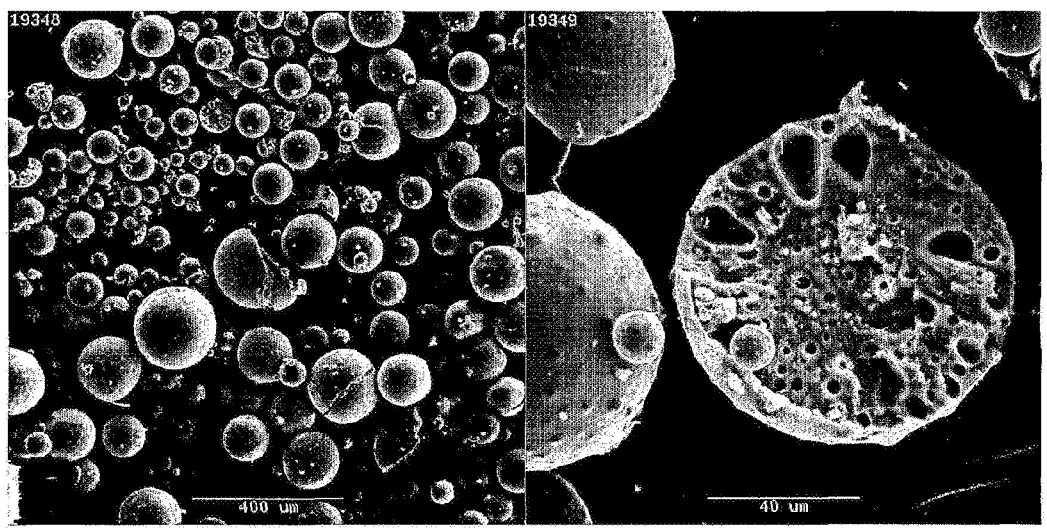

The methanol generated by hydrolysis of TMOS can potentially destroy the double emulsion structure. However, the present synthesis requires a double emulsion which is only partially stable, and thus a small amount of methanol can be tolerated by the system without significantly influencing the particle morphology and encapsulation efficiency. During the typical synthesis, the methanol generated during the hydrolysis and condensation reactions is evaporated prior to the mixing of the sol-gel solution with the internal oil emulsion. Table 11 and FIG. 44 show the influence of the evaporation time of alcohol evaporation (the standard time is 1.5 hour) on particle morphology and encapsulation efficiency under typical synthesis conditions with 0.600 g Tween 61.

It appears from these results that the encapsulation efficiencies remain constant despite variation in evaporation time, suggesting that the evaporation process may not be necessary. In order to understand if a short-chain alcohol has an influence on the particle morphology and how much alcohol can/be tolerated by the system, 4 or 10 mL methanol was added into the sol-gel solution under the typical synthesis conditions. The encapsulation efficiency was 22.6% and 1.6% for 4 mL, and 10 mL methanol, respectively, while the particle size was 85±51 µm for the former and 50±25 µm for the latter. The corresponding SEM images are displayed in FIG. 45.

Figure 45:
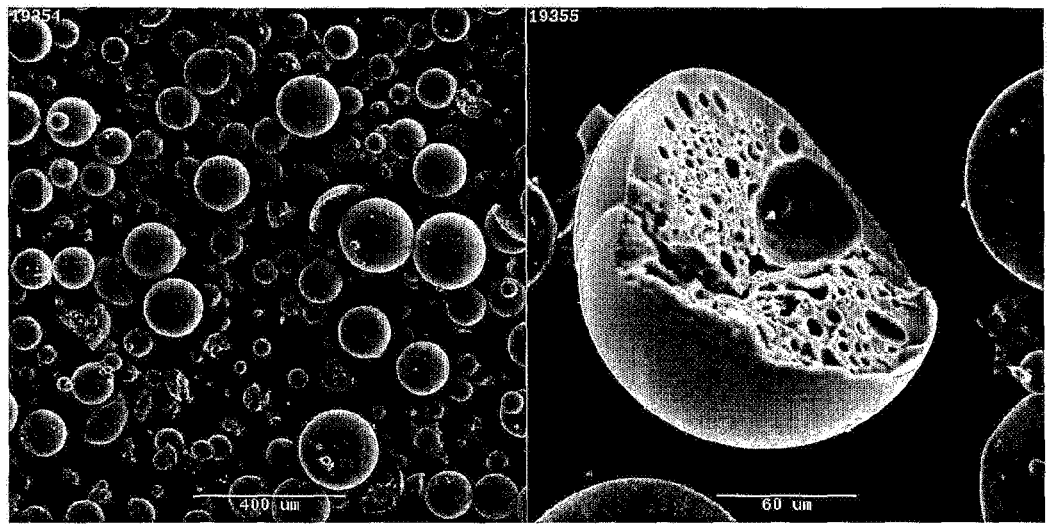
FIG. 45 shows SEM images of silica microparticles produced with the introduction of methanol: (a) 4 mL; (b) 10 mL.
Figure 45:
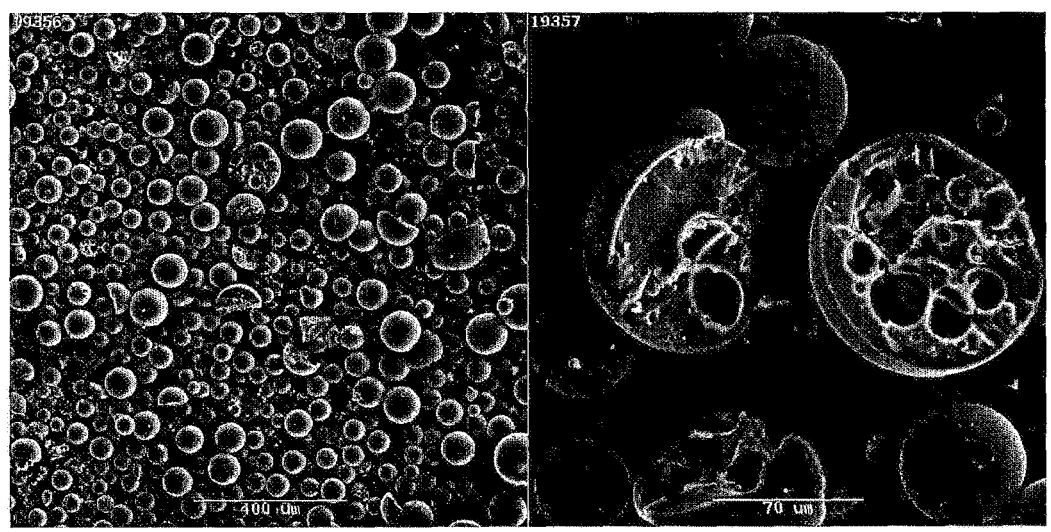

The addition of methanol significantly decreases the encapsulation efficiency. The more methanol introduced, the less dye remained inside the silica particles. The particle size also decreased with addition of methanol, but the size of the cavities increased, and the number of cavities within the silica matrix was reduced (FIG. 45).

5. Influence of the Polymer in Outer Oil Phase

Previous studies investigated the effect of addition of PEG in the water phase and HPC in the outer oil phase on particle morphology. Here the introduction of polymer in the outer oil phase only was investigated. HPC (Hydroxypropyl Cellulose, MW: 370,000) and EC7 (Ethyl Cellulose, MW: 64,400) were used. Typical synthesis conditions were used, with the additional details given in Tables 12 and 13.

Figure 46:
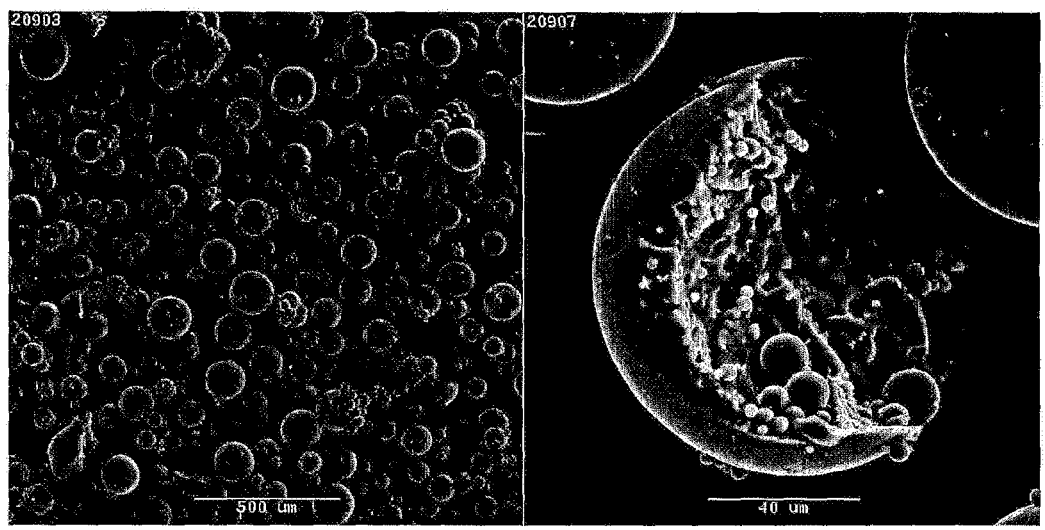
FIG. 46 shows SEM images of particles with HPC additions, made using Span 80 (0.2 mol/L) and HPC: (a) 4 g; (b) 8 g; (c) 16 g.
Figure 46:
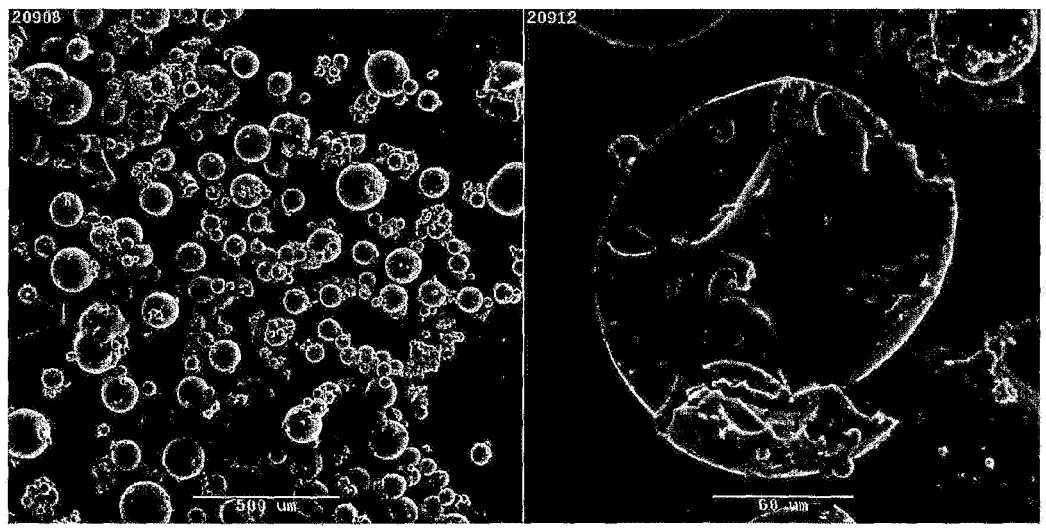
Figure 46:
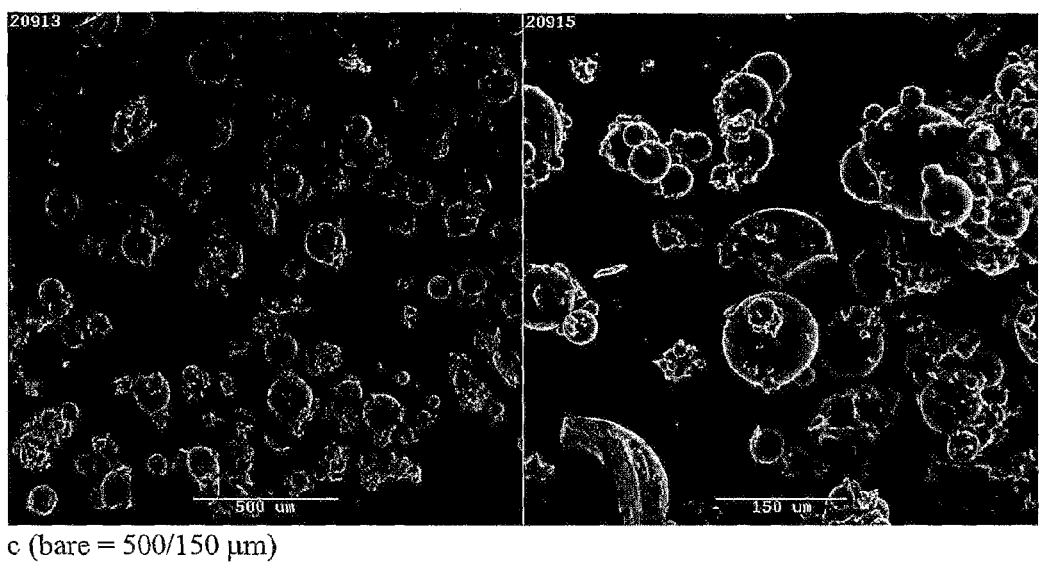

Addition of HPC appeared to have little effect on the size and morphology of the particles produced (FIG. 46), with a size range of 20-200 µm being obtained in all cases. In all cases, the particles appeared pale-blue at low Span 80 concentrations, but when the concentration of Span 80 was increased to 0.6 mol/L, the resulting particles had a dark blue colour. This is consistent with previous work which showed that the encapsulation efficiency increased with increasing Span 80 concentration. These results suggest that HPC addition has little effect on particle morphology and does not improve the encapsulation efficiency.

Figure 47:
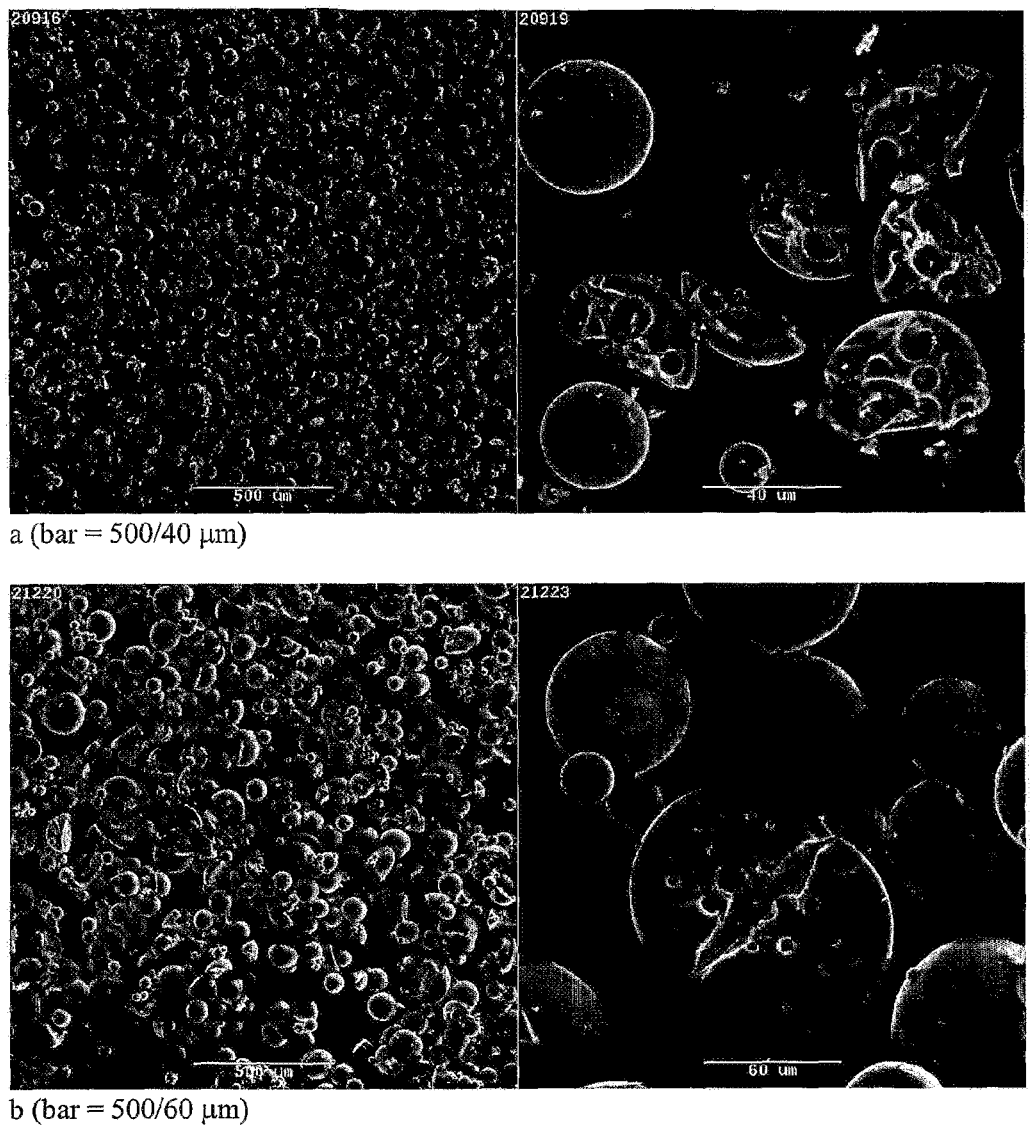
FIG. 47 shows SEM images of particles with EC7 additions: (a) Span 80: 0.4 mol/L, EC7: 5 g; (b) Span 80: 0.2 mol/L, EC7: 2.4 g; (c) Span 80: 0.3 mol/L, EC7: 2.4 g; (d) Span 80: 0.4 mol/L, EC7: 2.4 g.
Figure 47:
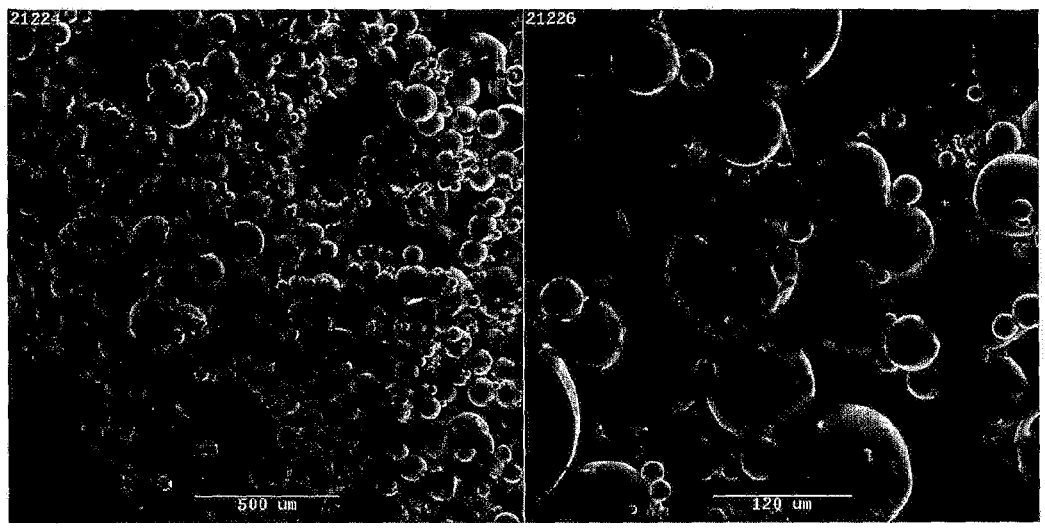
Figure 47:
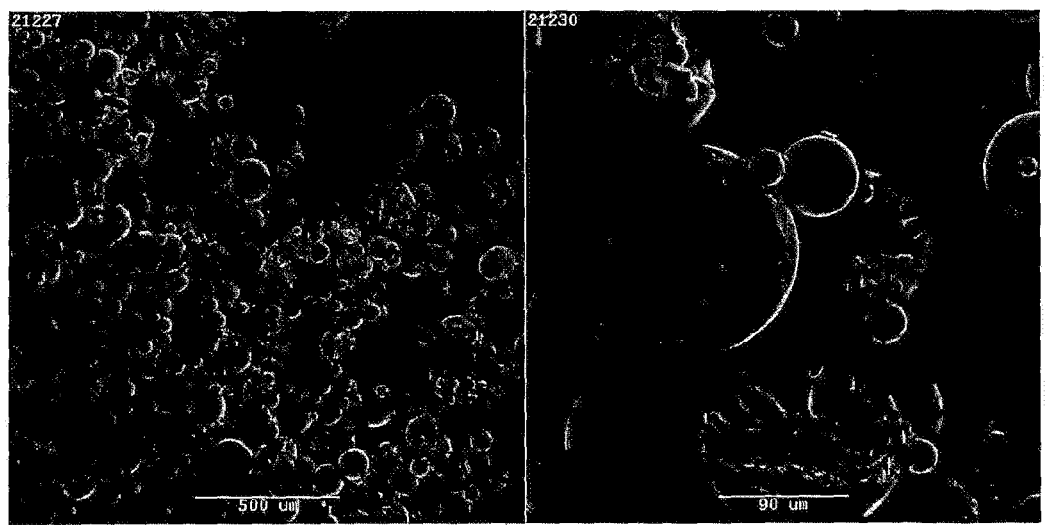

Likewise, the encapsulation efficiency did not improve with addition of EC7, and only increased with increasing Span 80 concentration as had already been established in a previous study. The large amount of EC7 did, however, have an effect on particle diameter, producing noticeably smaller microparticles (FIG. 47), which is possibly due to increasing viscosity of the outer oil phase.

6. Influence of Washing on the Surfactant Residue

Figure 48:
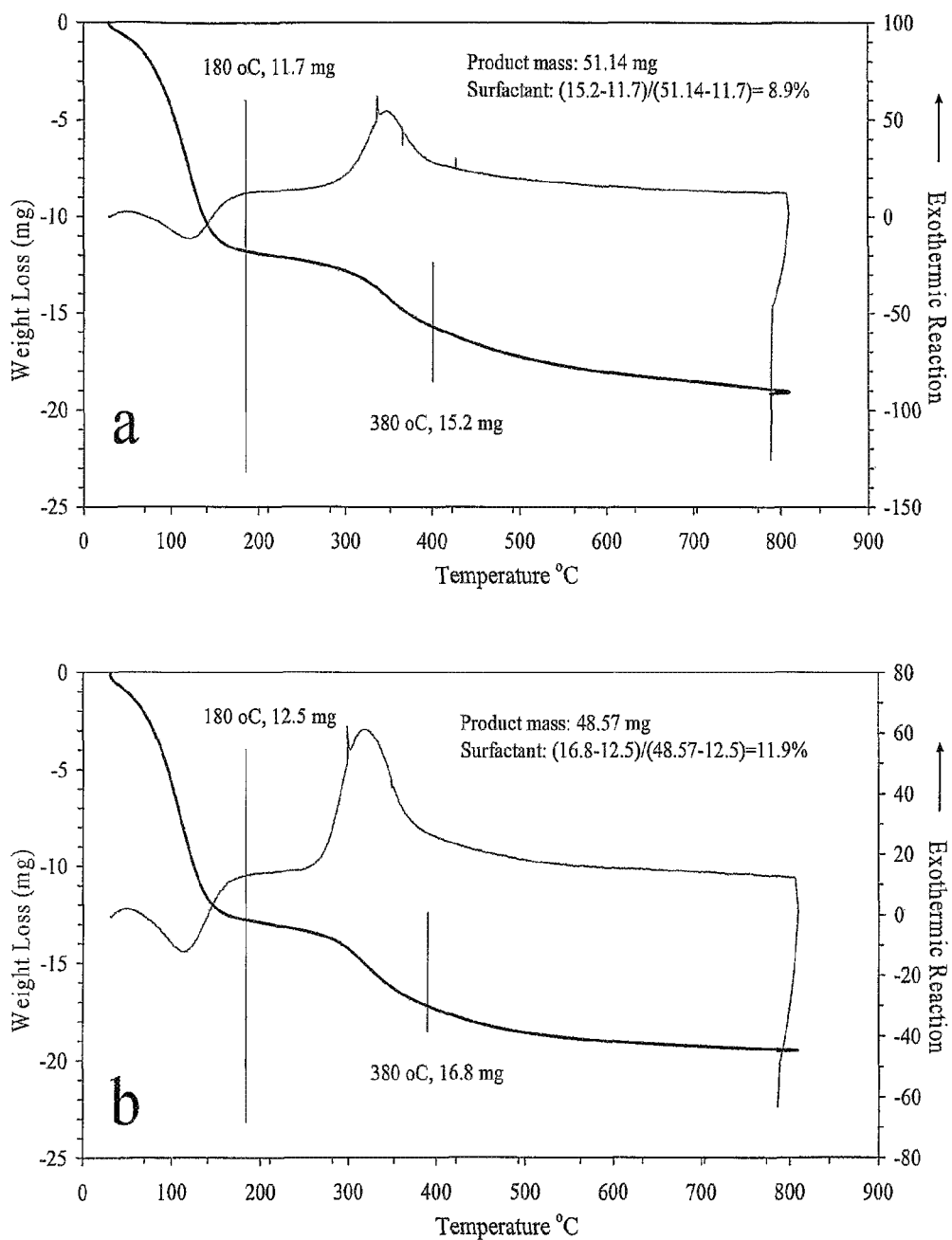
FIG. 48 shows TGA/DTA traces for various washing methods: (a) 3×15 mL 1 mol/L NaCl plus 3×15 mL water wash; (b) 6×15 mL water wash; (c) Tween 20 0.05% 6×15 mL wash; (d) Tween 80 0.05% 6×15 mL wash.
Figure 48:
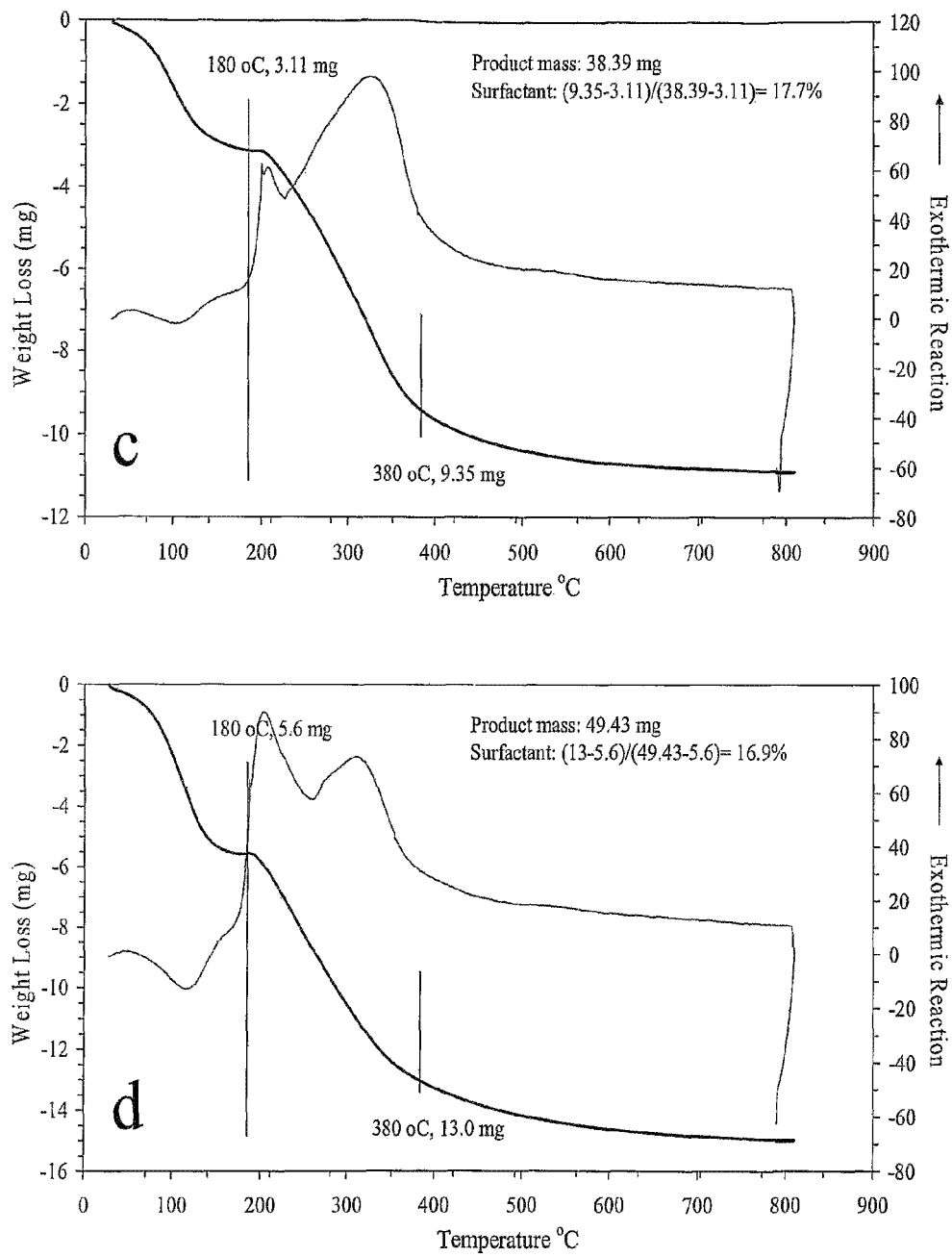

Several methods were tested to reduce the surfactant residue on the particle surface, and the TGA/DTA results are displayed in Table 14 and FIG. 48. The external (second) surfactant, Span 80, is hydrophobic (HLB 4.3) and is soluble only in hydrophobic solvents. Apolar solvents can not be used to wash the particles, as they will dissolve the doped active material which is also hydrophobic. The best washing method identified to date is to first wash with salt solution and then use pure water to wash further. Hydrophilic surfactants such as Tween 20 (HLB 16.7) and Tween 80 (HLB 15) did not remove Span 80, but left residue on the particles, as confirmed by two exothermic combustion humps in the DTA (differential thermal analysis) trace.

7. Influence of the Synthesis pH on Release Rate

Figure 49:
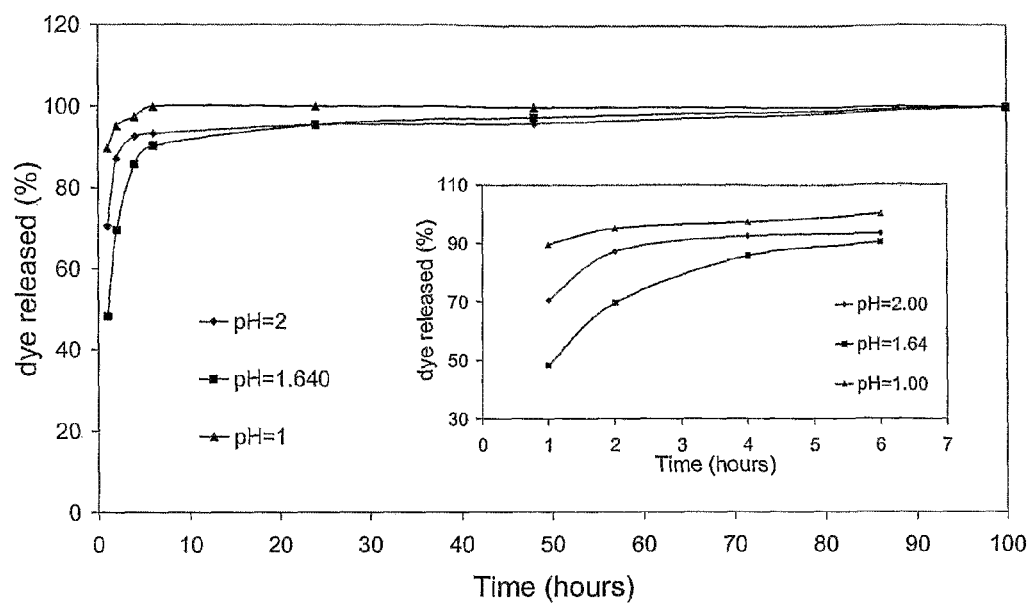
FIG. 49 shows a graph of dye release vs time, illustrating the influence of synthesis pH on release rate using ethanol as the release medium.

Silica particles were synthesised according to the typical synthesis conditions but using Tween 61 as the internal surfactant. It can be seen from FIG. 49 that almost 100% of the dye has been released after 48 hours. Approximately 50% of dye was released in the first hour from particles made at pH=1.64 while more than 70% was released from the particles made at pH=2 (FIG. 49 inset). For particles made at pH=1, 90% of dye was released after 1 hour of releasing. After 6 hours of stirring, most of the dye was released for all types of particles. After that time, the remaining dye was released slowly up until 48 hours.

The synthesis pH appears to have a significant influence on the morphology of the silica matrix, which is a factor in controlling the release rate. The difference in release rate between pH=2 and pH=1.64 may be explained by the different porous structure as revealed by nitrogen adsorption. As discussed previously, the pore volume and the surface area of the silica matrix decreases and particles became denser with decreasing pH. Thus slower release might be expected. In addition, since the particle size increases with decreasing pH, the oil has a longer diffusion path, further decreasing the release.

8. Influence of the Amount of Internal Surfactant on Release Rate

Figure 50:
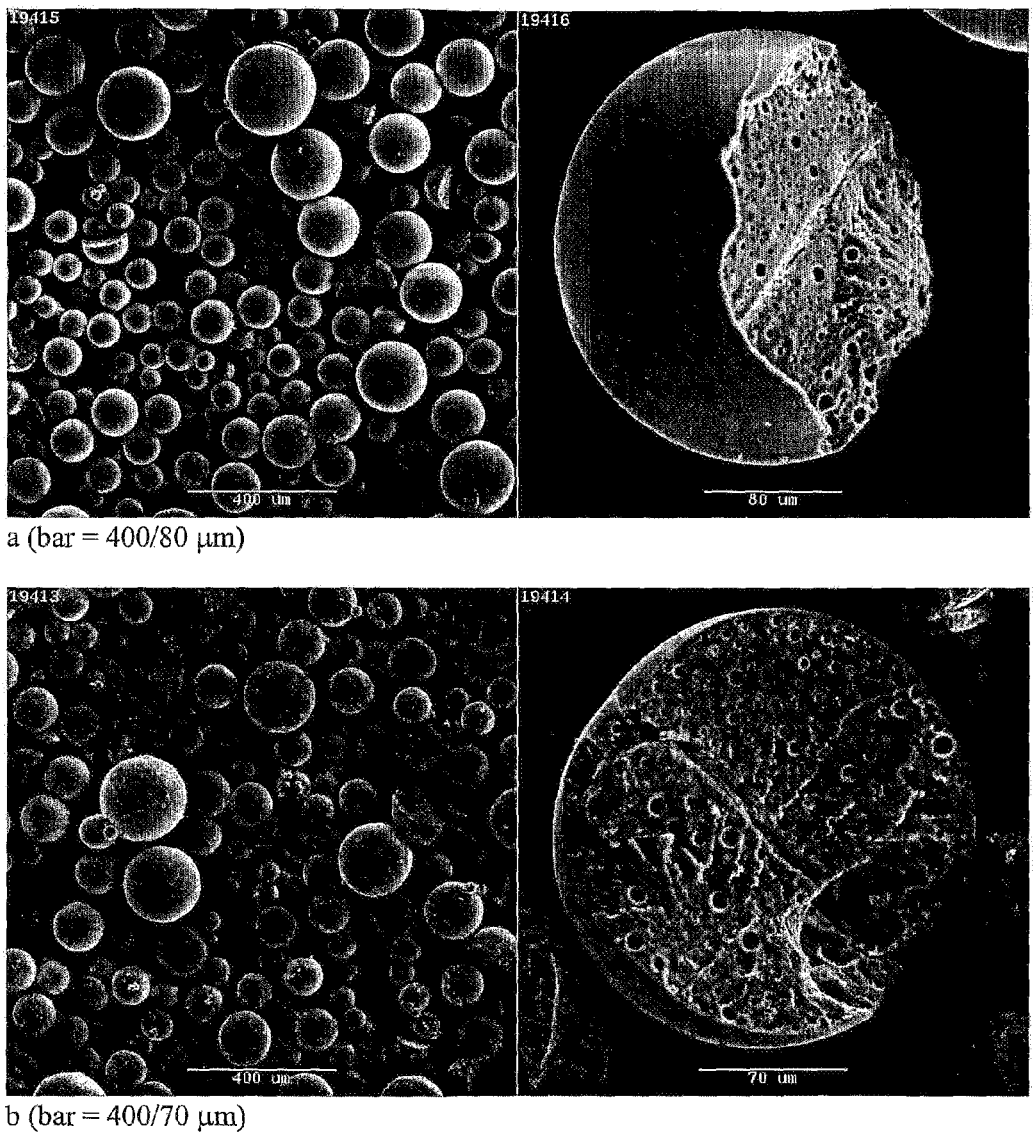
FIG. 50 shows SEM images of particles synthesised at pH1 with Tween 61 (a) 150 mg and (b) 300 mg as internal surfactant under typical synthesis conditions.
Figure 51:
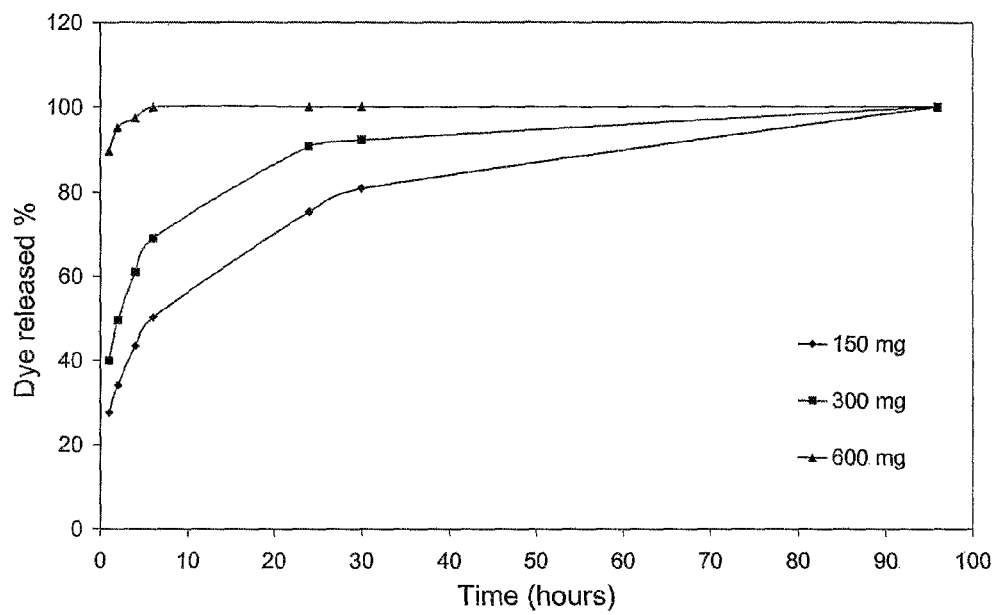
FIG. 51 shows a Solvent blue release curve for silica particles synthesised at pH1 using different amounts of Tween 61 as internal surfactant, in which the dye is released into ethanol.

Particles were synthesised using Tween 61 as the internal surfactant at pH=1. The encapsulation efficiencies of SB-35 (19.6 wt. %) were approximately 50% of that for particles made at pH=2, and were independent of the mass of Tween 61, as in the case of particles made at pH=2. The particle size of particles made at pH 1 was about 106±58 μm and remained unchanged at various Tween 61 amounts (150-600 mg). FIG. 50 shows the SEM images of the particles, and the corresponding release curves are displayed in FIG. 51. The dye was gradually released for loadings of 150 and 300 mg Tween 61 while the fastest release rate was found for a loading of 600 mg Tween 61.

Figure 52:
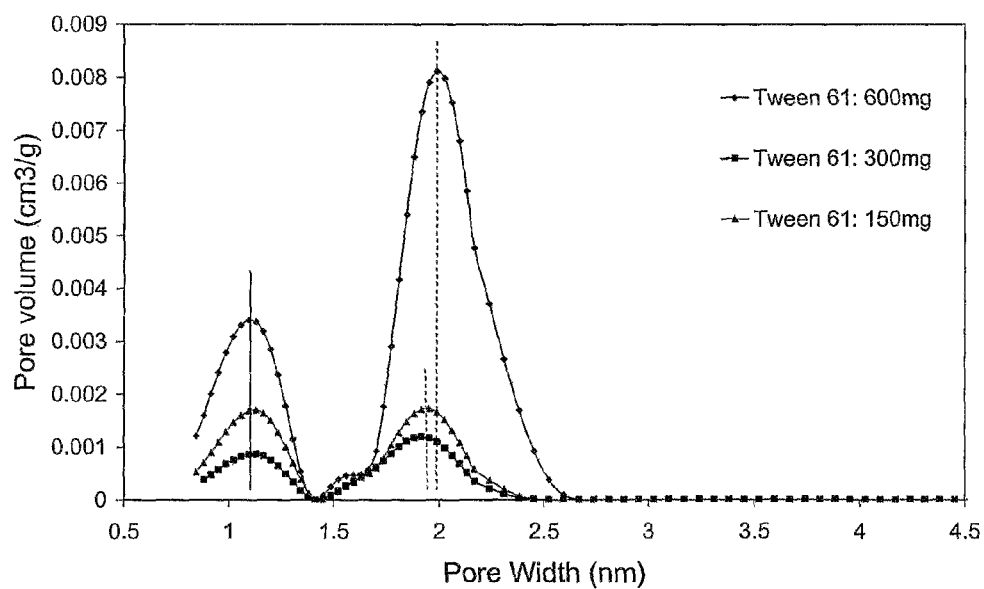
FIG. 52 shows pore size distributions of silica particles synthesised at pH1 using different amount of internal surfactant by DFT model.

Table 15 shows the BET and DFT results of synthesis using internal surfactant at various amounts at pH=1, and FIG. 52 displays the pore size distribution of the corresponding samples. All samples had approximately the same peak pore size as measured by DFT and BET. Similar encapsulation efficiencies of hydrophobic dye (solvent blue) were obtained under these conditions (about 19.6%), suggesting the encapsulation of hydrophobes shows little dependence on the meso/microporosity of the silica matrix. As mentioned previously, the encapsulation efficiency appears to be linked to the macroporosity, which is not measurable by nitrogen adsorption. Nevertheless, the pore size distribution appears to a key role in controlling the release of the oil from the vacuoles through the silica matrix. The larger the pore size the faster the release. Alternatively, faster release for higher quantities of internal surfactant used may be due to a higher quantity of surfactant remaining encapsulated inside the pores which can facilitate the solubilisation of the entrapped hydrophobe upon release.

9. Encapsulation of Other Hydrophobic Materials 9.1. Encapsulation of Diuron

Diuron (3-(3,4-Dichlorophenyl)-1,1-dimethylurea) [Sigma, min. 98%], structure shown below, can be encapsulated using the current process. —.

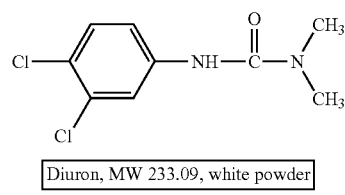

Diuron, MW 233.09, white powder

Figure 53:
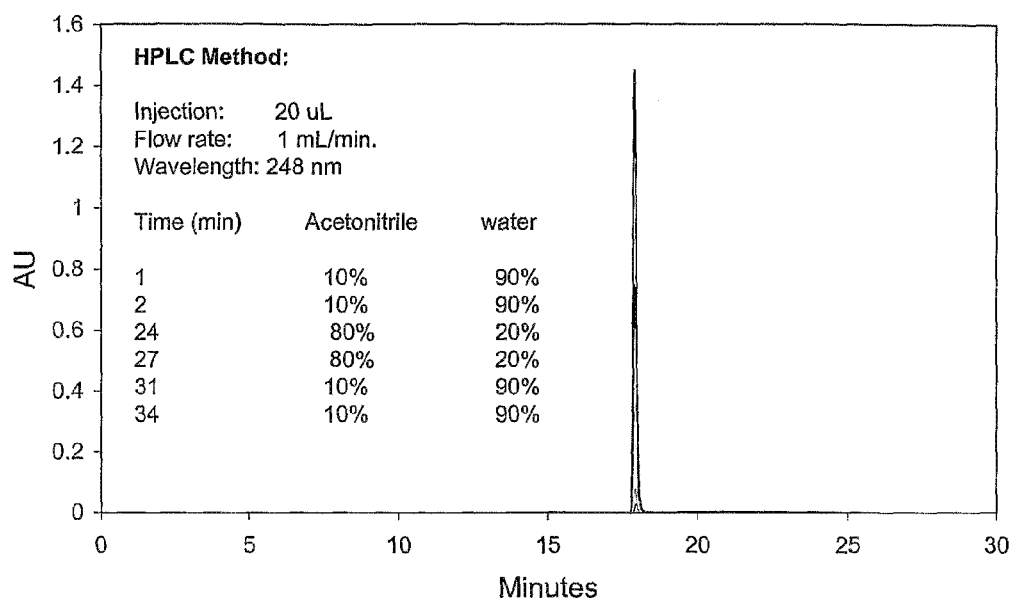
FIG. 53 shows HPLC traces for diuron measurement using diuron concentration in methanol from 2-100 μg/mL.

The method of reverse phase HPLC (Waters) to quantify diuron is shown in FIG. 53, and the standard calibration equation is: $Area_{peak}=11034 C_{diuron}+37673$ ($R^2=0.9996$) for a diuron concentration between 2 μg/mL and 100 μg/mL.

The particle synthesis was the same as the typical synthesis conditions described earlier, however the amounts of all components were halved. Diuron was introduced in the internal oil (the hydrophobic phase): 2 mL (90 mg/mL diuron in THF, here THF is as the internal oil phase). The internal oil phase is THF with the diuron concentration 90 mg/mL (here THF is the internal oil phase).

Figure 54:
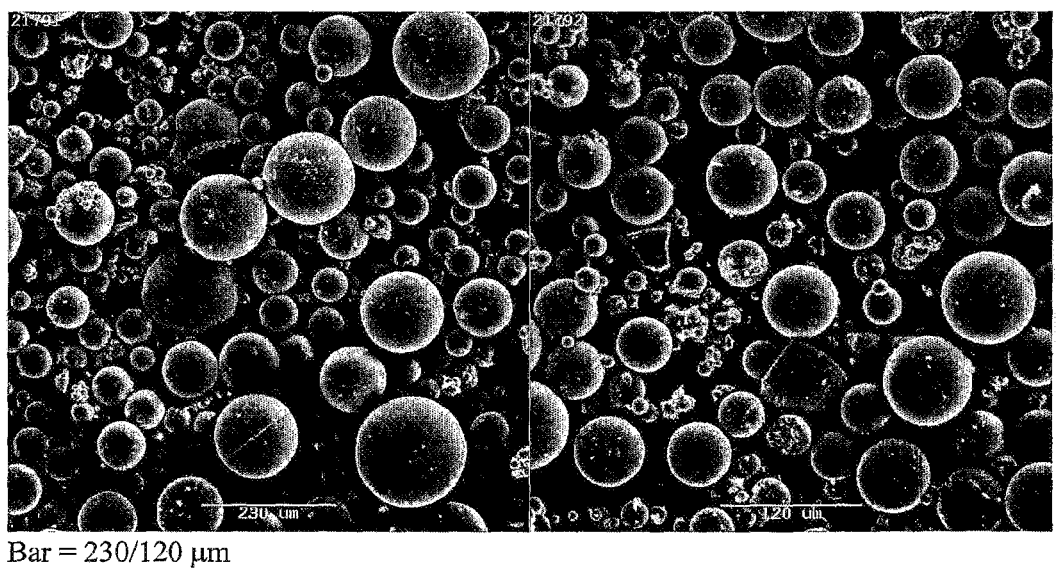
FIG. 54 shows SEM images of silica particles with encapsulated diuron.

After synthesis, approximately 50 mg product (i.e. particles) was added to 50 mL methanol, and the suspension was stirred for three days. Particles were separated by centrifugation, and the supernatant was extracted and filtered through a 0.22 micron cellulose filter before HPLC analysis. The organic phase from the reaction was diluted with dry acetone and filtered to determine the amount of diuron lost during synthesis. The corresponding SEM images are shown in FIG. 54.

The low value of the encapsulation efficiency, based on the release results, may be due to a fraction of diuron being released into methanol (the solubility of diuron in methanol is 43 mg/mL). The high encapsulation efficiency based on the amount lost during synthesis may be somewhat overestimated because it does not take into account diuron which passes into the aqueous phase during washing. This is expected to be low, however, because the water solubility of diuron is low (42 mg/L at 25° C.).

9.2 Encapsulation of Basil Flavour Oil

Basil flavour oil was supplied by Quest International Ltd. The main components are: 44.45% MCT oil (medium chain triglyceride), 10.00% Basil oil (unknown composition but contains a number of vegetable oils), 3.00% linalyl acetate, and 27.50% linalool. It also contains, amongst other components, eugenol and eucalyptol. The density of the basil flavour oil is 0.9519 g/mL at 20° C. Linalool (molecular structure shown below) was selected as a marker for encapsulation of basil flavour oil.

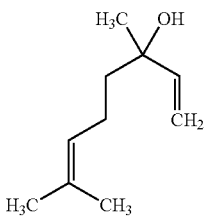

Linalool, MW 154.25, colourless liquid

Standard solutions were prepared by dissolving (±)-Linalool (Fluka purum, ≥95.0% GC) in methanol in the range of 5-100 μg/mL (stock solution: 2.000 mg/mL). Linalool was quantified by reverse phase HPLC (Waters) using an Atlantis $dC_{18}$ 5 μm, 4.6×150 mm column with flow rate of 1 mL/min and UV/Vis detector at a wavelength of 208 nm. Injection volume was 20 μL and the mobile phase was varied as follows:

| Time (min.) | H$_2$O % | MeOH % |
|---|---|---|
| 1 | 50 | 50 |
| 2 | 50 | 50 |
| 20 | 5 | 95 |
| 22 | 5 | 95 |
| 25 | 50 | 50 |
| 30 | 50 | 50 |

The standard calibration equation is: $Area_{peak}=2.54\times10^4 C_{linalool}+2.98\times10^5$ ($R^2=0.99925$). The linalool concentration in the basil flavour oil was determined to be 31.52 wt. %.

The particle synthesis was carried out according to the typical synthesis conditions, however the amount of all components was halved. After synthesis, about 1 g product was mixed with 20.00 mL methanol, and the suspension was stirred vigorously for two weeks. Particles were separated by centrifugation and the supernatant was extracted and filtered though a 0.22 micron cellulose filter before HPLC analysis. The organic phase from the synthesis was diluted in dry acetone and filtered to determine the amount of linalool lost during the encapsulation process. The experimental results are shown in Table 17. It was assumed that the encapsulation efficiency of the linalool was identical to that of the basil oil.

Figure 55:
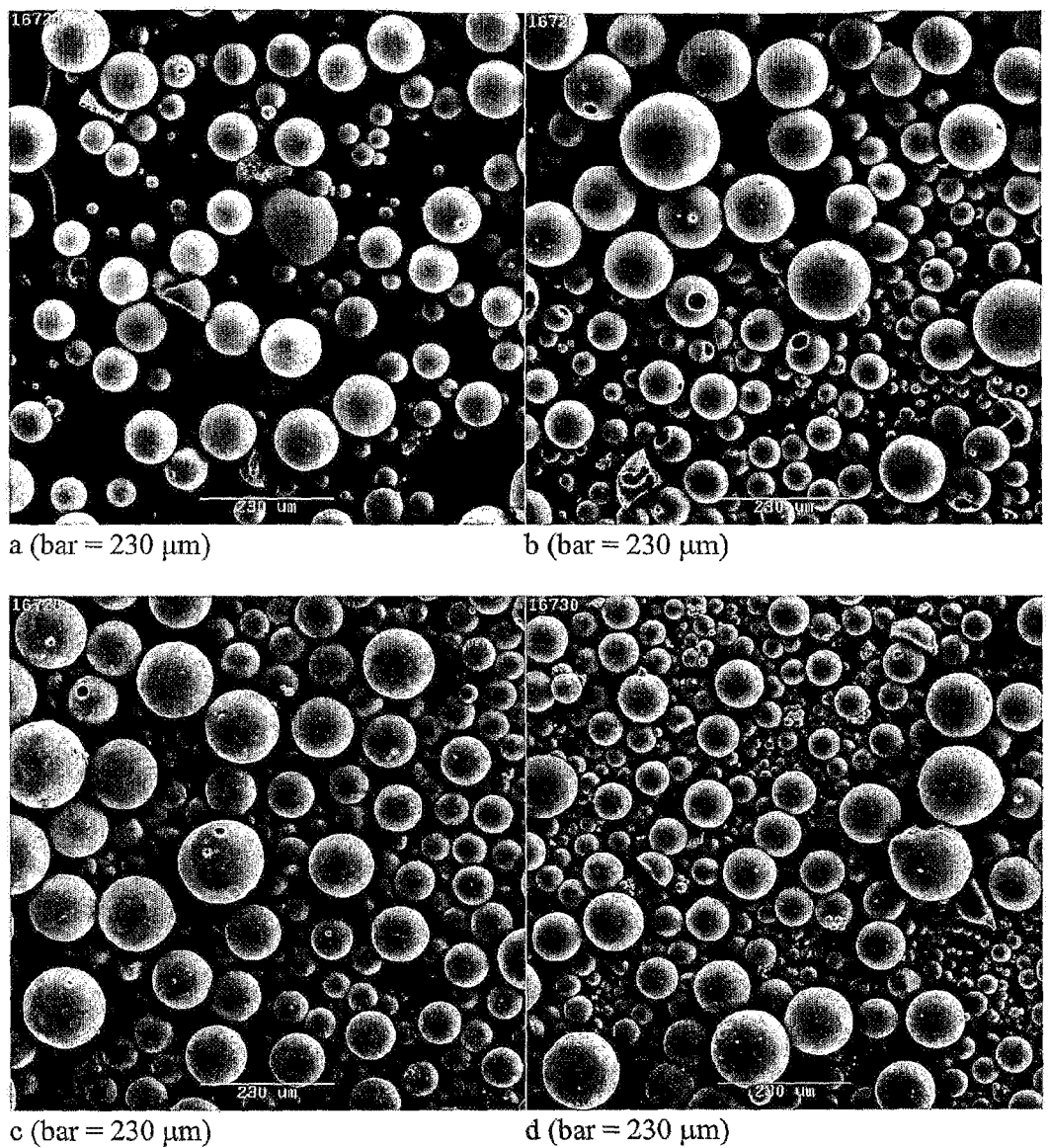
FIG. 55 shows SEM images of silica particles with encapsulated basil oil, made using: (a) Tween 21: 0.3 g, basil oil 0.35 mL; (b) Tween 21: 0.3 g, basil oil 0.70 mL; (c) Tween 21: 0.6 g, basil oil 0.35 mL; (d) Tween 21: 0.6 g, basil oil 0.70 mL.

The encapsulation efficiency based on the amount of linalool released from the particles was about 2-3% for particles made using 0.3 g Tween 21 as internal surfactant. After doubling the amount of the internal surfactant, less linalool was encapsulated. If the encapsulation efficiency is calculated by using the amount of linalool lost in the organic phase, the encapsulation efficiencies are around 15%, except one value of 40%. The difference between these two methods for determining encapsulation efficiency is possibly due to linalool evaporation during drying of the particles, and/or to incomplete collection of the silica particles. FIG. 55 displays the particle morphologies made using different synthesis parameters. Similar particle sizes and size distributions were obtained at various conditions.

CONCLUSIONS

Sol-gel processing by utilising an O/W/O double emulsion was successfully used to encapsulate hydrophobic species in silica microspheres. Different processing parameters such as the internal surfactant, quantity of internal oil, the mixing time etc, have been varied in order to study their influence on the encapsulation efficiency and particle morphology. It was possible to vary the quantity of hydrophobic materials encapsulated inside silica microspheres, as well as to modify their size distribution by varying the sol-gel reaction processing parameters.

The encapsulation efficiency may be controlled by varying the nature of the internal surfactant, the quantity of internal oil introduced in the system, the mixing time and excess methanol in the sol-gel solution. The SEM analysis agreed with the trends in encapsulation efficiency. It revealed that the number of observed macropores (i.e. vacuoles where the oil droplets are lodged) increases with the encapsulation efficiency. No macropores were observed when the encapsulation efficiency was low.

The particle size may be controlled by varying the concentration of the internal and external surfactants and the pH. When the concentration of the internal surfactant increases, the particle size decreases. This suggests that the excess of the internal surfactant interacts with the second surfactant and thus influences the particle size. In addition, the particle size increases significantly when the pH decreases.

Release of encapsulated oil can be controlled by controlling the porosity of the silica matrix. This may be controlled by adjusting the pH of the hydrophilic phase. At pH <2, the quantity of pores and the size of the pores decreases, thus slowing the release of the oil.

The above results indicate that the process of the present invention enables encapsulation of hydrophobic species in silica microspheres and control of their release. This promising technology has potential applications in release of products in beauty creams, perfumes, drugs, food, and cleaning agents, etc.

TABLE 1

The properties of surfactants and polymers used

| Surfactant | Trade name | Molecular weight | Molecular formula | HLB value | Ethylene oxide unit |
|---|---|---|---|---|---|
| Polyoxyethylene (4) sorbitan monolaurate | Tween 21 | 522 | $C_{18}H_{34}O_6(C_2H_4O)_4$ | 13.3 | 4 |
| Polyoxyethylene (20) sorbitan monolaurate | Tween 20 | 1226 | $C_{18}H_{34}O_6(C_2H_4O)_{20}$ | 16.7 | 20 |
| Polyoxyethylene (20) sorbitan monooleate | Tween 80 | 1310 | $C_{24}H_{44}O_6(C_2H_4O)_{20}$ | 15.0 | 20 |
| Sorbitan monooleate | Span 80 | 428.62 | $C_{24}H_{44}O_6$ | 4.3 | — |
| sorbitan monolaurate | Span 20 | 346.47 | $C_{18}H_{34}O_6$ | 8.6 | — |
| Polyethylene glycol | PEG | average 20,000 | * | — | — |
| Hydroxypropyl cellulose | HPC | average 37,000 | ** | — | — |

*:

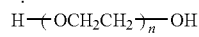
$H-(OCH_2CH_2)_n-OH$

**:

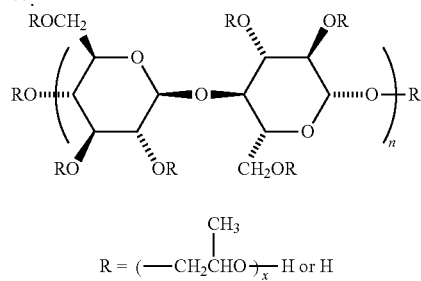

$R = (-CH_2\overset{CH_3}{\underset{|}{C}HO})_x H$ or $H$

TABLE 2

SB-35 encapsulation efficiency in silica spheres made with mixed precursors

| | Sample | | |
|---|---|---|---|
| | A | B | C |
| Precursor | 25 mol. % MTMS | 25 mol. % PTMS | 25 mol. % VTMS |
| | 75 mol. % TMOS | 75 mol. % TMOS | 75 mol. % TMOS |
| Dye encapsulation efficiency (direct method) | 38.5 wt. % | 4.8 wt. % | 15.6 wt. % |
| Dye encapsulation efficiency | (a): 22.5 wt. % | | N/A |

TABLE 2-continued

SB-35 encapsulation efficiency in silica spheres made with mixed precursors

| | Sample | | |
|---|---|---|---|
| | A | B | C |
| (indirect method) | (b): 20.4 wt. % | | |
| Release in cyclohexane | | | |
| Release in dodecane | | | |

TABLE 3

Synthesis parameters for SB-35/limonene doped silica spheres

| Sample | Limonene (mL) | SB-35 (mg) | pH 2 $H_2O_{(1)}$ (g) | PEG (g) | Tween 21 (g) | pH 2 $H_2O_{(2)}$ (g) | TMOS (mmol) | $Oil_2$ (75 mL) | Span 80 (mmol) | HPC (g) |
|---|---|---|---|---|---|---|---|---|---|---|
| a | 0.36 | 0.72 | 1.068 | — | 0.30 | 1.068 | 29.65 | kerosene | 37.53 | — |
| b | 0.54 | 1.08 | 1.605 | — | 0.45 | 1.605 | 44.48 | kerosene | 37.53 | — |
| c | 0.36 | 0.72 | 1.070 | 0.321 | 0.30 | 1.068 | 29.65 | kerosene | 37.53 | 0.074 |
| d | 0.54 | 1.08 | 1.605 | 0.482 | 0.45 | 1.605 | 44.48 | kerosene | 37.53 | 0.148 |
| e | 0.36 | 0.72 | 1.068 | — | 0.30 | 1.068 | 29.65 | cyclohexane | 37.53 | — |
| f | 0.54 | 1.08 | 1.605 | — | 0.45 | 1.605 | 44.48 | cyclohexane | 37.53 | — |
| g | 0.36 | 0.72 | 1.070 | 0.321 | 0.30 | 1.068 | 29.65 | cyclohexane | 37.53 | 0.074 |
| h | 0.54 | 1.08 | 1.605 | 0.482 | 0.45 | 1.605 | 44.48 | cyclohexane | 37.53 | 0.148 |

TABLE 4

Synthesis parameters for SB-35/limonene doped silica spheres

| Sample | Limonene (mL) | SB-35 (mg) | pH 2 $H_2O_{(1)}$ (g) | PEG (g) | $Surf_1$ (g) | pH 2 $H_2O_{(2)}$ (g) | TMOS (mmol) | $Oil_2$ (150 mL) | Span 80 (mmol) | HPC (g) |
|---|---|---|---|---|---|---|---|---|---|---|
| a | 0.36 | 0.72 | 1.068 | 0.321 | Tween 21 0.3 | 1.068 | 29.65 | cyclohexane | 90 | 0.148 |
| b | 0.36 | 0.72 | 1.068 | 0.321 | Tween 21 0.3 | 1.068 | 29.65 | cyclohexane | 90 | 0.074 |
| c | 0.54 | 1.08 | 1.605 | 0.482 | Tween 21 0.6 | 1.605 | 44.48 | cyclohexane | 90 | 0.148 |
| d | 0.54 | 1.08 | 1.605 | 0.482 | Tween 21 0.6 | 1.605 | 44.48 | cyclohexane | 90 | 0.074 |
| e | 0.54 | 1.08 | 1.605 | 0.482 | Tween 20 0.6 | 1.605 | 44.48 | cyclohexane | 90 | 0.148 |
| f | 0.54 | 1.08 | 1.605 | 0.482 | Tween 20 0.6 | 1.605 | 44.48 | cyclohexane | 90 | 0.074 |
| g | 0.54 | 1.08 | 1.605 | 0.482 | Tween 80 0.6 | 1.605 | 44.48 | cyclohexane | 90 | 0.148 |
| h | 0.54 | 1.08 | 1.605 | 0.482 | Tween 80 0.6 | 1.605 | 44.48 | cyclohexane | 90 | 0.074 |

TABLE 5

Comparison between the earlier process of FIG. 27 and the present process.

| | Earlier Process | Present Process |
|---|---|---|
| System | Requires a table double emulsion | no need for stable emulsions |
| [water]/[precursor] | 4 | 2-8 |
| Catalyst | base | Acid |
| $O_1/W$ to $O_2$ volume ratio | ≤5% | Up to ~20% |
| Thickening agent | HPC | None Required |
| Particle size | Nano | Micron |
| Reproducibility | Low | High |
| Yield | Low | 99% |
| Encapsulation efficiency | (as reported in paper) | |

TABLE 6

Synthesis results (pH = 2) by various non-ionic surfactants and amounts.

| Surfactant | Weight added | E.E. of SB-35 | Particle shape and size* |
|---|---|---|---|
| NP-5 | 0.6 g | 0.5% | Spherical: 136 ± 81 μm |
| NP-5* | 1.2 g | 1.0% | Spherical: 88 ± 53 μm |
| NP-6 | 0.6 g | 1.8% | Spherical: 129 ± 80 μm |
| NP-6* | 1.2 g | 1.1% | Spherical: 40 ± 36 μm |
| NP-9 | 0.15 g | 12.6% | Spherical: 111 ± 74 μm |
| NP-9 | 0.3 g | 16.0% | Spherical: 110 ± 65 μm |
| NP-9 | 0.6 g | 21.7% | Spherical: 65 ± 40 μm |
| NP-9* | 1.2 g | 13.3% | Spherical: 63 ± 39 μm |
| Triton X-100 | 0.6 g | 13.1% | Spherical: 67 ± 59 μm |
| Triton X-100* | 1.2 g | 8.4% | Spherical: 16 ± 13 μm |
| Triton X-114 | 0.6 g | 8.2% | Spherical: 121 ± 96 μm |
| Triton X-114* | 1.2 g | 15.8% | Spherical: 19 ± 15 μm |

TABLE 6-continued

Synthesis results (pH = 2) by various non-ionic surfactants and amounts.

| Surfactant | Weight added | E.E. of SB-35 | Particle shape and size* |
|---|---|---|---|
| Brij 30* | 0.6 g | 0.8% | Spherical: 118 ± 50 μm |
| Brij 30 | 1.2 g | 11.4% | Broken particles |

E.E.: Encapsulation efficiency of SB-35 (solvent blue-35 dye).

*SEM images are shown in FIG. 38. The average particle sizes and standard deviations were calculated based on measuring 20 particles from SEM images.

TABLE 7

Synthesis (pH = 2) results by Tween 61 and Tween 81 at various amounts.

| Surfactant | Weight added | E.E. of SB-35 | Particle shape and size |
|---|---|---|---|
| Tween 61 | 0.15 g | 36.1% | Spherical: 120 ± 50 μm |
| Tween 61* | 0.3 g | 38.1% | Spherical: 134 ± 69 μm |
| Tween 61* | 0.6 g | 38.7% | Spherical: 83 ± 43 μm |
| Tween 61* | 1.2 g | 37.3% | Spherical: 82 ± 33 μm |
| Tween 81 | 0.15 g | 36.5% | Spherical: 106 ± 80 μm |
| Tween 81* | 0.3 g | 35.4% | Spherical: 134 ± 92 μm |
| Tween 81* | 0.6 g | 22.3% | Spherical: 96 ± 39 μm |
| Tween 81* | 1.2 g | 24.1% | Spherical: 91 ± 38 μm |

Figure 39:
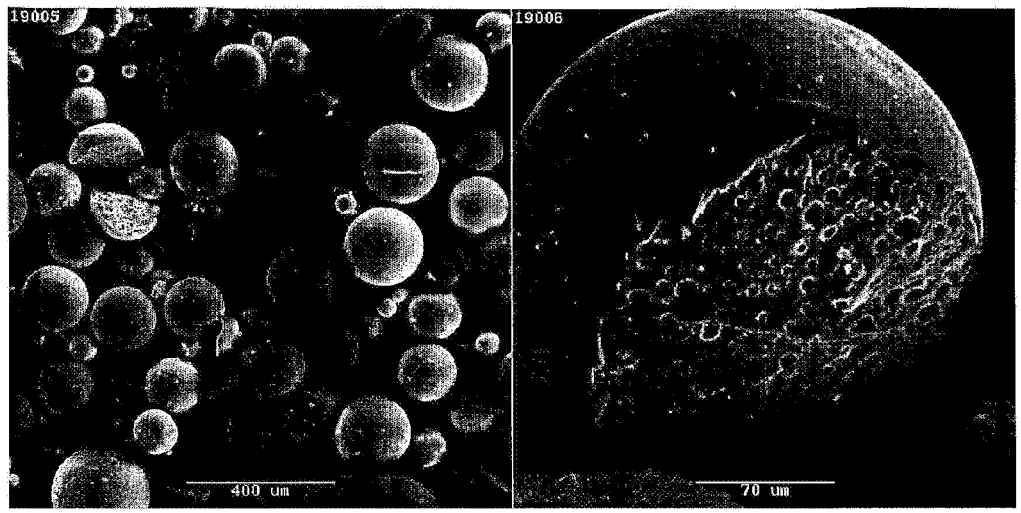
FIG. 39 shows SEM images of silica microparticles made using Tween 61 and Tween 81: (a) Tween 61/0.3 g; (b) Tween 61/0.6 g; (c) Tween 61/1.2 g; (d) Tween 81/0.3 g; (e) Tween 81/0.6 g; (f) Tween 81/1.2 g.
Figure 39:
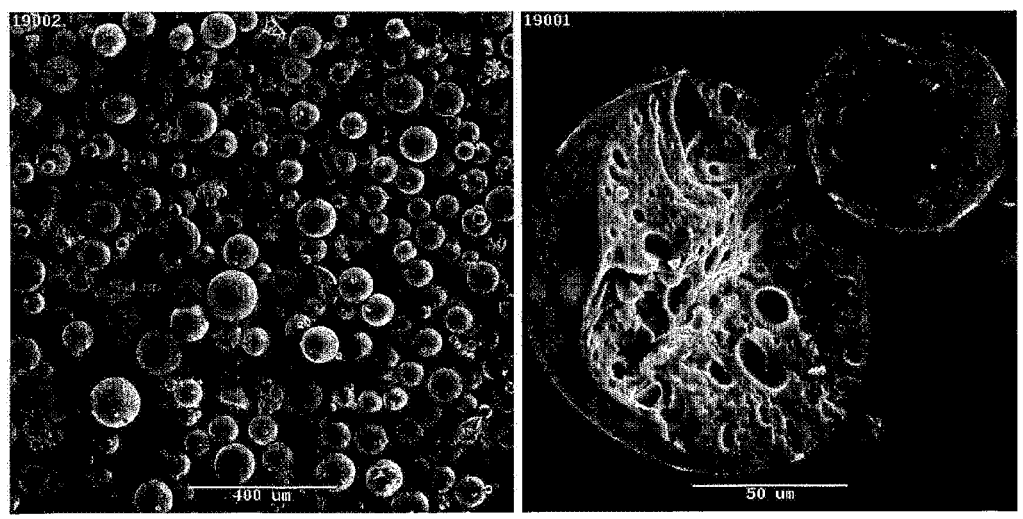
Figure 39:
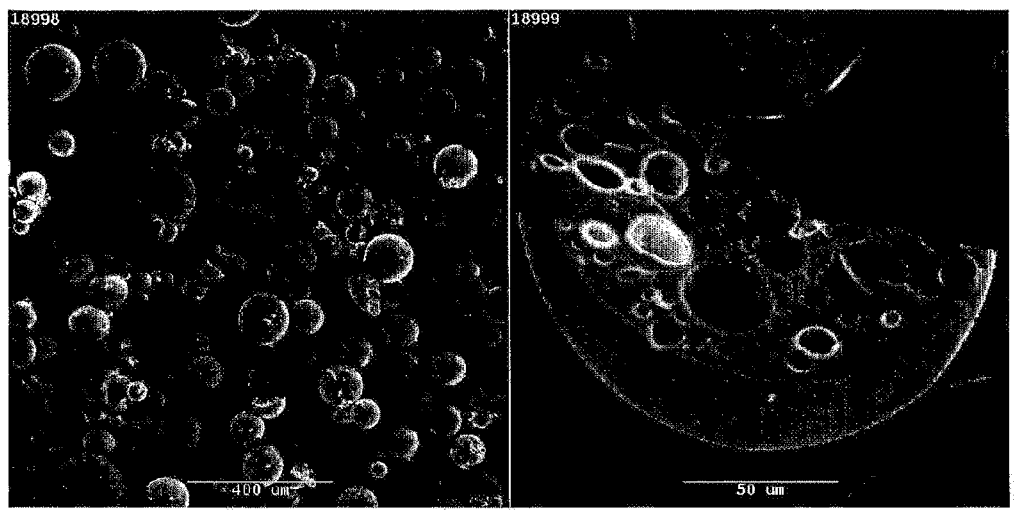
Figure 39:
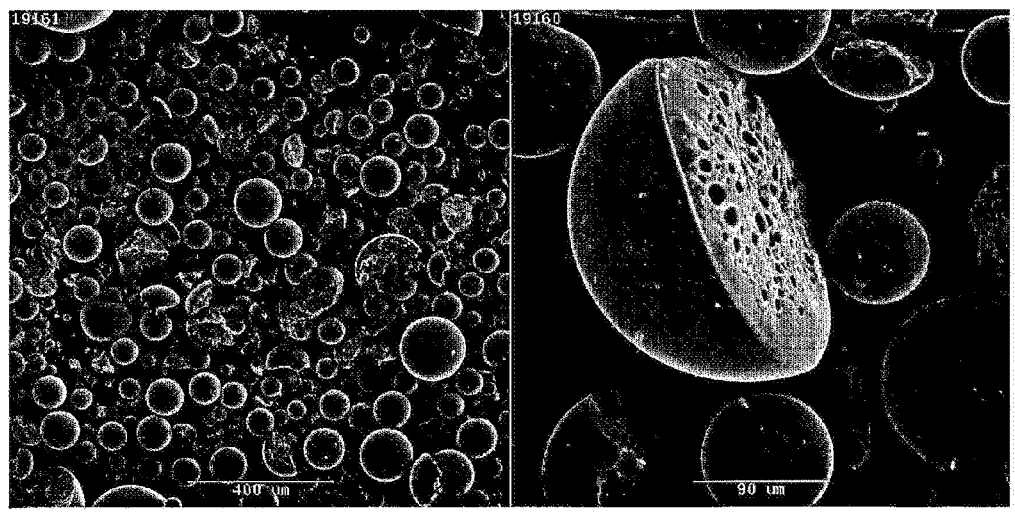
Figure 39:
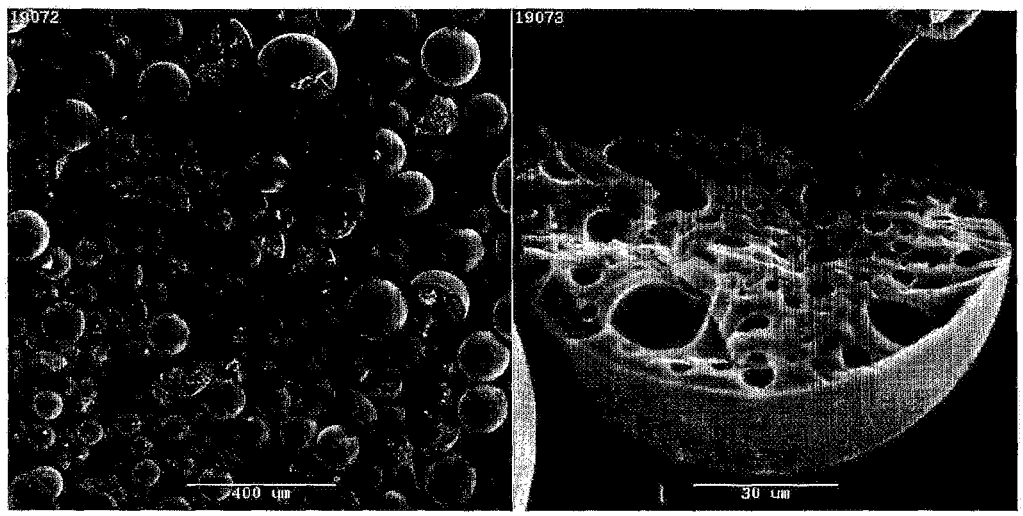
Figure 39:
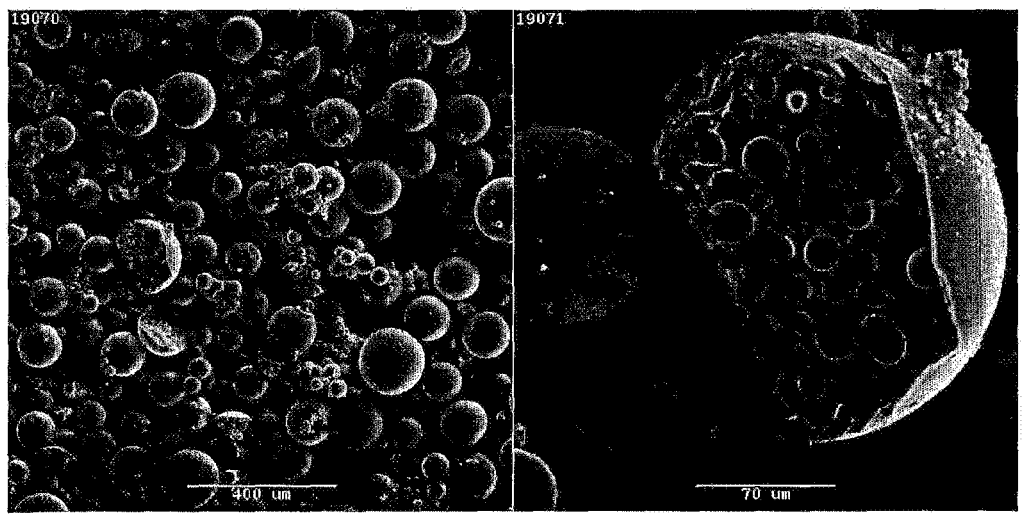

*SEM images are shown in FIG. 39. The average particle sizes and standard deviations were calculated based on measuring 20 particles from SEM images.

TABLE 8

BET results for various internal surfactants.

| | Tween 21 | Tween 61 | Tween 81 | Tween 20 | Tween 80 |
|---|---|---|---|---|---|
| PEG unit | 4 | 4 | 5 | 20 | 20 |
| Molecular weight | 522 | 606 | 650 | 1226 | 1310 |
| HLB value | 13.3 | 9.6 | 10 | 16.7 | 15 |
| BET surface area ($m^2/g$) | 431.3 | 500 | 499.8 | 168.3 | 322.8 |
| Pore volume (single point) ($cm^3/g$) | 0.51 | 0.29 | 0.28 | 0.13 | 0.43 |
| BJH average pore volume ($cm^3/g$) | 0.54 | 0.18 | 0.17 | 0.10 | 0.44 |
| BJH average pore diameter (nm) | 4.77 | 2.67 | 2.70 | 3.53 | 4.53 |
| Encapsulation Efficiency (%) of dye | 38.4 | 37.6 | 29.6 | ~0 | ~0 |

TABLE 9

Influence of the amount of internal surfactant and oil on particle size and encapsulation efficiency

| Surfactant | Limonene added | E.E. of SB-35 | Particle shape and size |
|---|---|---|---|
| Tween 61: 0.6 g | 0.714 mL | 38.7% | Spherical: 83 ± 43 μm |
| Tween 61: 1.2 g | 0.714 mL | 37.3% | Spherical: 82 ± 33 μm |
| Tween 61: 0.6 g | 1.428 mL | 31.8% | Broken species |
| Tween 61: 1.2 g | 1.428 mL | 6.9% | Broken species |
| Tween 81: 0.6 g | 0.714 mL | 22.3% | Spherical: 96 ± 39 μm |
| Tween 81: 1.2 g | 0.714 mL | 24.1% | Spherical: 91 ± 38 μm |
| Tween 81: 0.6 g | 1.428 mL | 14.4% | Broken species |
| Tween 81: 1.2 g | 1.428 mL | 8.5% | Broken species |

TABLE 10

Influence of the ageing time on particle size and encapsulation efficiency

| Ageing time | E.E. of SB-35 | Particle shape and size |
|---|---|---|
| 5 min. | 37.2% | Spherical: 118 ± 71 μm |
| 10 min | 44.7% | Spherical: 114 ± 52 μm |
| 20 min | 34.5% | Spherical: 120 ± 60 μm |
| 40 min | 33.4% | Spherical: 112 ± 56 μm |

TABLE 11

Influence of the methanol evaporation time on particle size and encapsulation efficiency

| Evaporation time | E.E. of SB-35 | Particle shape and size |
|---|---|---|
| 1.5 hr. | 38.7% | Spherical: 73 ± 27 μm |
| 1 hr. | 36.5% | Spherical: 70 ± 30 μm |
| 0.5 hr. | 36.0% | Spherical: 98 ± 63 μm |
| Without evaporation | 36.7% | Spherical: 100 ± 51 μm |

TABLE 12

Experimental condition for HPC addition.

| $C_{Span\ 80}$ (mol/L) | $M_{HPC}$ (g) | HPC carrier* | $Oil_2$ |
|---|---|---|---|
| 0.2 | 4 | hexanol | cyclohexane |
| 0.2 | 8 | hexanol | cyclohexane |
| 0.2 | 16 | hexanol | cyclohexane |
| 0.3 | 2.5 | none | cyclohexane |
| 0.3 | 5 | none | cyclohexane |
| 0.6 | 2.5 | none | cyclohexane |
| 0.6 | 5 | none | cyclohexane |
| 0.2 | 12.4 | decanol | decanol |
| 0.3 | 12.4 | decanol | decanol |
| 0.4 | 12.4 | decanol | decanol |
| 0.5 | 12.4 | decanol | decanol |

*(1) 25 wt. % HPC dissolved in hexanol which added into outer oil phase.
$_2$5 wt. % HPC in decanol used as outer oil phase.

TABLE 13

Experimental condition for EC7 addition*

| $C_{Span\ 80}$ (mol/L) | $M_{EC7}$ (g) | Particle shape and size |
|---|---|---|
| 0.2 | 5 | n/a |
| 0.4 | 5 | Spherical: 15-60 μm |
| 0.2 | 2.4 | Spherical: 20-100 μm |
| 0.3 | 2.4 | Spherical: 20-138 μm |
| 0.4 | 2.4 | Spherical: 20-160 μm |

*EC7 was directly added in cyclohexane.

TABLE 14

TGA/DTA results at various washing methods

| | Method | Surf./(silica + surf.) |
|---|---|---|
| 1* | 3 × 15 mL 1 mol/L NaCl + 3 × 15 mL water | 8.9 wt. % |
| 2* | 6 × 15 mL water | 11.9 wt. % |
| 3 | Tween 20 0.1% 3 × 15 mL | 17.7 wt. % |
| 4 | Tween 20 0.1% 6 × 15 mL | 41.1 wt. % |
| 5 | Tween 20 0.05% 3 × 15 mL | 18.4 wt. % |
| 6* | Tween 20 0.05% 6 × 15 mL | 17.7 wt. % |
| 7 | Tween 20 0.01% 3 × 15 mL | 37.4 wt. % |
| 8 | Tween 20 0.01% 6 × 15 mL | 20.3 wt. % |
| 9 | Tween 80 0.1% 3 × 15 mL | 39.7 wt. % |
| 10 | Tween 80 0.1% 6 × 15 mL | 36.5 wt. % |
| 11 | Tween 80 0.05% 3 × 15 mL | 15.2 wt. % |

TABLE 14-continued

TGA/DTA results at various washing methods

| Method | | Surf./(silica + surf.) |
|---|---|---|
| 12* | Tween 80 0.05% 6 × 15 mL | 16.9 wt. % |
| 13 | Tween 80 0.01% 3 × 15 mL | 12.6 wt. % |
| 14 | Tween 80 0.01% 6 × 15 mL | 14.1 wt. % |

*TGA/DTA diagrams provided in FIG. 48.

TABLE 15

BET and DFT results at different amount of internal surfactants (pH 1).

| Tween 61 mass (mg) | 150 | 300 | 600 |
|---|---|---|---|
| BET surface area ($m^2/g$) | 96.5 | 62.0 | 309.9 |
| BET average pore diameter (nm) | 2.252 | 2.617 | 2.000 |
| Median pore diameter (nm) | 1.643 | 2.188 | 1.640 |
| Peak of pores (nm) (DFT) | 1.952 | 1.916 | 1.987 |

TABLE 16

Experiment results of diuron encapsulated silica microparticles.

| Tween 21 | 0.6 g | 0.3 g | 0.16 g |
|---|---|---|---|
| Product | 2.635 g | 2.344 g | 1.794 g |
| particle | sphere | sphere | Sphere |
| Recovery[1] | 71.1% | 69.2% | 64.75% |
| EE based on released[2] | 7.43% | 3.86% | 3.52% |
| EE based on lost[3] | 36.36% | 34.64% | 38.78% |

[1]Recovery = (diuron in powder + diuron in organic phase)/diuron added
[2]EE = diuron in powder/diuron added
[3]EE = (diuron added − diuron lost in organic phase)/diuron added

TABLE 17

HPLC results of basil oil (Quest International) encapsulated silica microparticles.

| | Basil oil | | | |
|---|---|---|---|---|
| | 0.35 mL | 0.70 mL | 0.35 mL | 0.70 mL |
| Tween 21 | 0.3 g | 0.3 g | 0.6 g | 0.6 g |
| Product | 3.080 g | 2.916 g | 3.190 g | 3.058 g |
| particle | Sphere | Sphere | Sphere | Sphere |
| Recovery[1] | 88.5% | 61.7% | 85.4% | 86.2% |
| EE based on released[2] | 2.83% | 1.99% | 1.82% | 0.654% |
| EE based on lost[3] | 14.31% | 40.25% | 16.41% | 14.47% |

[1]Recovery = (linalool in powder + linalool in organic phase)/linalool added
[2]EE = linalool in powder/linalool added
[3]EE = (linalool added − linalool lost in organic phase)/linalool added

The invention claimed is:

1. A process for preparing porous ceramic particles having a hydrophobic material therein, said process comprising:
   agitating a mixture of a hydrophobic phase, water, and a first surfactant having HLB of about 8 to about 20 to form an inner emulsion, said hydrophobic phase comprising the hydrophobic material;
   combining a precursor to a ceramic with water so as to form a second mixture;
   combining the inner emulsion with the second mixture and agitating the resulting mixture to form the inner emulsion plus precursor;
   combining a second surfactant having a HLB of about 1 to about 8 and a hydrophobic medium so as to form a third mixture;
   agitating the inner emulsion plus precursor with the third mixture so as to disperse the inner emulsion plus precursor in the hydrophobic medium, thereby forming a double emulsion; and
   aging the double emulsion so as to form the porous ceramic particles having the hydrophobic material therein disposed within pores of said ceramic particles.

2. The process of claim 1, wherein the double emulsion is aged for a time of between about 5 and about 30 minutes.

3. The process of claim 1, wherein the step of combining the crosslinkable species with water is conducted at pH of about 1 to about 3.

4. The process of claim 1, wherein the double emulsion is an oil-in-water-in-oil (O/W/O) double emulsion.

5. The process of claim 1, wherein the precursor is a hydrolysable silane, an at least partially hydrolysed silane, a partially crosslinked silane, or a mixture of any two or more of these.

6. The process of claim 1, wherein the hydrophobic phase comprises a hydrophobic diluent in addition to the hydrophobic material.

7. The process of claim 1, wherein the hydrophobic material is selected from the group consisting of a fluorescent dye, a radiopharmaceutical, a drug, an enzyme, a catalyst, a hormone, a biocide, a flavor, an aroma substance, and a mixture of any two or more of these.

8. The process of claim 1, wherein no emulsion stabiliser other than a surfactant is added.

9. The process of claim 1, wherein inner emulsion is a microemulsion.

10. The process of claim 1, wherein the inner emulsion has a mean droplet diameter between about 10 nm and about 50 microns.

11. The process of claim 1, wherein the double emulsion has a mean droplet diameter between about 0.1 and about 1000 microns.

12. The process of claim 1, further comprising one or more of the steps of:
   at least partially separating the particles from the hydrophobic medium;
   washing the particles;
   and drying the particles.

13. The process of claim 1, comprising at least partially separating the particles from the hydrophobic medium and then further aging the particles for between about 1 hour and about 24 hours.

14. The process of claim 1, wherein the step of aging comprises one or more of polymerizing, condensing, solidifying, or crosslinking the precursor in the double emulsion to form the ceramic particles having the hydrophobic material therein, said hydrophobic material being releasable from said particles.

* * * * *